US010966700B2

(12) United States Patent
Farritor et al.

(10) Patent No.: US 10,966,700 B2
(45) Date of Patent: Apr. 6, 2021

(54) ROBOTIC SURGICAL DEVICES, SYSTEMS AND RELATED METHODS

(71) Applicant: Virtual Incision Corporation, Lincoln, NE (US)

(72) Inventors: Shane Farritor, Lincoln, NE (US); Christopher Santoro, Brooklyn, NY (US); Jeffrey Shasho, Brooklyn, NY (US); Nishant Kumar, Bergenfield, NJ (US); Mateusz Szczesiak, Forest Hills, NY (US); Jason Herman, East Northport, NY (US)

(73) Assignee: Virtual Incision Corporation, Lincoln, NE (US)

( * ) Notice: Subject to any disclaimer, the term of this patent is extended or adjusted under 35 U.S.C. 154(b) by 0 days.

(21) Appl. No.: 14/334,383

(22) Filed: Jul. 17, 2014

(65) Prior Publication Data
US 2015/0051446 A1    Feb. 19, 2015

Related U.S. Application Data

(60) Provisional application No. 61/847,394, filed on Jul. 17, 2013.

(51) Int. Cl.
*A61B 46/10*    (2016.01)
*A61B 34/30*    (2016.01)
*A61B 17/02*    (2006.01)
*A61B 1/313*    (2006.01)
*A61B 90/00*    (2016.01)

(52) U.S. Cl.
CPC ........ *A61B 17/0218* (2013.01); *A61B 1/3132* (2013.01); *A61B 34/30* (2016.02); *A61B 46/10* (2016.02); *A61B 90/361* (2016.02)

(58) Field of Classification Search
CPC ............ A61B 1/00064; A61B 1/00087; A61B 1/00131; A61B 1/00154; A61B 1/01
USPC ........ 600/101, 104, 107, 112, 114, 121–125, 600/170–173, 176; 606/32–58
See application file for complete search history.

(56) References Cited

U.S. PATENT DOCUMENTS

| 3,870,264 A | 3/1975 | Robinson |
| 3,989,952 A | 11/1976 | Timberlake et al. |
| 4,246,661 A | 1/1981 | Pinson |
| 4,258,716 A | 3/1981 | Sutherland |

(Continued)

FOREIGN PATENT DOCUMENTS

| CN | 1082821918 | 12/2012 |
| DE | 102010040405 | 3/2012 |

(Continued)

OTHER PUBLICATIONS

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.

(Continued)

*Primary Examiner* — Matthew J Kasztejna
(74) *Attorney, Agent, or Firm* — Davis, Brown, Koehn Shors & Roberts, P.C.; Sean D. Solberg

(57) ABSTRACT

The various inventions relate to robotic surgical devices, consoles for operating such surgical devices, operating theaters in which the various devices can be used, insertion systems for inserting and using the surgical devices, and related methods.

22 Claims, 52 Drawing Sheets

(56) References Cited

U.S. PATENT DOCUMENTS

| | | |
|---|---|---|
| 4,278,077 A | 7/1981 | Mizumoto |
| 4,538,594 A | 9/1985 | Boebel et al. |
| 4,568,311 A | 2/1986 | Miyaki |
| 4,623,183 A | 11/1986 | Amori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,897,014 A | 1/1990 | Tietze |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,441,494 A | 1/1995 | Oritz |
| 5,388,528 A | 2/1995 | Pelrine et al. |
| 5,436,542 A | 7/1995 | Petelin et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Shuichi et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,900 A | 8/1998 | Madhani et al. |
| 5,807,377 A | 9/1998 | Madhani et al. |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,911,036 A | 6/1999 | Wright et al. |
| 5,971,976 A | 10/1999 | Wang et al. |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Niemeyer et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |

(56) References Cited

U.S. PATENT DOCUMENTS

| | | |
|---|---|---|
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,179,073 B2 | 5/2012 | Farritor et al. |
| 8,353,897 B2 | 1/2013 | Doyle et al. |
| 8,888,687 B2 * | 11/2014 | Ostrovsky ............ A61B 1/0008 600/106 |
| 9,089,353 B2 | 7/2015 | Farritor |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |

(56) References Cited

U.S. PATENT DOCUMENTS

| | | |
|---|---|---|
| 2002/0026186 A1 | 2/2002 | Woloszka et al. |
| 2002/0038077 A1 | 3/2002 | de la Torre et al. |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julien et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0117032 A1 | 1/2004 | Roth et al. |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0138525 A1 | 7/2004 | Saadat |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Khalili et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0234294 A1* | 10/2005 | Saadat ............... A61B 1/0008 600/104 |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0021440 A1* | 1/2008 | Solomon ............... B25J 9/1045 606/1 |
| 2008/0033569 A1 | 2/2008 | Ferren et al. |
| 2008/0045803 A1 | 2/2008 | Williams |
| 2008/0058835 A1 | 3/2008 | Farritor et al. |
| 2008/0058989 A1 | 3/2008 | Oleynikov et al. |
| 2008/0071289 A1* | 3/2008 | Cooper ............... A61B 1/00087 606/130 |
| 2008/0103440 A1 | 5/2008 | Ferren et al. |
| 2008/0109014 A1 | 5/2008 | Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 7/2008 | Rioux et al. |
| 2008/0164079 A1 | 7/2008 | Ferren et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1* | 7/2009 | Farritor ............... A61B 19/2203 606/130 |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Manzo et al. |
| 2010/0204713 A1 | 8/2010 | Ruiz |
| 2010/0245549 A1 | 9/2010 | Allen et al. |

(56) References Cited

U.S. PATENT DOCUMENTS

| | | | |
|---|---|---|---|
| 2010/0262162 A1 | 10/2010 | Omori | |
| 2010/0292691 A1 | 11/2010 | Brogna | |
| 2010/0318059 A1 | 12/2010 | Farritor et al. | |
| 2011/0015569 A1 | 1/2011 | Kirschenman et al. | |
| 2011/0020779 A1 | 1/2011 | Hannaford et al. | |
| 2011/0071347 A1 | 3/2011 | Rogers et al. | |
| 2011/0071544 A1 | 3/2011 | Steger et al. | |
| 2011/0077478 A1 | 3/2011 | Freeman et al. | |
| 2011/0098529 A1* | 4/2011 | Ostrovsky | A61B 1/0008 600/104 |
| 2011/0152615 A1* | 6/2011 | Schostek | A61B 19/2203 600/111 |
| 2011/0224605 A1 | 9/2011 | Farritor et al. | |
| 2011/0230894 A1 | 9/2011 | Simaan et al. | |
| 2011/0237890 A1 | 9/2011 | Farritor et al. | |
| 2011/0238080 A1 | 9/2011 | Ranjit et al. | |
| 2011/0264078 A1 | 10/2011 | Lipow | |
| 2011/0270443 A1 | 11/2011 | Kamiya et al. | |
| 2012/0035582 A1 | 2/2012 | Nelson et al. | |
| 2012/0109150 A1 | 5/2012 | Quaid et al. | |
| 2012/0116362 A1 | 5/2012 | Kieturakis | |
| 2012/0179168 A1 | 7/2012 | Farritor | |
| 2012/0253515 A1 | 10/2012 | Coste-Maniere et al. | |
| 2013/0041360 A1 | 2/2013 | Farritor | |
| 2013/0131695 A1* | 5/2013 | Scarfogliero | A61B 19/2203 606/130 |
| 2013/0345717 A1* | 12/2013 | Markvicka | A61B 34/30 606/130 |
| 2014/0039515 A1 | 1/2014 | Mondry et al. | |
| 2014/0046340 A1 | 2/2014 | Wilson et al. | |
| 2014/0058205 A1 | 2/2014 | Frederick et al. | |
| 2014/0303434 A1 | 10/2014 | Farritor et al. | |
| 2015/0051446 A1 | 2/2015 | Farritor et al. | |

FOREIGN PATENT DOCUMENTS

| | | |
|---|---|---|
| EP | 1354670 | 10/2003 |
| EP | 2123225 | 11/2009 |
| EP | 2286756 A1 | 2/2011 |
| EP | 2563261 | 3/2013 |
| JP | 2004144533 | 5/1990 |
| JP | 5115425 | 5/1993 |
| JP | 200716235 | 6/1993 |
| JP | 2006507809 | 9/1994 |
| JP | 07 136173 | 5/1995 |
| JP | 7306155 | 11/1995 |
| JP | 08-224248 | 9/1996 |
| JP | 2002000524 A | 6/2000 |
| JP | 2001505810 | 5/2001 |
| JP | 2003220065 | 8/2003 |
| JP | 2004322310 | 6/2004 |
| JP | 2004180781 | 7/2004 |
| JP | 2004329292 | 11/2004 |
| JP | 2006508049 | 3/2006 |
| JP | 2009-106606 | 5/2009 |
| JP | 2010-533045 | 10/2010 |
| JP | 2010-536436 | 12/2010 |
| JP | 2011-504794 | 2/2011 |
| JP | 2011-045500 | 3/2011 |
| JP | 2011-115591 | 6/2011 |
| WO | WO 1992/21291 | 5/1991 |
| WO | WO 0189405 | 11/2001 |
| WO | WO 2002/082979 | 10/2002 |
| WO | WO 2002/100256 | 12/2002 |
| WO | WO 2005/009211 | 7/2004 |
| WO | WO 2005044095 | 5/2005 |
| WO | WO 2006/052927 | 8/2005 |
| WO | WO 2006 005075 | 1/2006 |
| WO | WO 2006/079108 | 1/2006 |
| WO | WO 2007011654 | 1/2007 |
| WO | WO 2007/111571 | 10/2007 |
| WO | WO 2007/149559 | 12/2007 |
| WO | WO 2009023851 A1 | 8/2008 |
| WO | WO 2009/144729 | 12/2009 |
| WO | WO2010/042611 | 4/2010 |
| WO | WO2010/046823 | 4/2010 |
| WO | WO201050771 A2 | 5/2010 |
| WO | WO 2011/135503 A1 | 11/2011 |
| WO | WO 2011135503 | 11/2011 |
| WO | WO 2011075693 | 7/2012 |
| WO | 2013009887 A1 | 1/2013 |
| WO | WO 2013009887 | 1/2013 |
| WO | WO 2011/118646 A1 | 7/2013 |
| WO | WO 2014011238 | 1/2014 |

OTHER PUBLICATIONS

Allendorf et al., "Postoperative Immune Function Varies Inversely with the Degree of Surgical Trauma in a Murine Model," Surgical Endoscopy 1997; 11:427-430.

Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.

Applicant Amendment after Notice of Allowance under Rule 312, filed Aug. 25, 2008, in related case U.S. Appl. No. 11/695,944, 6pp.

Applicant Response to Office Action dated Apr. 17, 2007, in related case U.S. Appl. No. 11/552,379, filed Aug. 8, 2007, 7 pp.

Applicant Response to Office Action dated Aug. 18, 2006, in related case U.S. Appl. No. 11/398,174, filed Nov. 7, 2006, 8pp.

Applicant Response to Office Action dated Aug. 21, 2006, in related case U.S. Appl. No. 11/403,756, filed Nov. 21, 2006, 52pp.

Applicant Response to Office Action dated Oct. 29, 2007, in related case U.S. Appl. No. 11/695,944, filed Jan. 22, 2008, 6pp.

Atmel 80C5X2 Core, http://www.atmel.com, 2006, 186pp.

Bailey et al., "Complications of Laparoscopic Surgery," Quality Medical Publishers, Inc., 1995, 25pp.

Ballantyne, "Robotic Surgery, Telerobotic Surgery, Telepresence, and Telementoring," Surgical Endoscopy, 2002; 16: 1389-1402.

Bauer et al., "Case Report: Remote Percutaneous Renal Percutaneous Renal Access Using a New Automated Telesurgical Robotic System," Telemedicine Journal and e-Health 2001; (4): 341-347.

Begos et al., "Laparoscopic Cholecystectomy: From Gimmick to Gold Standard," J Clin Gastroenterol, 1994; 19(4): 325-330.

Berg et al., "Surgery with Cooperative Robots," Medicine Meets Virtual Reality, Feb. 2007, 1 pg.

Breda et al., "Future developments and perspectives in laparoscopy," Eur. Urology 2001; 40(1): 84-91.

Breedveld et al., "Design of Steerable Endoscopes to Improve the Visual Perception of Depth During Laparoscopic Surgery," ASME, Jan. 2004; vol. 126, pp. 1-5.

Breedveld et al., "Locomotion through the Intestine by means of Rolling Stents," Proceedings of the ASME Design Engineering Technical Conferences, 2004, pp. 1-7.

Calafiore et al., Multiple Arterial Conduits Without Cardiopulmonary Bypass: Early Angiographic Results,: Ann Thorac Surg, 1999; 67: 450-456.

Camarillo et al., "Robotic Technology in Surgery: Past, Present and Future," The American Journal of Surgery, 2004; 188: 2S-15.

Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.

Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.

Chanthasopeephan et al., (2003), "Measuring Forces in Liver Cutting: New Equipment and Experimenal Results," Annals of Biomedical Engineering 31: 1372-1382.

Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.

Cuschieri, "Technology for Minimal Access Surgery," BMJ, 1999, 319: 1-6.

(56) References Cited

OTHER PUBLICATIONS

Dakin et al., "Comparison of laparoscopic skills performance between standard instruments and two surgical robotic systems," Surg Endosc., 2003; 17: 574-579.
Dumpert et al., "Improving in Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Falcone et al., "Robotic Surgery," Clin. Obstet. Gynecol. 2003, 46(1): 37-43.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al., "Tomorrow's Surgery: micromotors and microbots for minimally invasive procedures," Minimally Invasive Surgery & Allied Technologies.
Franklin et al., "Prospective Comparison of Open vs. Laparoscopic Colon Surgery for Carcinoma: Five-Year Results," Dis Colon Rectum, 1996; 39: S35-S46.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Grady, "Doctors Try New Surgery for Gallbladder Removal," The New York Times, Apr. 20, 2007, 3 pp.
International Preliminary Report on Patentability from related case PCT/US2007/014567, dated Jan. 8, 2009, 11 pp.
International Search report and Written Opinion from international application No. PCT/US2012/41911, dated Mar. 13, 2013.
International Search Report and Written Opinion from international application No. PCT/US12/46274, dated Sep. 25, 2012.
International Search Report and Written Opinion from international application No. PCT/US2007/089191, dated Nov. 10, 2008, 20 pp.
"International Search Report and Written Opinion from international application No. PCT/US07/14567, dated Apr. 28, 2008, 19 pp."
International Search Report and Written Opinion of international application No. PCT/US2008/069822, dated Aug. 5, 2009, 12 pp.
International Search Report and Written Opinion of international application No. PCT/US2008/073334, dated Jan. 12, 2009, 11 pp.
International Search Report and Written Opinion of international application No. PCT/US2008/073369, dated Nov. 12, 2008, 12 pp.
International Search Report and Written Opinion issued in PCT/US11/46809, dated Dec. 8, 2011.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coli. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
Macfarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, 1/4-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.

(56) References Cited

OTHER PUBLICATIONS

Office Action dated Apr. 3, 2009, received in related case U.S. Appl. No. 11/932,516, 43 pp.
Office Action dated Aug. 18, 2006, received in related case U.S. Appl. No. 11/398,174, 6 pp.
Office Action dated Aug. 21, 2006, received in related case U.S. Appl. No. 11/403,756, 6 pp.
Office Action dated Oct. 29, 2007, received in related case U.S. Appl. No. 11/695,944, 6 pp.
Office Action dated Oct. 9, 2008, received in related case U.S. Appl. No. 11/932,441, 4 pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. 1192-1196 Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy a Breakthrough Diagnostic Tool for Small Intestine Imagining, " vol. 25, No. 1, Gastroenterology Nursing, pp. 24-27.
International Search Report and Written Opinion of international application No. PCT/US2010/061137, dated Feb. 11, 2011, 10 pp.
Abbou et al., "Laparoscopic Radical Prostatectomy with a Remote Controlled Robot," The Journal of Urology, Jun. 2001, 165: 1964-1966.
Glukhovsky et al.., "The development and application of wireless capsule endoscopy," Int. J. Med. Robot. Comput. Assist. Surgery, 2004; I (1): 114-123.
Gong et al., Wireless endoscopy, Gastrointestinal Endoscopy 2000; 51(6): 725-729.
Hanly et al., "Value of the SAGES Learning Center in introducing new technology," Surgical Endoscopy, 2004; 19 (4): 477-483.
Hanly et al., "Robotic Abdominal Surgery," The American Journal of Surgery 188 (Suppl.to Oct. 1994): 19S-26S, 2004.
Heikkinen et al., "Comparison of laparoscopic and open Nissen fundoplication two years after operation: A prospective randomized trial," Surgical Endoscopy, 2000; 14: 1019-1023.
Hissink, "Olympus Medical develops capsule camera technology," Dec. 2004, accessed Aug. 29, 2007, http://www.letsgodigital.org , 3 pp.
Horgan et al., "Technical Report: Robots in Laparoscopic Surgery," Journal of Laparoendoscopic & Advanced Surgical Techniques, 2001; 11(6): 415-419.
Patronik et al., "Development of a Tethered Epicardial Crawler for Minimally Invasive Cardiac Therapies," IEEE, pp. 239-240.
Patronik et al., "Crawling on the Heart: A Mobile Robotic Device for Minimally Invasive Cardiac Interventions," MICCAI, 2004, pp. 9-16.
Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Analysis and Development of Locomotion Devices for the Gastrointestinal Tract," IEEE Transaction on Biomedical Engineering, vol. 49, No. 6, Jun. 2002, pp. 613-616.
Phee et al., "Development of Microrobotic Devices for Locomotion in the Human Gastrointestinal Tract," International Conference on Computational Intelligence, Robotics and Autonomous Systems (CIRAS 2001), Nov. 28-30, (2001), Singapore.
Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.
Preliminary Amendment filed Apr. 11, 2007, in related case U.S. Appl. No. 11/403,756, 7 pp.
Preliminary Amendment filed Jul. 30, 2008, in related case U.S. Appl. No. 12/171,413, 4 pp.
RCE and Amendment filed Jun. 13, 2007, in related case U.S. Appl. No. 11/403,756, 8 pp.
Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006e.
Rentschler et al., Mobile In Vivo Biopsy Robot, IEEE International Conference on Robotics and Automation, Orlando, Florida, May 2006, pp. 4155-4160.
Rentschler et al., "Miniature in vivo Robots for Remote and Harsh Environments," IEEE Transactions on Information Technology in Biomedicine, Jan. 2006; 12(1): 66-75.
Rentschler et al., "An In Vivo Mobile Robot for Surgical Vision and Task Assistance," Journal of Medical Devices, Mar. 2007, vol. 1: 23-29.
Rentschler et al., "In vivo Mobile Surgical Robotic Task Assistance," 1 pg.
Rentschler et al., "In vivo Robotics during the NEEMO 9 Mission," Medicine Meets Virtual Reality, Feb. 2007, I pg.
Rentschler et al.., "In Vivo Robots for Laparoscopic Surgery," Studies in Health Technology and Infonnatics—Medicine Meets Virtual Reality, ISO Press, Newport Beach, CA, 2004a, 98: 316-322.
Rentschler et al., "Mechanical Design of Robotic In Vivo Wheeled Mobility," ASME Journal of Mechanical Design, 2006a, pp. I-II.
Rentschler et al., "Mobile In Vivo Camera Robots Provide Sole Visual Feedback for Abdominal Exploration and Cholecystectomy," Journal of Surgical Endoscopy, 20-I: 135-138, 2006b.
Rentschler et al., "Mobile In Vivo Robots Can Assist in Abdominal Exploration," from the Proceedings of the Society of American

(56) References Cited

OTHER PUBLICATIONS

Gastrointestinal Endoscopic Surgeons (SAGES) Scientific Conference, Ft. Lauderdale, FL, Apr. 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Natural Orifice Surgery with an Endoluminal Mobile Robot," The Society of American Gastrointestinal Endoscopic Surgeons, Dallas, TX, Apr. 2006d, 14 pp.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.
Rentschler et al., "Toward In Vivo Mobility," Studies in Health Technology and Informatics—Medicine Meets Virtual Reality, ISO Press, Long Beach, CA, 2005a, III: 397-403.
Response to Rule 312 Amendment in related case U.S. Appl. No. 11/695,944, dated Jan. 12, 2009, 2 pp.
Riviere et al., "Toward Active Tremor Canceling in Handheld Microsurgical Instruments," IEEE Transactions on Robotics and Automation, Oct. 2003, 19(5): 793-800.
Rosen et al., "Force Controlled and Teleoperated Endoscopic, Grasper for Minimally Invasive Surgery-Experimental Performance Evaluation," IEEE Transactions of Biomedical Engineering, Oct. 1999; 46(10): 1212-1221.
Rosen et al., "Objective Laparoscopic Skills Assessments of Surgical Residents Using Hidden Markov Models Based on Haptic Information and Tool/Tissue Interactions," Studies in Health Technology and Infornnatics—Medicine Meets Virtual Reality, Jan. 2001, 7 pp.
Rosen et al., "Spherical Mechanism Analysis of a Surgical Robot for Minimally Invasive Surgery—Analytical and Experimental Approaches," Studies in Health Technology and Infornnatics—Medicine Meets Virtual Reality, pp. 442-448, Jan. 2005.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Ruurda et al., "Robot-Assisted surgical systems: a new era in laparoscopic surgery," Ann R. Coll Surg Engl., 2002; 84: 223-226.
Ruurda et al., "Feasibility of Robot-Assisted Laparoscopic Surgery," Surgical Laparoscopy, Endoscopy & Percutaneous Techniques, 2002; 12(1):41-45.
Sackier et al., "Robotically assisted laparoscopic surgery," Surgical Endoscopy, 1994; 8: 63-66.
Salky, "What is the Penetration of Endoscopic Techniques into Surgical Practice?" Digestive Surgery, 2000; 17:422-426.
Satava, "Surgical Robotics: The Early Chronicles," Surgical Laparoscopy, Endoscopy & Percutaneous Techniques, 2002; 12(1): 6-16.

Schippers et al., (1996) "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fastastic Voyage: Smart Pill to Expand Testing," http://www.smartpilldiagnostics.com, Apr. 13, 2005, 1 pg.
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al.., "Long-term Pain: Less Common After Laparoscopic than Open Cholecystectomy," British Journal of Surgery, 1994; 81: 1368-1370.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al.. (1993), "Sensing and Manipulation Problems in Endoscopic Surgery: Experiment, Analysis, and Observation," Presence 2( 1): 66-81.
Palm, William, "Rapid Prototyping Primer" May 1998 (revised Jul. 30, 2002) (http://www.me.psu.edu/lamancusa/rapidpro/primer/chapter2.htm).
Guo et al., "Micro Active Guide Wire Catheter System—Characteristic Evaluation, Electrical Model and Operability Evaluation of Micro Active Catheter," Proceedings of the 1996 IEEE International Conference on Robotics and Automation, Apr. 1996: 2226-2231.
Guo et al., "Fish-like Underwater Microrobot with 3 DOF," Proceedings of the 2002 IEEE International Conference on Robotics & Automation, May 2002: 738-743.
Stoianovici et al., "Robotic Tools for Minimally Invasive Urologic Surgery", Jan. 1, 2002, pp. 1-17.
Cleary et al, "State of the Art in Surgical Rootics: Clinical Applications and Technology Challenges", "Computer Aided Surgery", Jan. 1, 2002, pp. 312-328, vol. 6.
Green, "Telepresence Surgery", Jan. 1, 1995, Publisher: IEEE Engineering in Medicine and Biology.
Franzino, "The Laprotek Surgical System and the Next Generation of Robotics," Surg Clin North Am, 2003 83(6): 1317-1320.

\* cited by examiner

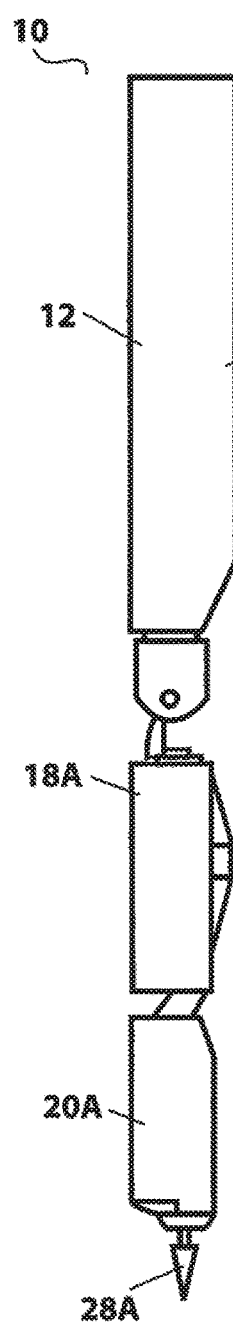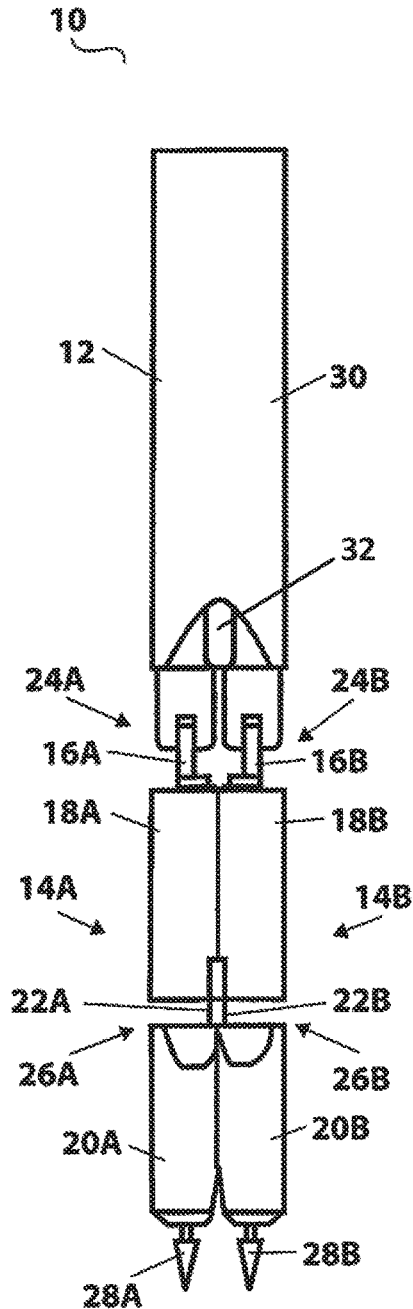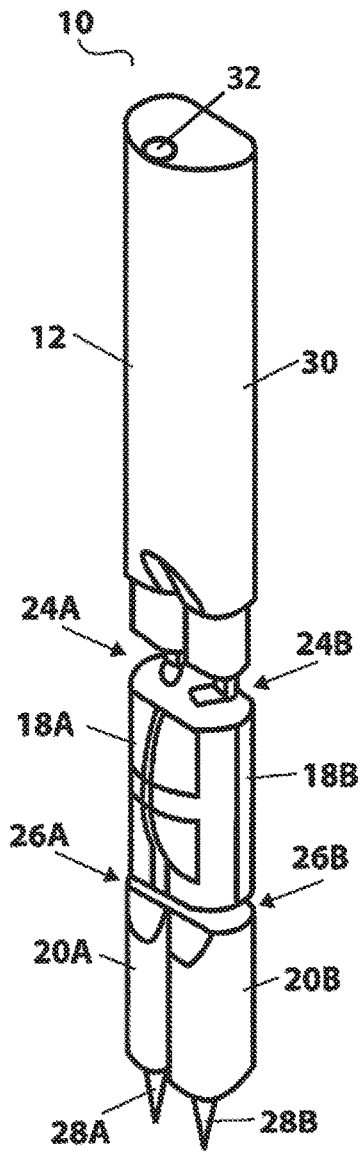
FIG. 1A   FIG. 1B   FIG. 1C
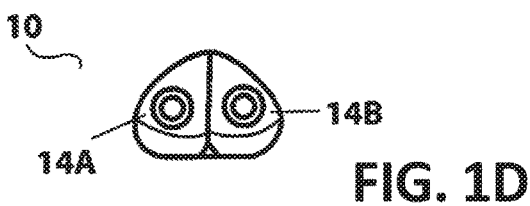
FIG. 1D

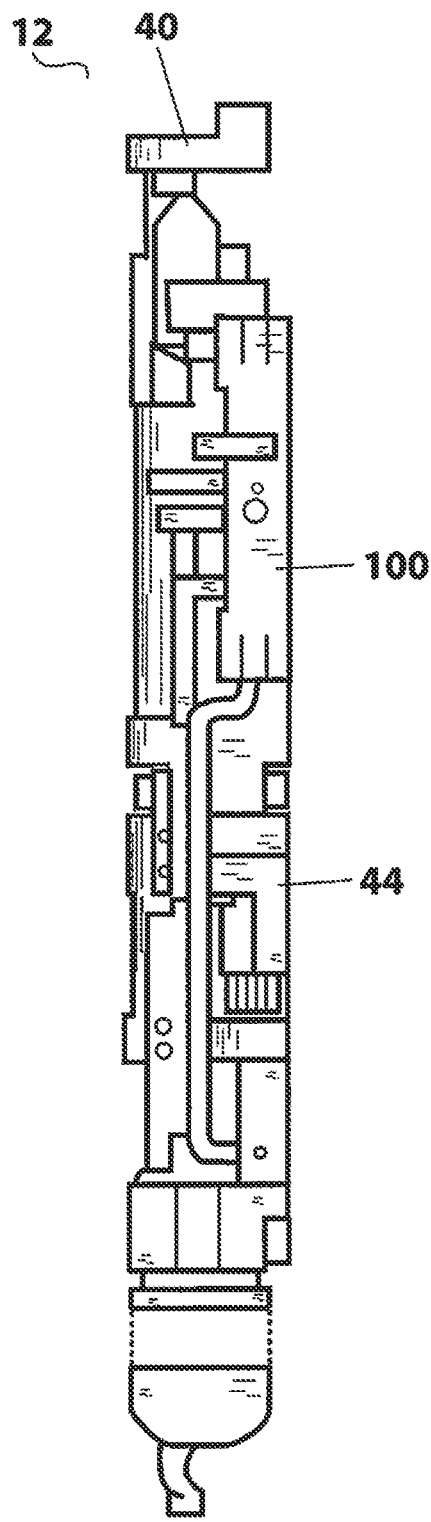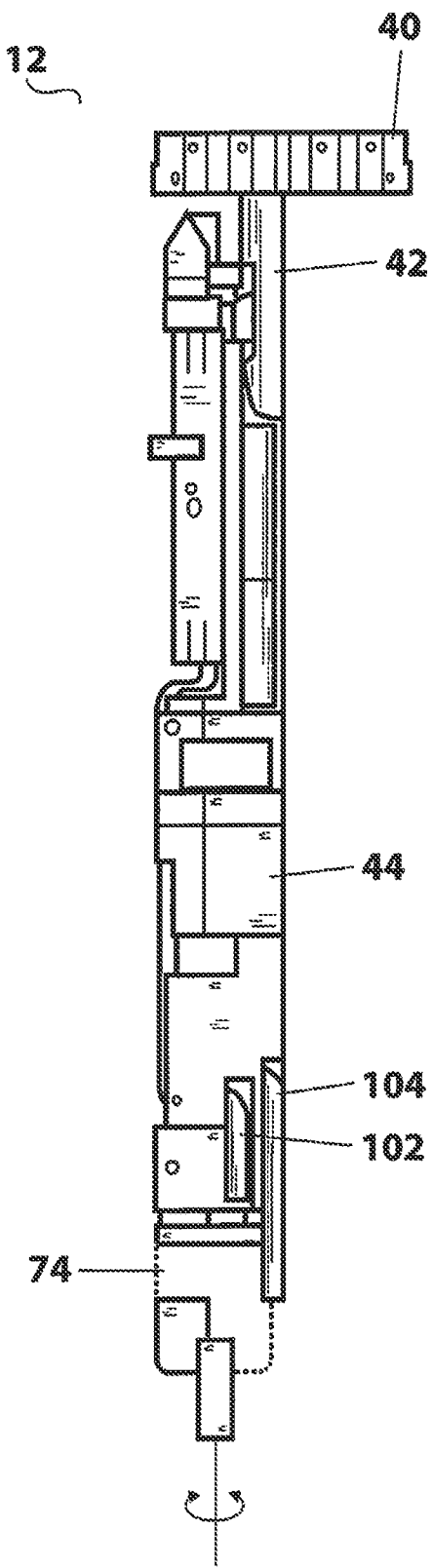
FIG. 2A
FIG. 2B

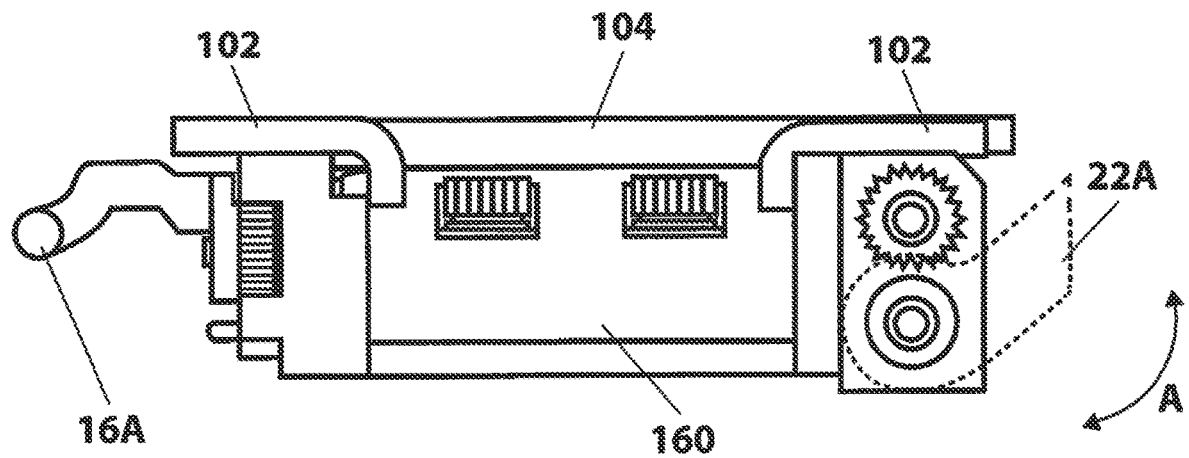
FIG. 4B
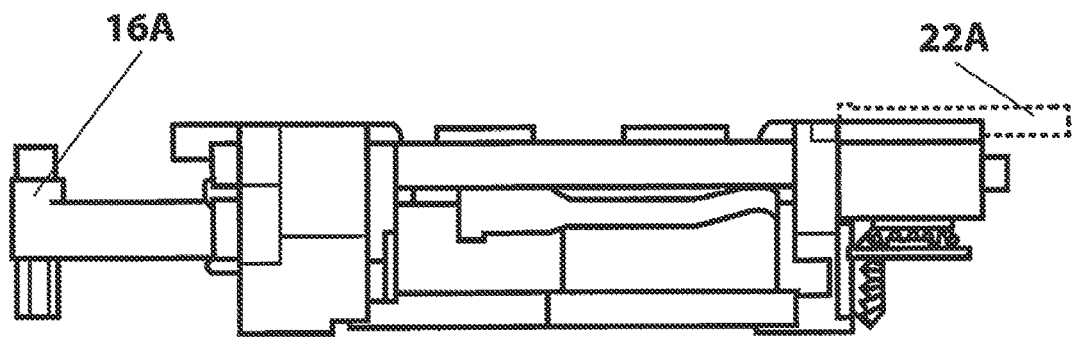
FIG. 4C
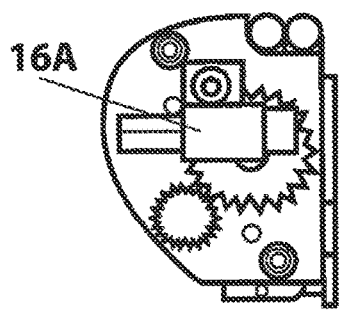 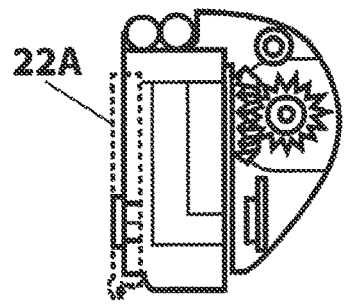
FIG. 4D          FIG. 4E

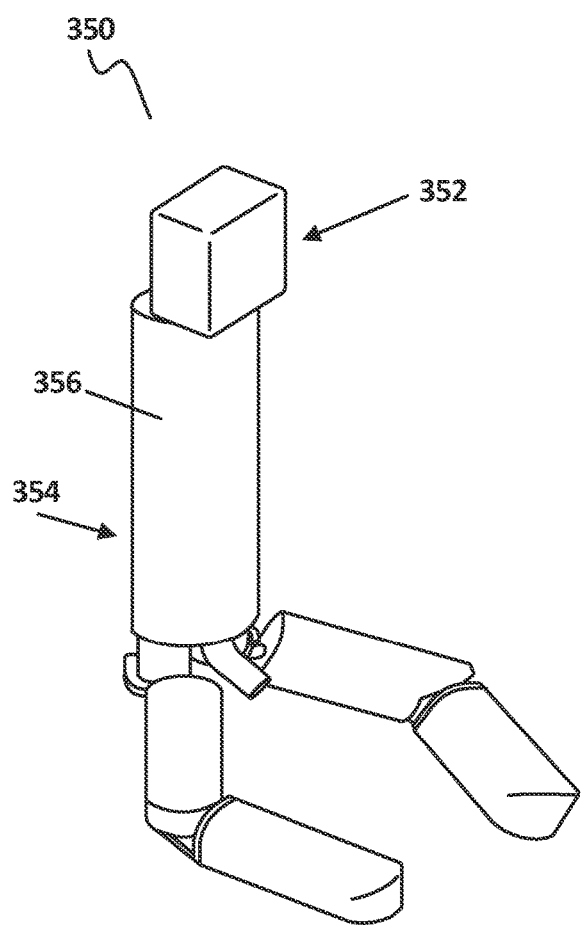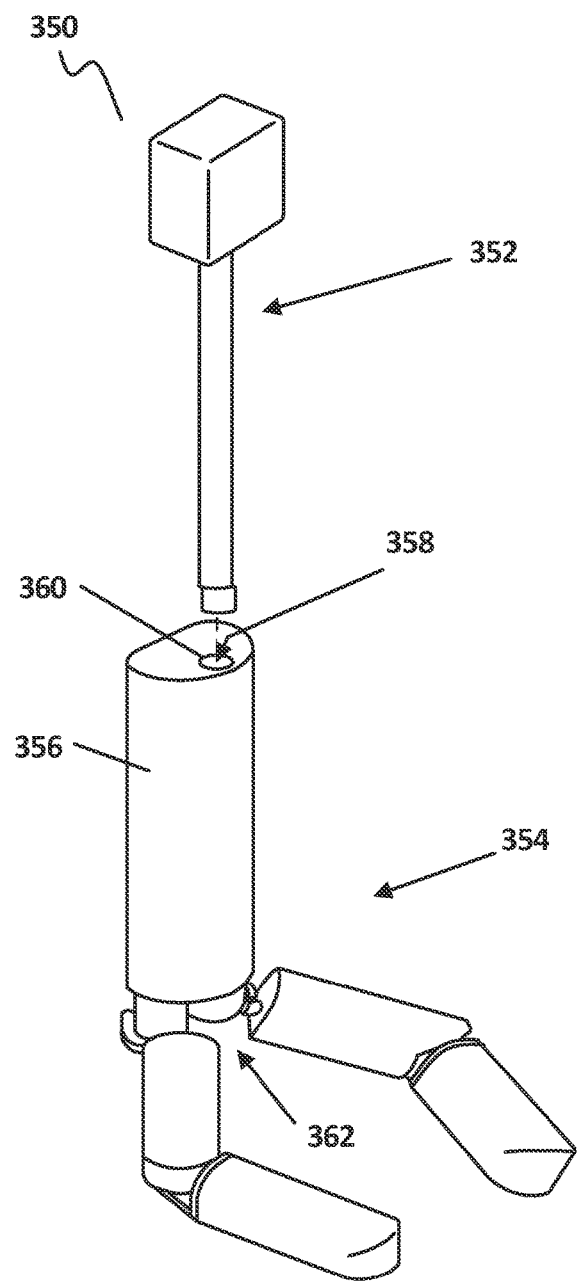
FIG. 18A
FIG. 18B

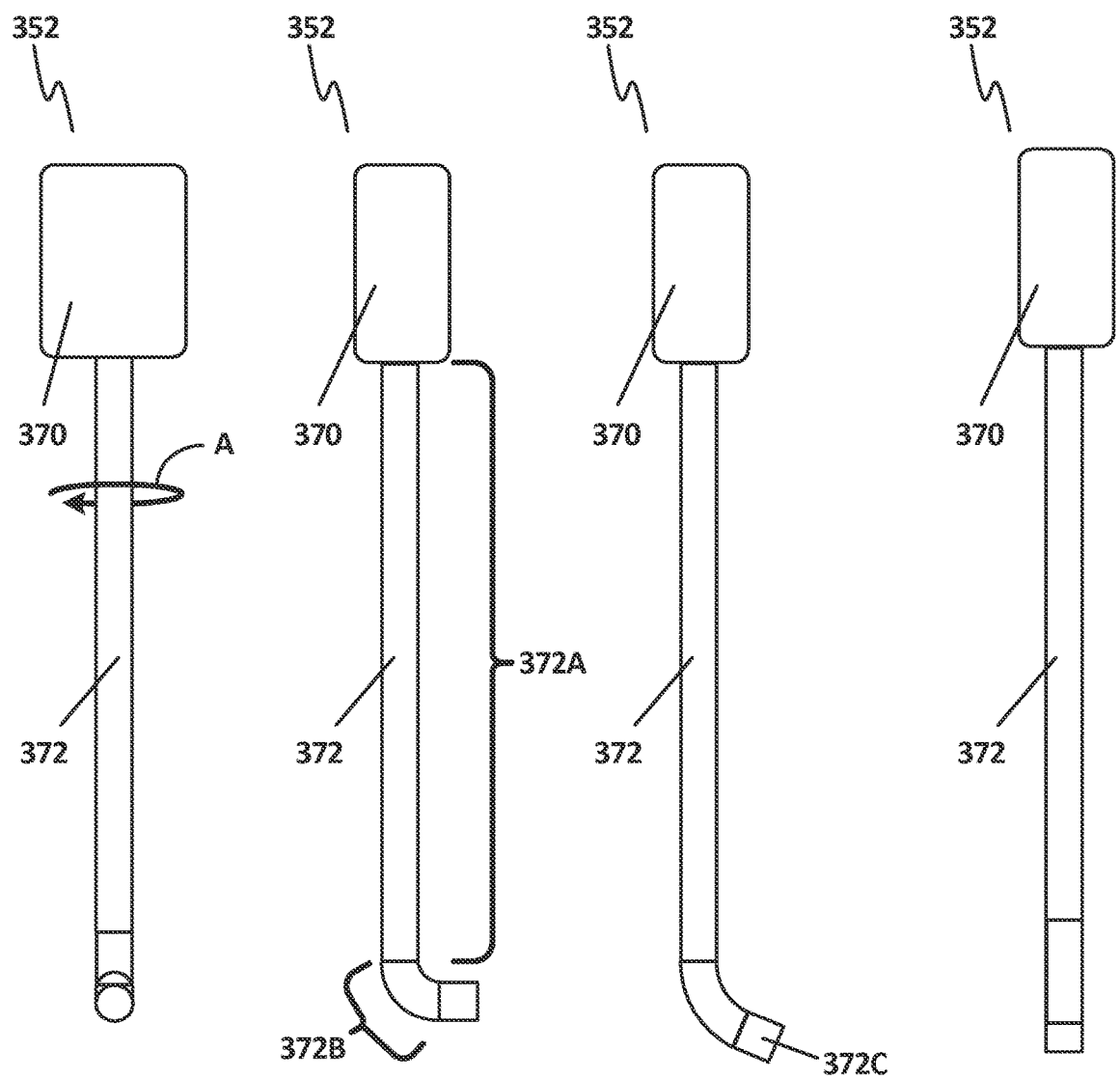

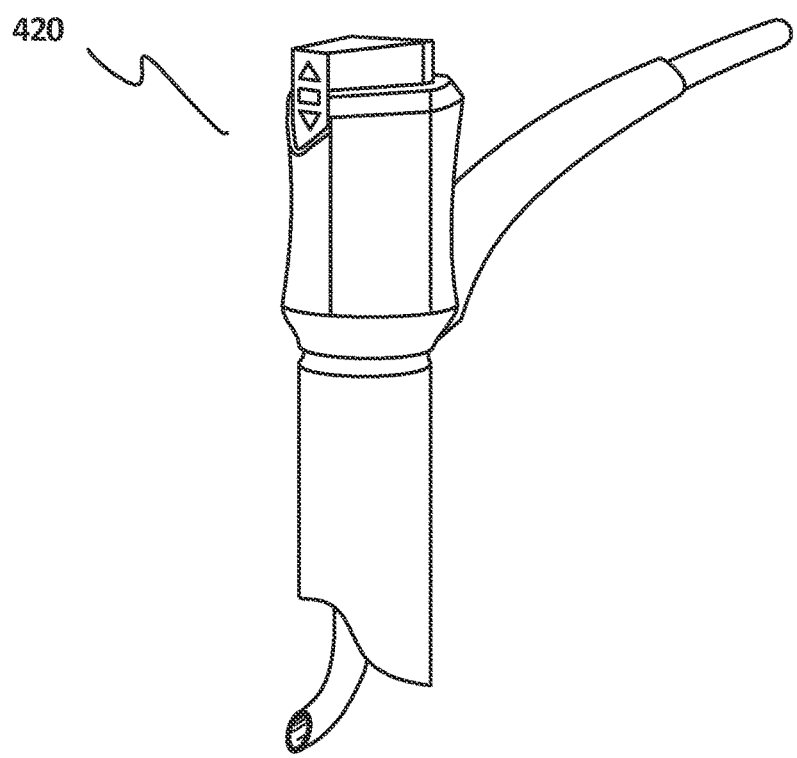
FIG. 20A
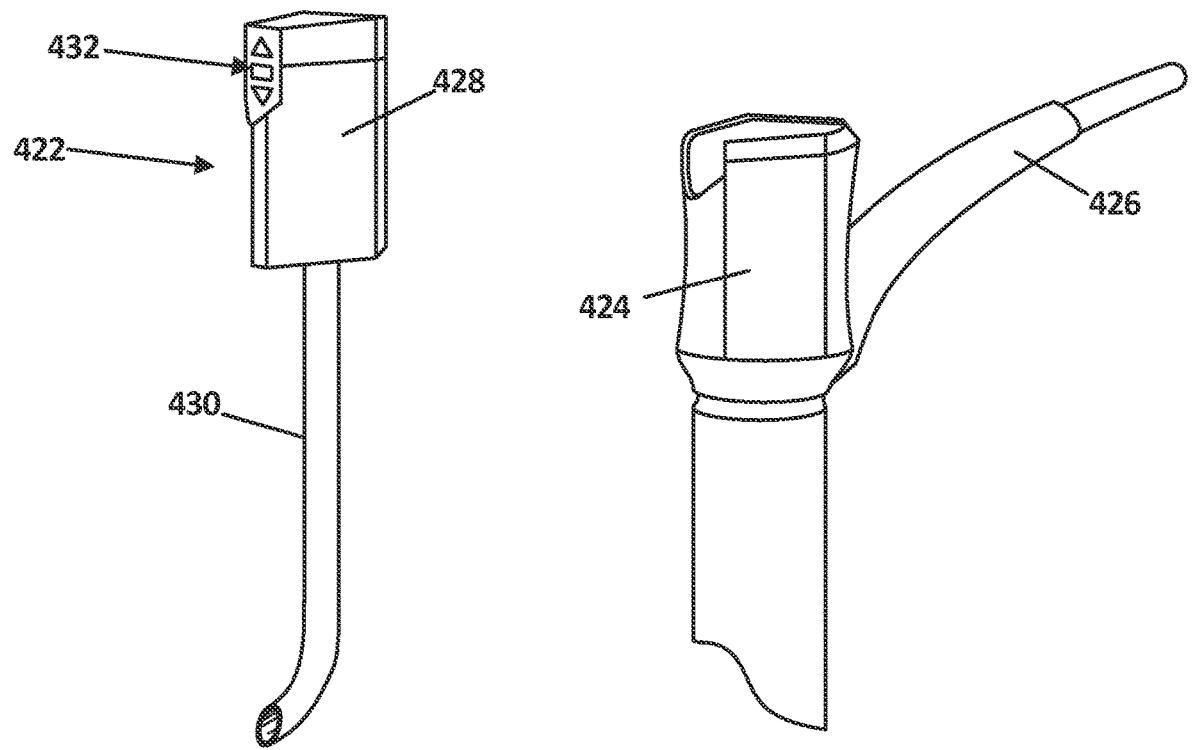
FIG. 20B
FIG. 20C

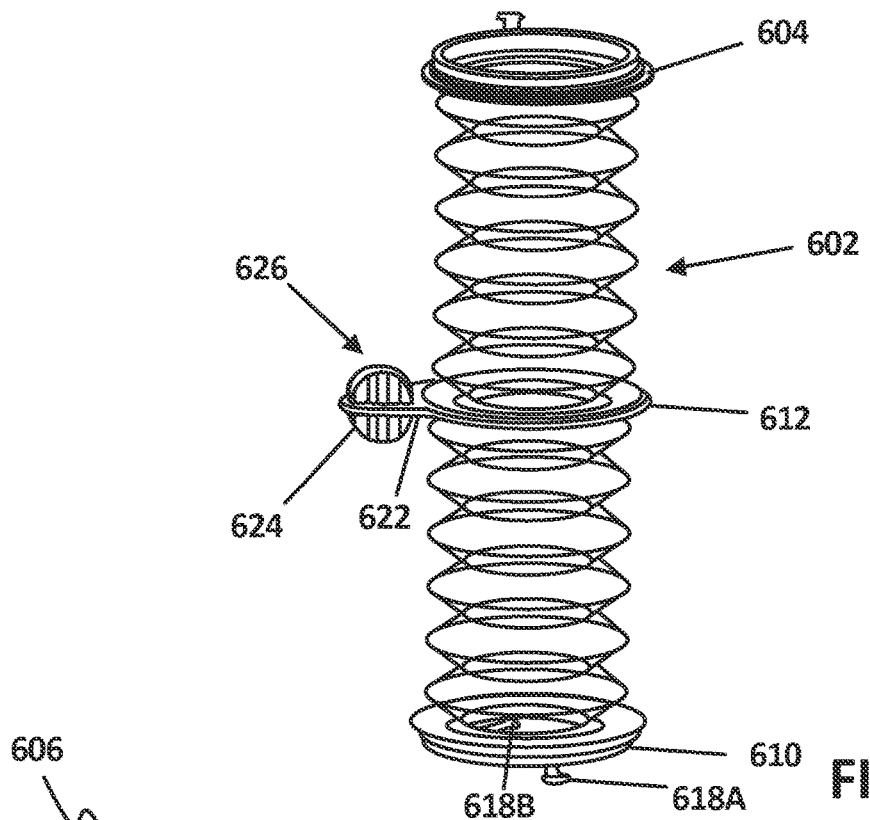
FIG. 30B
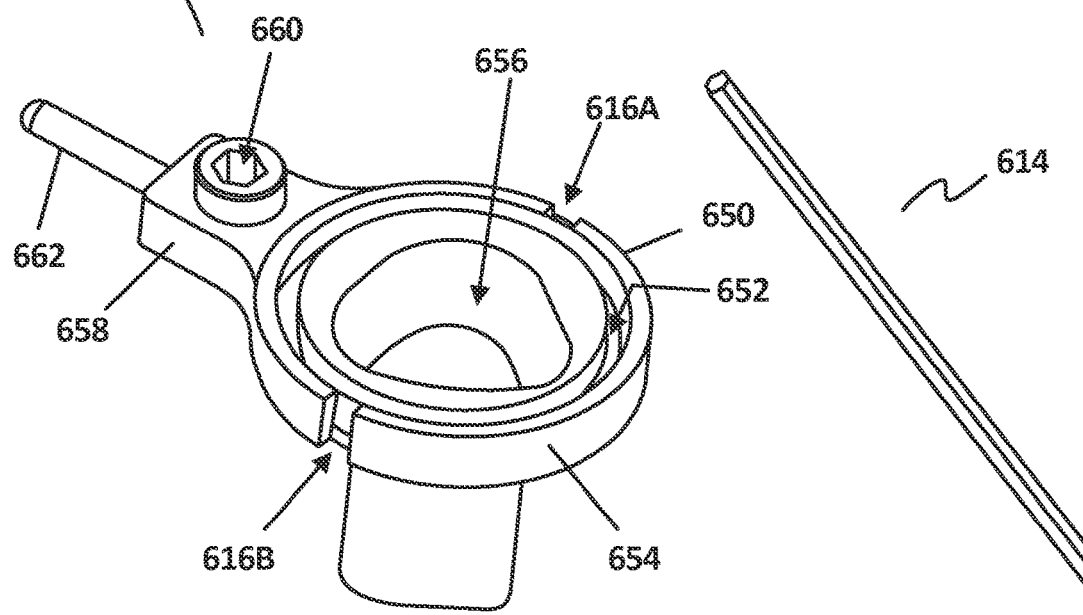
FIG. 30C
FIG. 30D

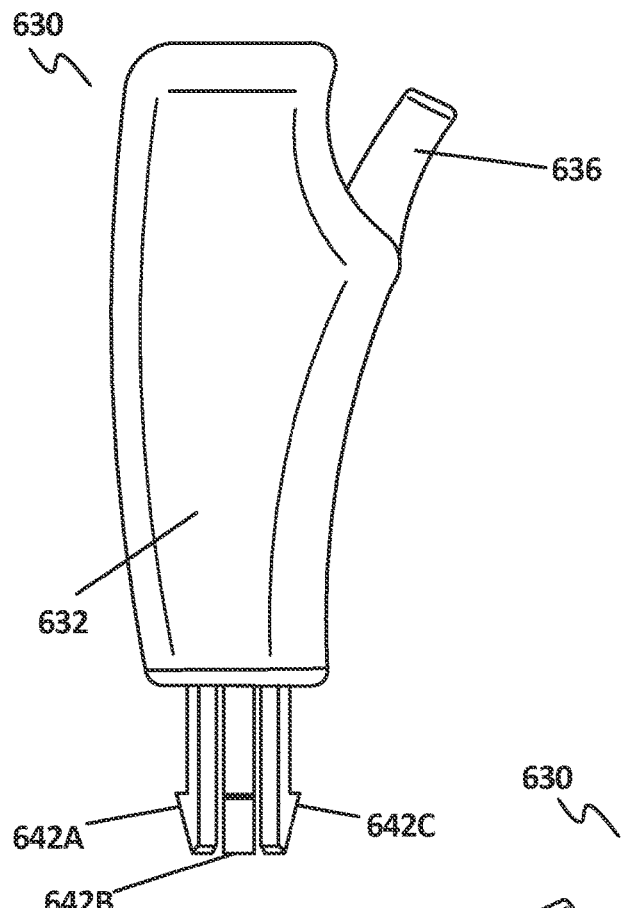
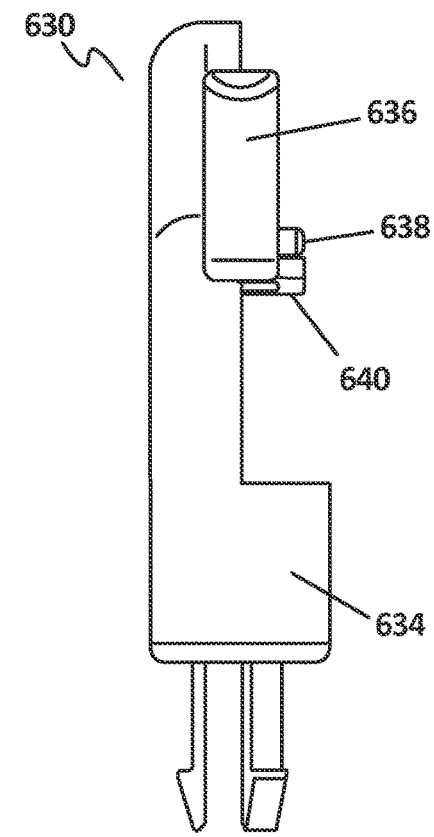
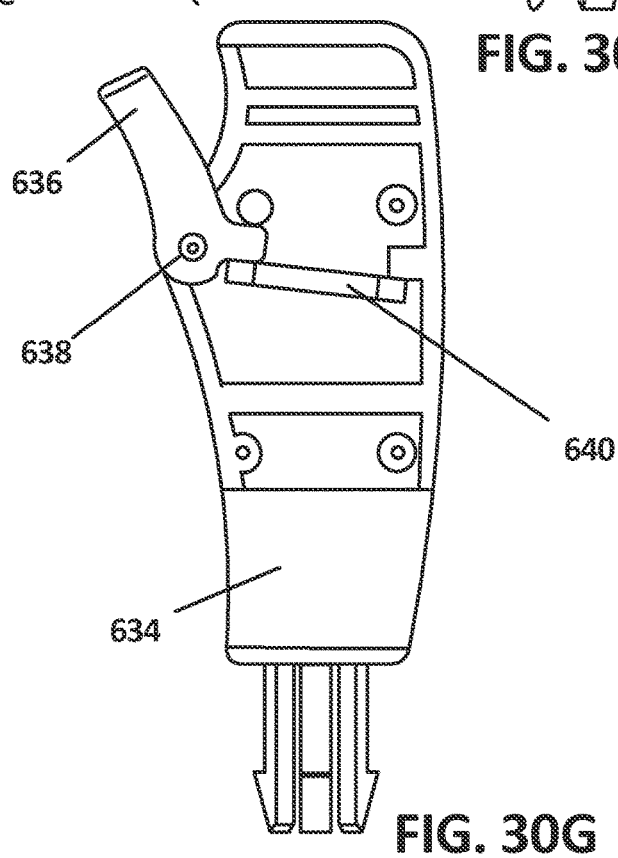

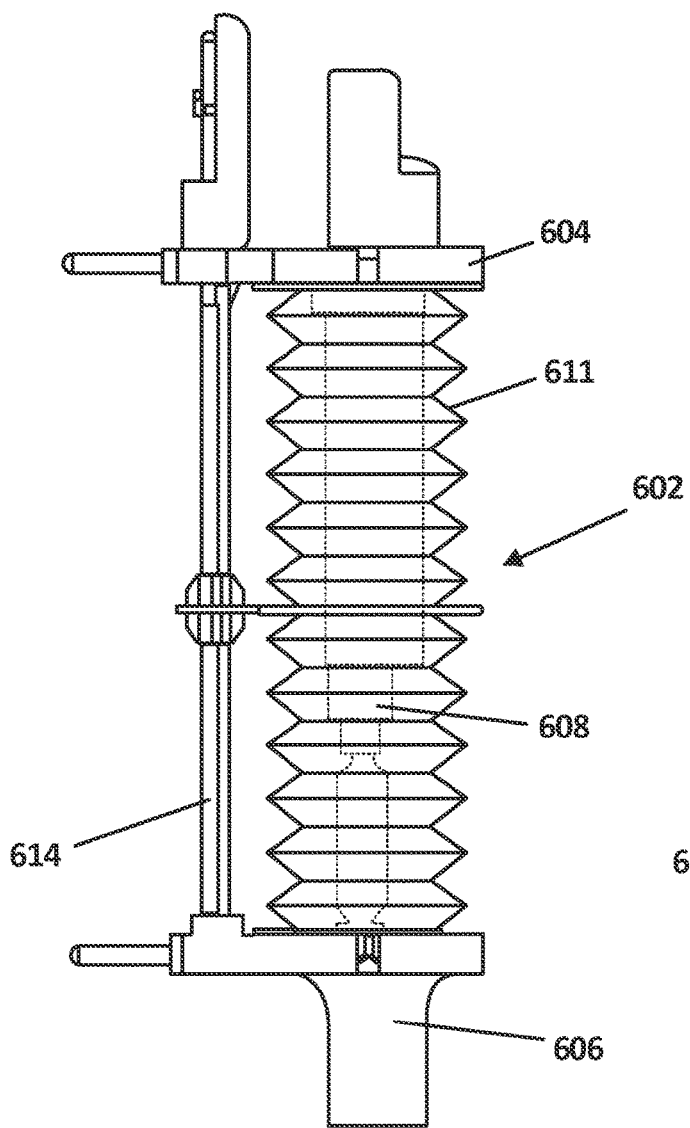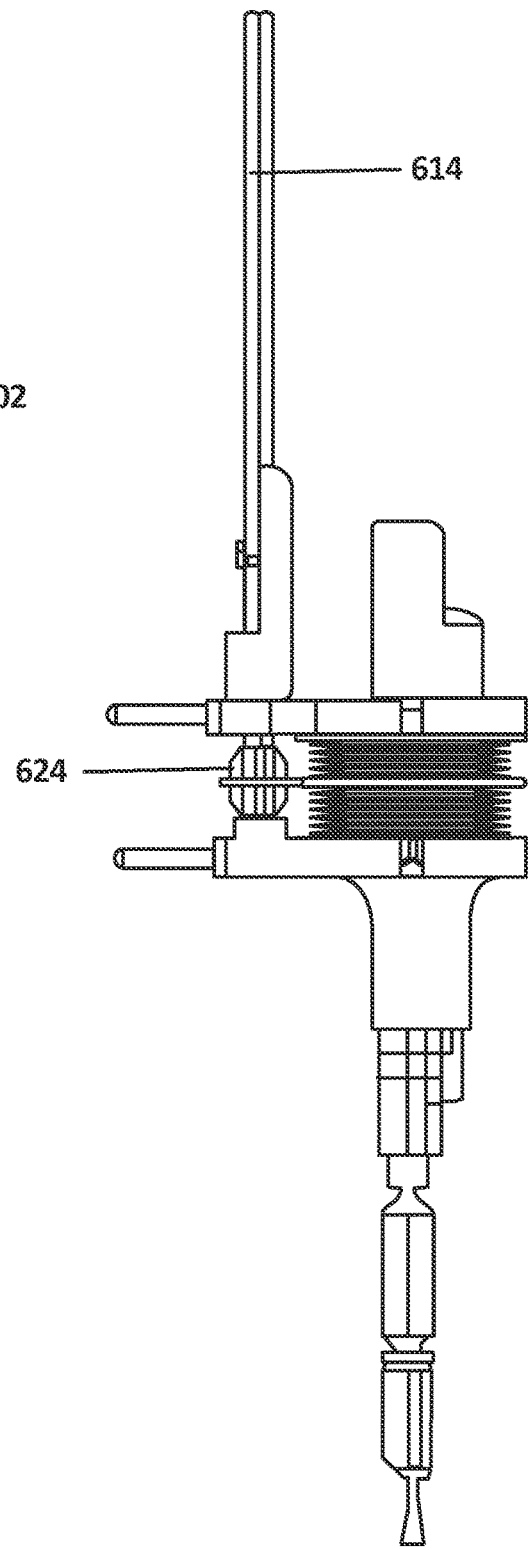
FIG. 31A
FIG. 31B

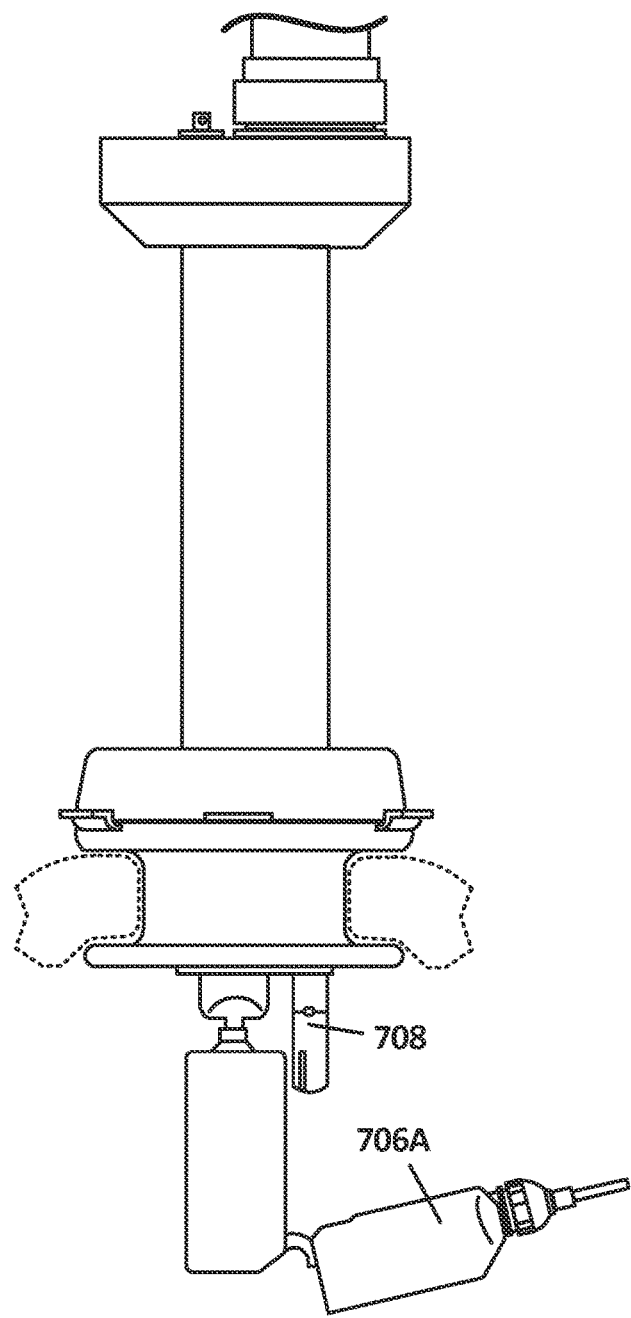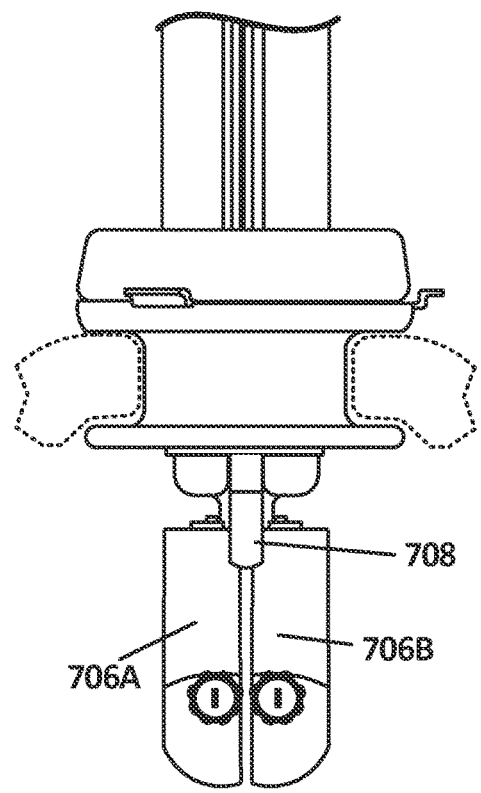
FIG. 34A
FIG. 34B

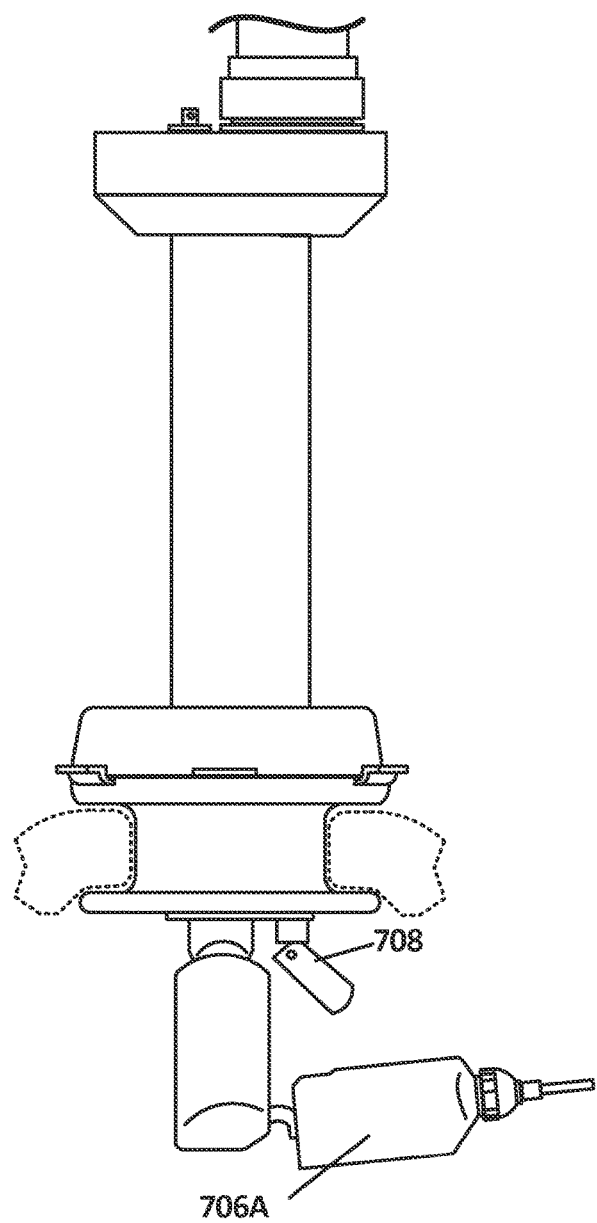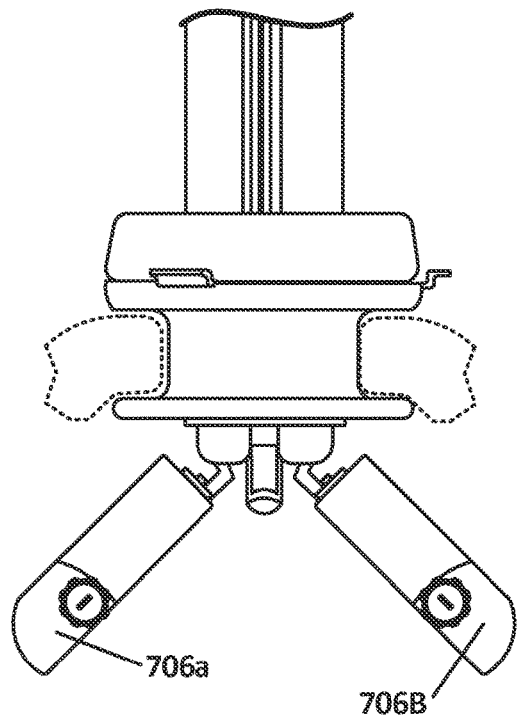
FIG. 35A
FIG. 35B

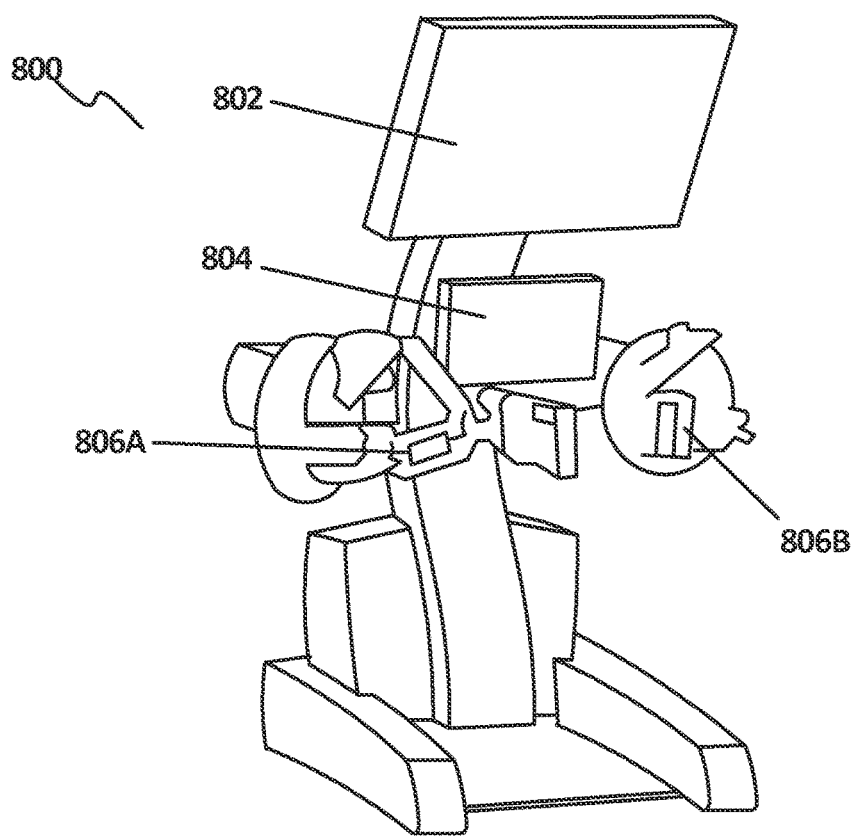
FIG. 37A
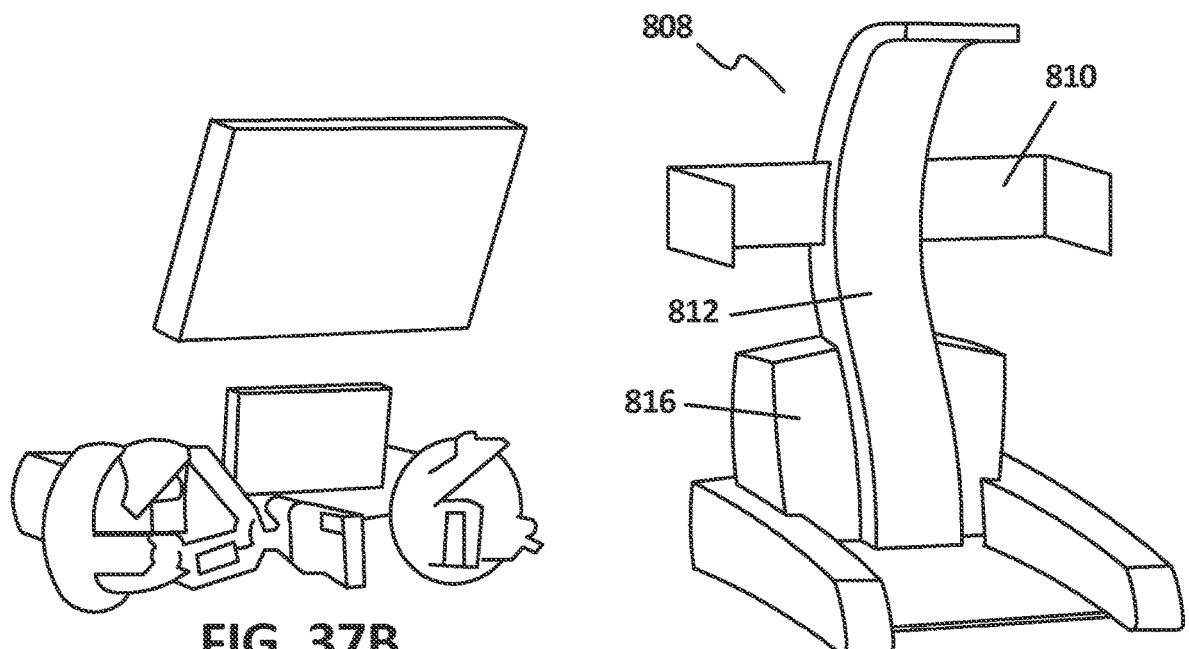
FIG. 37B
FIG. 37C

ROBOTIC SURGICAL DEVICES, SYSTEMS AND RELATED METHODS

CROSS-REFERENCE TO RELATED APPLICATION(S)

This application claims the benefit under 35 U.S.C. § 119(e) to U.S. Provisional Application 61/847,394, filed Jul. 17, 2013 and entitled Robotic Surgical Devices, Systems, and Related Methods, which is hereby incorporated herein by reference in its entirety.

TECHNICAL FIELD

The embodiments disclosed herein relate to various medical devices and related components, including robotic and/or in vivo medical devices and related components. Certain embodiments include various robotic medical devices, including robotic devices that are disposed within a body cavity and positioned using a support component disposed through an orifice or opening in the body cavity. Further embodiment relate to methods and devices for operating the above devices.

BACKGROUND

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

BRIEF SUMMARY OF THE INVENTION

Discussed herein are various robotic surgical systems, including certain systems having camera lumens configured to receive various camera systems. Further embodiments relate to surgical insertion devices configured to be used to insert various surgical devices into a cavity of a patient while maintaining insufflations of the cavity.

In Example 1, a robotic surgical system comprises a device body, first and second shoulder joints operably coupled to the distal end of the device body, a first robotic arm operably coupled to the first shoulder joint, a second robotic arm operably coupled to the second shoulder joint, and a camera component. The device body comprises a distal end, a proximal end, and a camera lumen defined within the device body such that the camera lumen comprises a proximal lumen opening in the proximal end of the device body and a distal lumen opening in the distal end of the device body. The camera component comprises a controller body and an elongate tube operably coupled to the controller, wherein the elongate tube is configured and sized to be positionable through the camera lumen defined in the device body. The elongate tube comprises a rigid section, an optical section, and a flexible section operably coupling the optical section to the rigid section. Further, the elongate tube has a length such that the optical section is configured to extend distally from the distal lumen opening when the camera component is positioned through the camera lumen.

Example 2 relates to the robotic surgical system according to Example 1, wherein the controller body comprises a controller configured to operate the camera component.

Example 3 relates to the robotic surgical system according to Example 1, wherein the distal lumen opening is positioned between the first and second shoulder joints.

Example 4 relates to the robotic surgical system according to Example 1, wherein the optical section is configured to be tiltable at the flexible section in relation to the rigid section, wherein the optical section has a straight configuration and a tilted configuration.

Example 5 relates to the robotic surgical system according to Example 1, wherein the elongate tube is configured to be rotatable in relation to the controller body.

In Example 6, a robotic surgical system comprises a device body, first and second shoulder joints operably coupled to the distal portion of the device body, a first robotic arm operably coupled to the first shoulder joint, a second robotic arm operably coupled to the second shoulder joint, and a camera system. The device body comprises a receptacle disposed at a proximal portion of the device body and a camera lumen defined within the device body such that the camera lumen comprises a proximal lumen opening in the receptacle and a distal lumen opening defined in a distal portion of the device body. The camera system comprises a system body configured to be mateably positionable within the receptacle and an elongate tube operably coupled to the system body, wherein the elongate tube is configured and sized to be positionable through the camera lumen defined in the device body. The elongate tube has a length such that a portion of the elongate tube is configured to extend distally from the distal lumen opening when the system body is positioned within the receptacle.

Example 7 relates to the robotic surgical system according to Example 6, wherein the elongate tube further comprises a substantially rigid section, an optical section, and a flexible section operably coupling the optical section to the rigid section. The optical section is configured to be tiltable at the flexible section in relation to the rigid section, wherein the optical section has a straight configuration and a tilted configuration.

Example 8 relates to the robotic surgical system according to Example 6, wherein the distal lumen opening is positioned between the first and second shoulder joints.

Example 9 relates to the robotic surgical system according to Example 6, wherein the elongate tube is configured to be rotatable in relation to the system body.

Example 10 relates to the robotic surgical system according to Example 6, further comprising a positioning rod operably coupled to the device body.

Example 11 relates to the robotic surgical system according to Example 10, wherein the positioning rod further comprises a handle operably coupled to the positioning rod.

In Example 12, a surgical insertion device comprises a collapsible canister defining a lumen, a top cap coupled to a proximal end of the canister, an incision port removably coupled to a distal end of the canister, a support frame operably coupled to the canister at a point along the canister between the top cap and the incision port, and a support rod operably coupled to the top cap, the support frame, and the incision port such that the top cap and the support frame are slidable in relation to the support rod. The canister is sized to receive a surgical device in the lumen. The top cap comprising at least one lumen defined in the top cap. The incision port comprising a fluidic sealing component configured to maintain a fluidic seal between the incision port and the canister. The support frame is configured to support the canister.

Example 13 relates to the surgical insertion device according to Example 12, wherein the device comprises a retracted configuration in which the top cap and support frame are positioned at a maximum distance from the incision port such that the canister is in an uncollapsed state, and a deployed configuration in which the top cap and support frame are positioned at a minimum distance from the incision port such that the canister is in a collapsed state.

Example 14 relates to the surgical insertion device according to Example 13, further comprising a handle operably coupled to the top cap, wherein the handle is configured to be actuable to move the top cap between the retracted and deployed configurations.

Example 15 relates to the surgical insertion device according to Example 13, further comprising a handle comprising a handle body, a lumen defined in the handle body, an actuation lever operably coupled to the handle body, and a coupling component operably coupled to the actuation lever. The lumen is configured to receive the support rod. The actuation lever is configured to be movable between an unactuated configuration and an actuated configuration. The coupling component comprises an opening configured to receive the support rod. Further, the coupling component is configured to be movable between frictional contact with the support rod when the actuation lever is in the unactuated configuration and no contact with the support rod when the actuation lever is in the actuated configuration.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1A is a side view of a robotic surgical device according to one embodiment.
FIG. 1B is perspective front view of the device of FIG. 1.
FIG. 1C is a perspective view of the device of FIG. 1.
FIG. 1D is an end view of the device of FIG. 1.
FIG. 2A is a cutaway view of the interior body and shoulder of the robotic medical device, according to one embodiment.
FIG. 2B is a rotated cutaway view of the robotic medical device of FIG. 2A.
FIG. 4B is a rotated sideview of the embodiment of FIG. 4A.
FIG. 4C is a further rotated sideview of the embodiment of FIG. 4A.
FIG. 4D is an endlong view of the embodiment of FIG. 4A.
FIG. 4E is a further endlong view of the embodiment of FIG. 4A.

FIG. 18A is a perspective view of one embodiment of a surgical device with a removable camera system, according to one embodiment.

FIG. 18B is another perspective view of the device of FIG. 18A, with the camera system removed from the device.

FIG. 18C is a front view of the camera system of FIG. 18A.

FIG. 18D is a side view of the camera system of FIG. 18A in which the camera is in a tilted configuration.

FIG. 18E is a side view of the camera system of FIG. 18A in which the camera is in a position between the tilted and straight configurations.

FIG. 18F is a side view of the camera system of FIG. 18A in which the camera is in the straight configuration.

FIG. 20A is a perspective view of a surgical device with a removable camera system, according to yet another embodiment.

FIG. 20B is a perspective view of the camera system of the device of FIG. 20A.

FIG. 20C is a perspective view of certain components of the device of FIG. 20A.

FIG. 30B is a perspective view of the canister of the external pressurized insertion system of FIG. 30A.

FIG. 30C is a perspective view of the port of the system of FIG. 30A.

FIG. 30D is a perspective view of the support rod of the system of FIG. 30A.

FIG. 30E is a side view of the handle of the system of FIG. 30A.

FIG. 30F is a front view of the handle of the system of FIG. 30A.

FIG. 30G is another side view of the handle of the system of FIG. 30A.

FIG. 31A is a side view of the system of FIG. 30A in its retracted configuration.

FIG. 31B is a side view of the system of FIG. 30A in its deployed configuration.

FIG. 34A is a side view of the system of FIG. 30A in which the camera has been advanced out of the lumen and the arms of the surgical device have been bent at the elbows.

FIG. 34B is a front view of the system as shown in FIG. 34A.

FIG. 35A is a side view of the system of FIG. 30A in which the camera has been tilted and the arms have been spread FIG. 35B is a front view of the system as shown in FIG. 35A.

FIG. 37A is a perspective view of a console that can be used with any of the surgical device embodiments disclosed herein, according to one embodiment.

FIG. 37B is a perspective view of some of the components of the console of FIG. 37A.

FIG. 37C is a perspective view of the frame of the console of FIG. 37A.

DETAILED DESCRIPTION

Figure 2C:
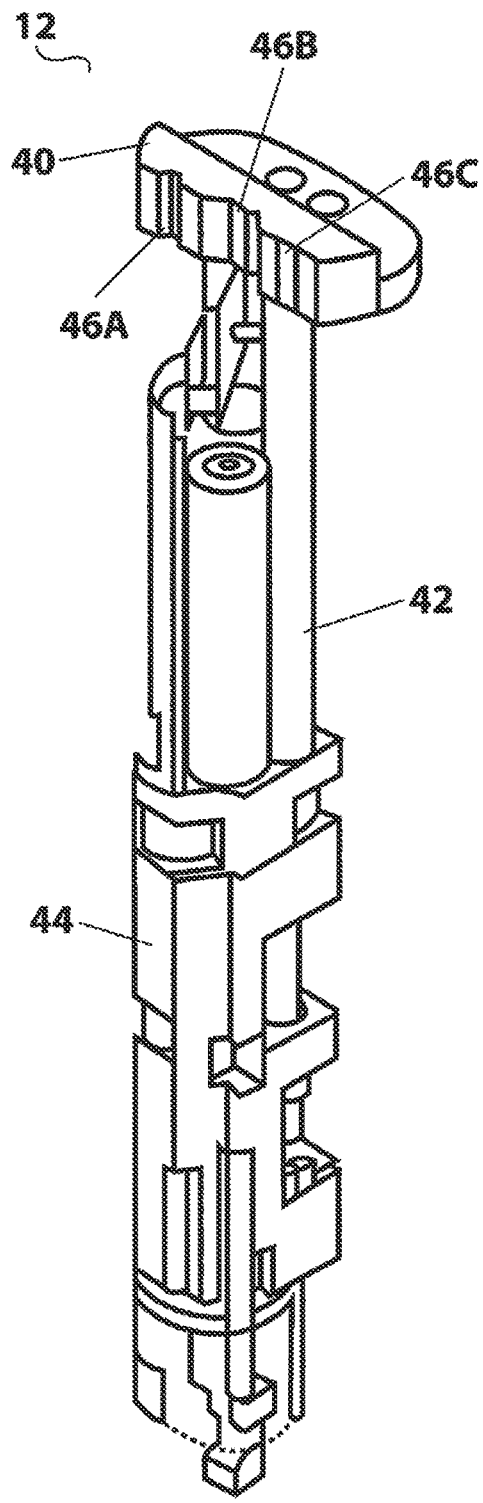
FIG. 2C is a perspective cutaway view of the medical device, according to the embodiment of FIG. 2A.

The various systems and devices disclosed herein relate to devices for use in medical procedures and systems. More specifically, various embodiments relate to various medical devices, including robotic devices and related methods and systems.

It is understood that the various embodiments of robotic devices and related methods and systems disclosed herein can be incorporated into or used with any other known medical devices, systems, and methods.

It is understood that the various embodiments of robotic devices and related methods and systems disclosed herein can be incorporated into or used with any other known medical devices, systems, and methods. For example, the various embodiments disclosed herein may be incorporated into or used with any of the medical devices and systems disclosed in copending U.S. application Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), 61/030,588 (filed on Feb. 22, 2008), Ser. No. 12/171,413 (filed on Jul. 11, 2008 and entitled "Methods and Systems of Actuation in Robotic Devices"), Ser. No. 12/192,663 (filed Aug. 15, 2008 and entitled Medical Inflation, Attachment, and Delivery Devices and Related Methods"), Ser. No. 12/192,779 (filed on Aug. 15, 2008 and entitled "Modular and Cooperative Medical Devices and Related Systems and Methods"), Ser. No. 12/324,364 (filed Nov. 26, 2008 and entitled "Multifunctional Operational Component for Robotic Devices"), 61/640,879 (filed on May 1, 2012), U.S. Ser. No. 13/493,725 (filed Jun. 11, 2012 and entitled "Methods, Systems, and Devices Relating to Surgical End Effectors"), Ser. No. 13/546,831 (filed Jul. 11, 2012 and entitled "Robotic Surgical Devices, Systems, and Related Methods"), 61/680,809 (filed Aug. 8, 2012), Ser. No. 13/573,849 (filed Oct. 9, 2012 and entitled "Robotic Surgical Devices, Systems, and Related Methods"), U.S. Ser. No. 13/738,706 (filed Jan. 10, 2013 and entitled "Methods, Systems, and Devices for Surgical Access and Insertion"), Ser. No. 13/833,605 (filed Mar. 15, 2013 and entitled "Robotic Surgical Devices, Systems, and Related Methods"), Ser. No. 13/839,422 (filed Mar. 15, 2013 and entitled "Single Site Robotic Devices and Related Systems and Methods"), U.S. Ser. No. 13/834,792 (filed Mar. 15, 2013 and entitled "Local Control Robotic Surgical Devices and Related Methods"), Ser. No. 14/208,515 (filed Mar. 13, 2014 and entitled "Methods, Systems, and Devices Relating to Robotic Surgical Devices, End Effectors, and Controllers"), Ser. No. 14/210,934 (filed Mar. 14, 2014 and entitled "Methods, Systems, and Devices Relating to Force Control Surgical Systems), and Ser. No. 14/212,686 (filed Mar. 14, 2014 and entitled "Robotic Surgical Devices, Systems, and Related Methods"), and U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued May 15, 2011, and entitled "Robotic Devices with Agent Delivery Components and Related Methods"), all of which are hereby incorporated herein by reference in their entireties.

Certain device and system implementations disclosed in the applications listed above can be positioned within a body cavity of a patient in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

As shown in FIGS. 1A, 1B, 1C, and 1D, certain exemplary embodiments relate to a device 10 having a body 12 with two arms 14A, 14B operably coupled thereto. The body 12 as shown has a casing 30. The body 12 is also referred to as a "device body." Each arm 14A, 14B has a first coupling link 16A, 16B that couples the arm 14A, 14B to the body 12. This first coupling link 16A, 16B can also be referred to herein as a "first coupling component" or "shoulder link" and is part of the first rotatable joint 24A, 24B (also referred to herein as the "shoulder joint"). Each arm 14A, 14B has an upper arm (also referred to herein as an "inner arm," "inner arm assembly," "inner link," "inner link assembly," "upper arm assembly," "first link," or "first link assembly") 18A, 18B, and a forearm (also referred to herein as an "outer arm," "outer arm assembly," "outer link," "outer link assembly," "forearm assembly," "second link," or "second link assembly") 20A, 20B. The upper arms 18A, 18B are rotatably coupled to the coupling links 16A, 16B, which are rotatably coupled to the body 12. Each arm 14A, 14B has a second coupling link 22A, 22B that couples the upper arm 18A, 18B to the forearm 20A, 20B. This second coupling link 22A, 22B can also be referred to herein as a "second coupling component" or "elbow link" and is part of the second rotatable joint 26A, 26B (also referred to herein as the "elbow joint"). More specifically, in the right arm 14A, the upper arm 18A is rotatably coupled to the forearm 20A at the elbow joint 26A via the elbow link 22A, while in the left arm 14B, the upper arm 18B is rotatably coupled to the forearm 20B at the elbow joint 26B via elbow link 22B.

As shown, each of the arms 14A, 14B also has an end effector 28A, 28B operably coupled to the distal end of the forearm 20A, 20B. An end effector can also be referred to herein as an "operational component."

In one implementation, each of the arms 14A, 14B has six degrees of freedom. That is, as explained in further detail below, each arm 14A, 14B has three degrees of freedom at the shoulder, one degree of freedom at the elbow, and two degrees of freedom at the end effector (which can be rotated—end effector roll—and opened/closed). As such, the six degrees of freedom of each arm 14A, 14B are analogous to the degrees of freedom of a human arm, which also has three degrees of freedom at the shoulder and one at the elbow. One advantage of an arm having four degrees of freedom (with an end effector having two degrees of freedom) is that the end effector can have multiple orientations at the same Cartesian point. This added dexterity allows the surgeon or other user more freedom and a more intuitive sense of control while operating the device.

FIGS. 2A, 2B, 2C, 2D, and 2E according to one embodiment, depict the internal components of the body 12, which is shown in these figures without its casing 30. More specifically, these figures depict the right half of the body 12 and the internal components that control/actuate the right arm 14A. It is understood that the internal components in the left half (not shown) that operate/control/actuate the left arm 14B are substantially the same as those depicted and described herein and that the descriptions provided below apply equally to those components as well.

FIGS. 2A, 2B, and 2C include the internal structural or support components of the body 12. In one implementation, the body 12 has an internal top cap 40, an internal support rod 42, and an internal support shell 44 as shown. The support rod 42 couples the top cap 40 to the support shell 44. These components maintain the structure of the body 12 and provide structural support for the components disposed therein. According to one embodiment, the internal top cap 40 defines three partial lumens 46A, 46B, 46C as best shown in FIG. 2C. The top cap 40 couples to the body casing 30 such that each of the partial lumens 46A, 46B, 46C is formed into a full lumen defined by the coupling of the cap 40 and casing 30. As will be described in further detail below, these lumens 46A, 46B, 46C can be configured to receive various wires, cords, or other components to be inserted into or through the body 12.

In contrast to FIGS. 2A-2C, FIG. 2D depicts the internal actuation and control components of the right half of the body 12 with the internal structural or support components hidden in order to better display the internal actuation and control components. These internal actuation and control components are configured to provide two degrees of freedom at the shoulder joint 24A.

Figure 2D:
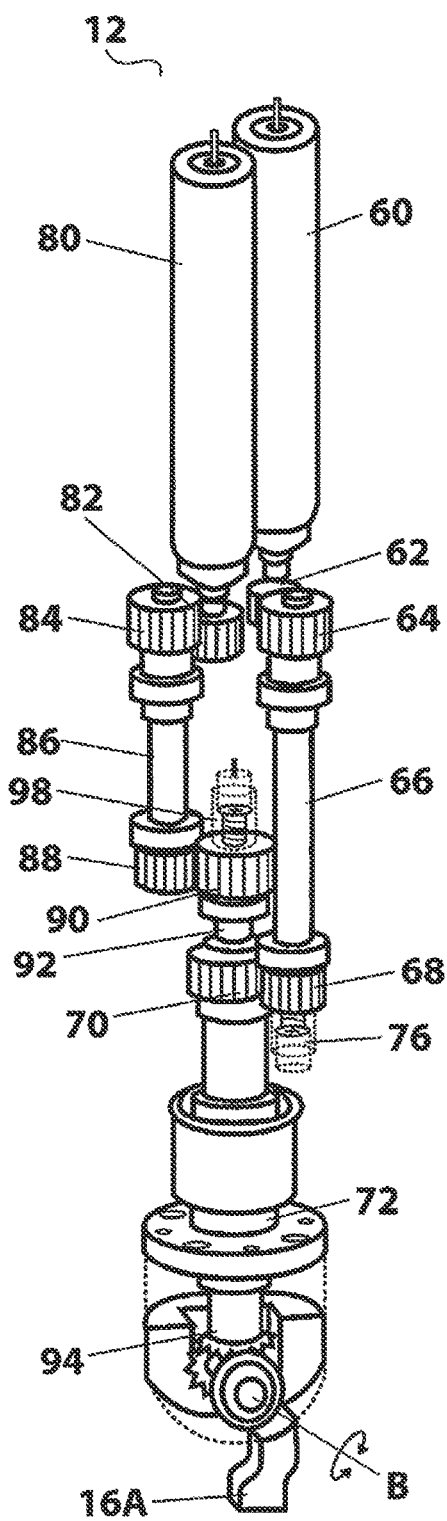
FIG. 2D is a further cutaway perspective view of the medical device body, according to the embodiment of FIG. 2A.
Figure 2E:
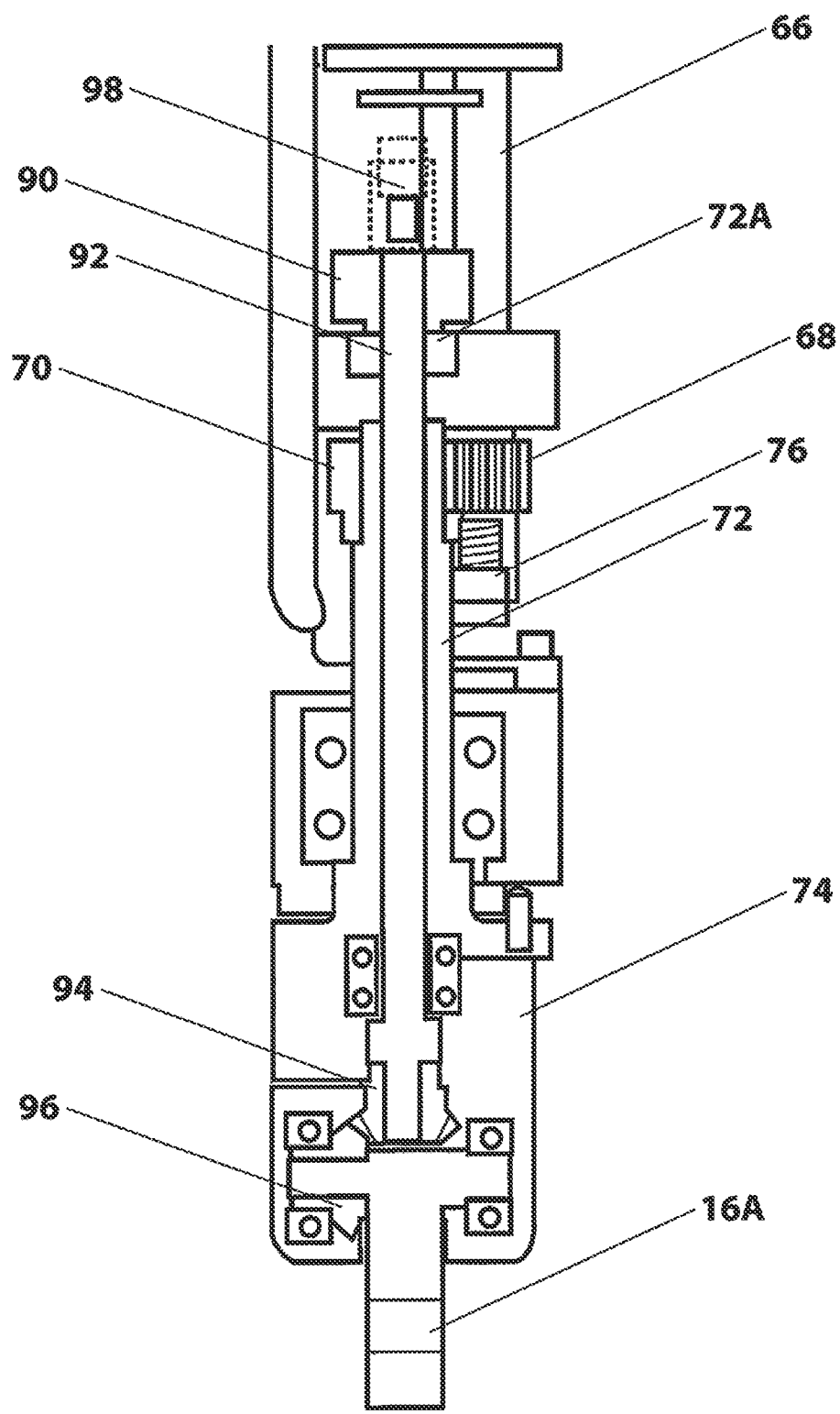
FIG. 2E is a cutaway view of the lower body and shoulder of a robotic device, according to the embodiment of FIG. 2A.

FIG. 2E is an enlarged view of the distal end of the body 12.

In one embodiment, certain of the internal components depicted in FIGS. 2D and 2E are configured to actuate rotation at the shoulder joint 24A around axis A (as best shown in FIG. 2B), which is parallel to the longitudinal axis of the body 12. This rotation around axis A is also referred to as "yaw" or "shoulder yaw." The rotation, in one aspect, is created as follows. An actuator 60 is provided that is, in this implementation, a motor assembly 60. The motor assembly 60 is operably coupled to the motor gear 62, which is coupled to the driven gear 64 such that rotation of the motor gear 62 causes rotation of the driven gear 64. The driven gear 64 is fixedly coupled to a transmission shaft 66, which has a transmission gear 68 at the opposite end of the shaft 66. The transmission gear 68 is coupled to a driven gear 70, which is fixedly coupled to the shaft 72. A magnet holder 76 containing a magnet is also operably coupled to the transmission gear 68. The holder 76 and magnet are operably coupled to a magnetic encoder (not shown). It is understood that the magnet holder 76, magnet, and magnetic encoder (and those similar components as discussed elsewhere herein in relation to other joints) are components of an absolute position sensor that is the same as or substantially similar to one or more of the absolute position sensors disclosed in U.S. Provisional Application 61/680,809, filed on Aug. 8, 2012, which is hereby incorporated herein by reference in its entirety. The shaft 72 is fixedly coupled at its distal end to a rotatable pitch housing 74 (as best shown in FIGS. 2B and 2E) such that rotation of the driven gear 70 causes rotation of the shaft 72 and thus rotation of the housing 74 around axis A as shown in FIG. 2B.

According to one implementation, certain other internal components depicted in FIG. 2D are configured to actuate rotation at the shoulder joint 24A around axis B (as best shown in FIG. 2D), which is perpendicular to the longitudinal axis of the body 12. This rotation around axis B is also referred to as "pitch" or "shoulder pitch." The rotation, in one embodiment, is created as follows. An actuator 80 is provided that is, in this implementation, a motor assembly 80. The motor assembly 80 is operably coupled to the motor gear 82, which is coupled to the driven gear 84 such that rotation of the motor gear 82 causes rotation of the driven gear 84. The driven gear 84 is fixedly coupled to a transmission shaft 86, which has a transmission gear 88 at the opposite end of the shaft 86. The transmission gear 88 is coupled to a driven gear 90, which is fixedly coupled to the shaft 92. A magnet holder 98 containing a magnet is also operably coupled to the driven gear 90. The holder 98 and magnet are operably coupled to a magnetic encoder (not shown). As best shown in FIG. 2E, a portion of the shaft 92 is disposed within the lumen 72A of the shaft 72 described above and extends out of the distal end of the shaft 72 into the housing 74. As best shown in FIG. 2E, the distal end of the shaft 92 is coupled to a rotation gear 94 that is a bevel gear 94. The rotation gear 94 is operably coupled to link gear 96, which is also a bevel gear 96 according to one implementation. The link gear 96 is operably coupled to the shoulder link 16A (discussed above) such that rotation of the shaft 92 causes rotation of the rotation gear 94 and thereby the rotation of the link gear 96 and thus rotation of the link 16A around axis B as best shown in FIG. 2D.

In this embodiment, these two axes of rotation are coupled. That is, if solely rotation around axis A (pure yaw) is desired, then the "pitch drive train" (the motor 80 and all coupled gears and components required to achieve rotation around axis B) must match the speed of the "yaw drive train" (the motor 60 and all coupled gears and components required to achieve rotation around axis A) such that there is no relative angular displacement between the pitch housing 74 and the rotation gear 94. In contrast, if solely rotation around axis B (pure pitch) is desired, then the yaw drive train must hold position while the pitch drive train is actuated.

In one implementation as shown in FIG. 2A, the body 12 has a rigid-flex PCB 100 positioned in the body. The PCB 100 is operably coupled to and controls the motors 60, 80 and magnetic encoders (not shown).

According to another embodiment, at least one connection component is associated with the body 12. More specifically, in this implementation, a power/communication line 102 and a cautery power line 104 are coupled at their proximal ends to one or more external power sources (not shown) and extend into the device 10 through one or more of the three lumens 46A, 46B, 46C defined partially by internal top cap 40. The lines 102, 104 extend through the body 12 and exit as shown in FIG. 2B and extend to the upper arm segment.

In one embodiment, the body 12 can be coupled at its proximal end to a positioning rod (also referred to as an "insertion rod") (not shown). It is understood that the positioning rod can be any such known component for helping to position the device 10 and/or maintain and stabilize the position of the device 10. According to one implementation, the power/communication line 102 and/or the cautery power line 104 can extend proximally through one or more lumens in the positioning rod.

In one embodiment, any of the motors discussed and depicted herein can be brush or brushless motors. Further, the motors can be, for example, 6 mm, 8 mm, or 10 mm diameter motors. Alternatively, any known size that can be integrated into a medical device can be used. In a further alternative, the actuators can be any known actuators used in medical devices to actuate movement or action of a component. Examples of motors that could be used for the motors described herein include the EC 10 BLDC+GP10A Planetary Gearhead, EC 8 BLDC+GP8A Planetary Gearhead, or EC 6 BLDC+GP6A Planetary Gearhead, all of which are commercially available from Maxon Motors, located in Fall River, Mass.

FIGS. 3A, 3B, 3C, 3D, 3E, 4A, 4B, 4C, 4D, and 4E according to one embodiment, depict the internal components of the right upper arm 18A, which is shown in these figures without its casing. More specifically, these figures depict the right arm 14A and the internal components therein. It is understood that the internal components in the left upper arm 18B are substantially the same as those depicted and described herein and that the descriptions provided below apply equally to those components as well.

FIGS. 3A-3E depict the internal components of the right upper arm 18A, including actuators, drive components, and electronics, with the internal structural or support components hidden in order to better display the internal components. In contrast to FIGS. 3A-3E, FIGS. 4A-4E include both the internal actuator, drive, and electronics components, but also the internal structural or support components of the right upper arm 18A.

Figure 3A:
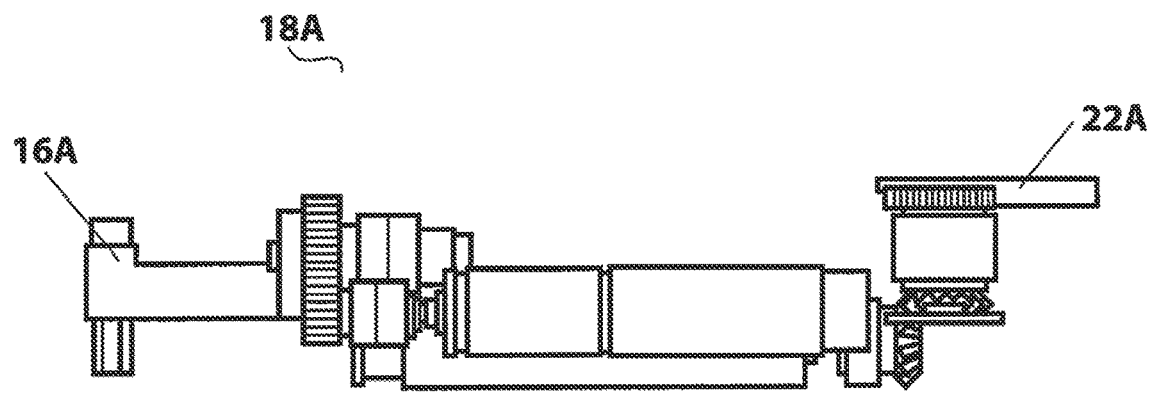
FIG. 3A is a cutaway side view of the upper arm of the robotic medical device, according to one embodiment.
Figure 3B:
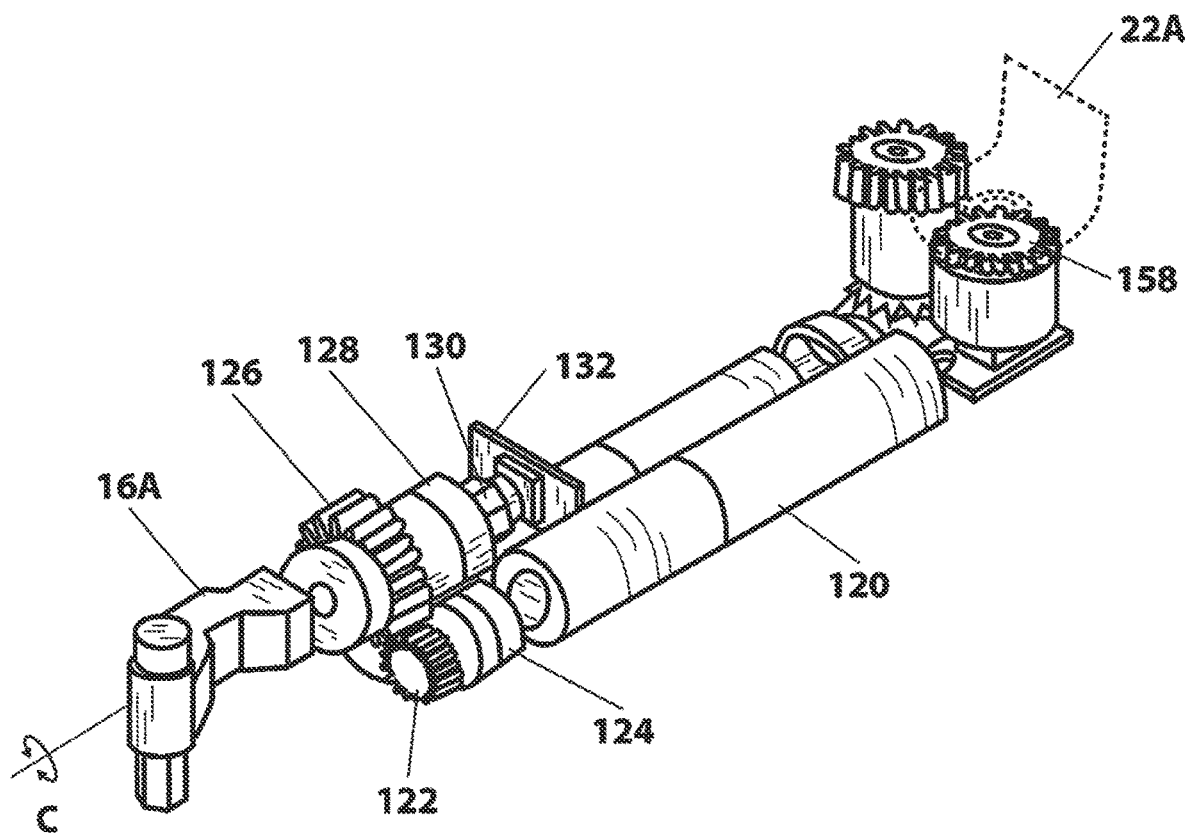
FIG. 3B is a perspective view of the embodiment of FIG. 3A.

In one embodiment, certain of the internal components depicted in FIGS. 3A-3E are configured to actuate rotation at the shoulder link 16A around axis C (as best shown in FIG. 3B), which is parallel to the longitudinal axis of the right upper arm 18A. This rotation around axis C is also referred to as "shoulder roll." The rotation, in one aspect, is created as follows. An actuator 120 is provided that is, in this implementation, a motor assembly 120. The motor assembly 120 is operably coupled to the motor gear 122. The motor gear 122 is supported by a bearing pair 124. The motor gear 122 is coupled to the driven gear 126 such that rotation of the motor gear 122 causes rotation of the driven gear 126. The driven gear 126 is fixedly coupled to the shoulder link 16A such that rotation of the driven gear 126 causes rotation of the shoulder link 16A around axis C as shown in FIG. 3B. The driven gear 126 is supported by a bearing pair 128. A magnet holder 130 containing a magnet is also operably coupled to the driven gear 126. The holder 130 and magnet are operably coupled to a magnetic encoder 132.

The rotation of the shoulder link 16A around axis C causes the right upper arm 18A (and thus the forearm 20A) to rotate in relation to the body 12. According to one embodiment, this rotation adds an additional degree of freedom not provided in prior two-armed surgical devices.

Figure 3C:
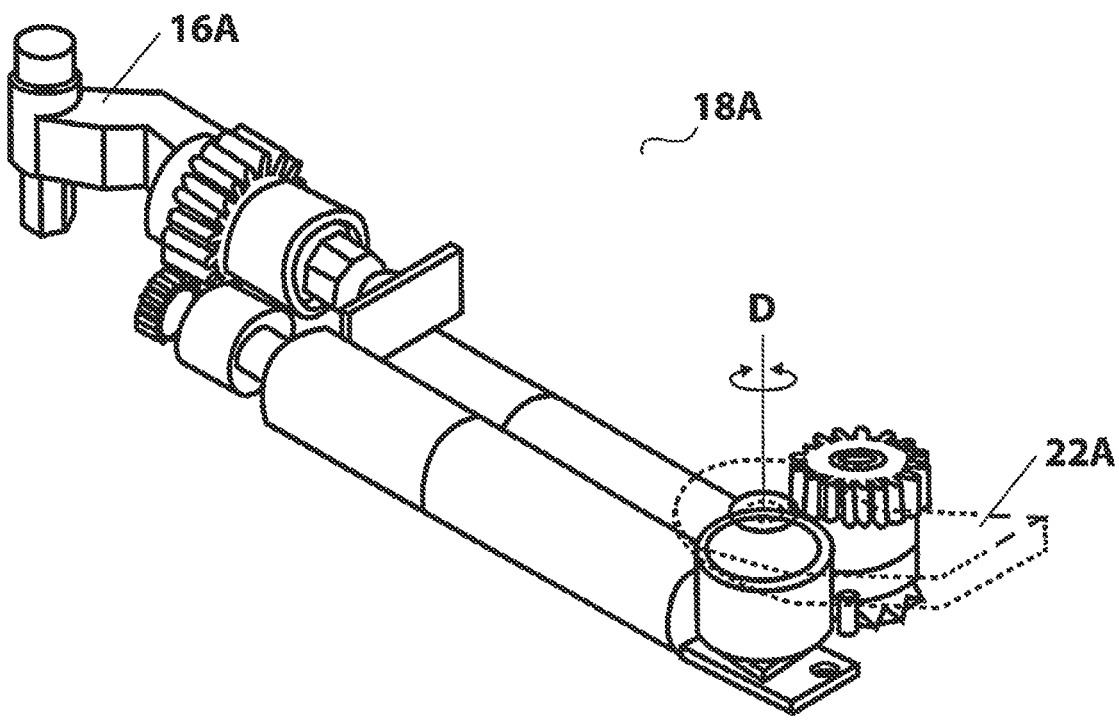
FIG. 3C is a different perspective view of the embodiment of FIG. 3A.
Figure 3D:
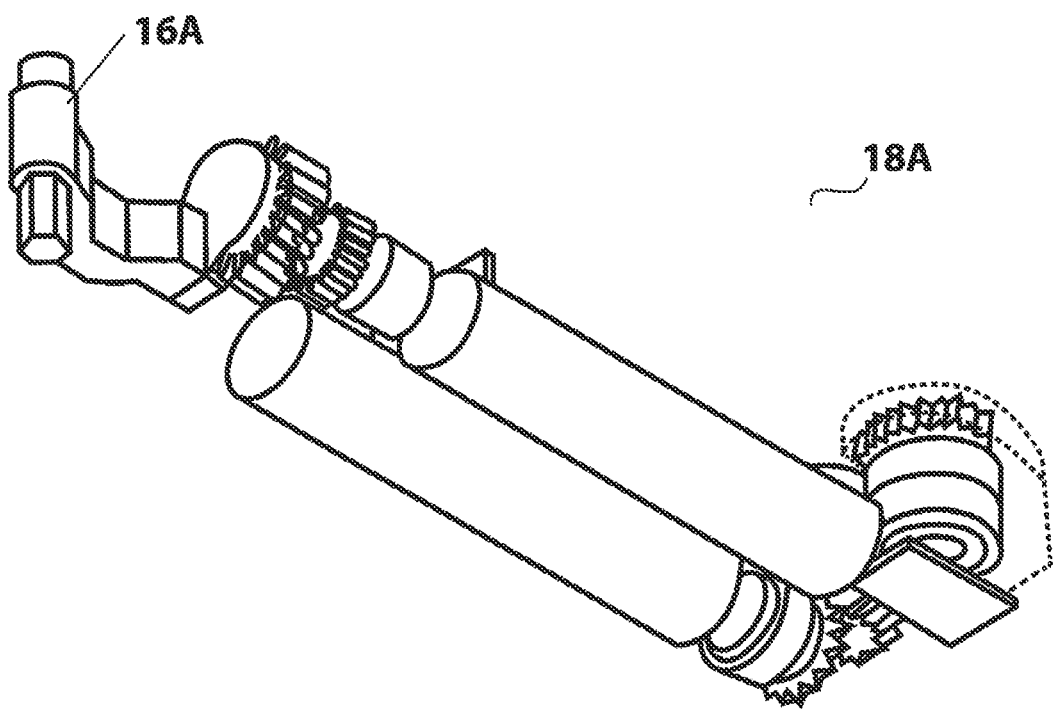
FIG. 3D is a reverse perspective view of the embodiment of FIG. 3A.
Figure 3E:
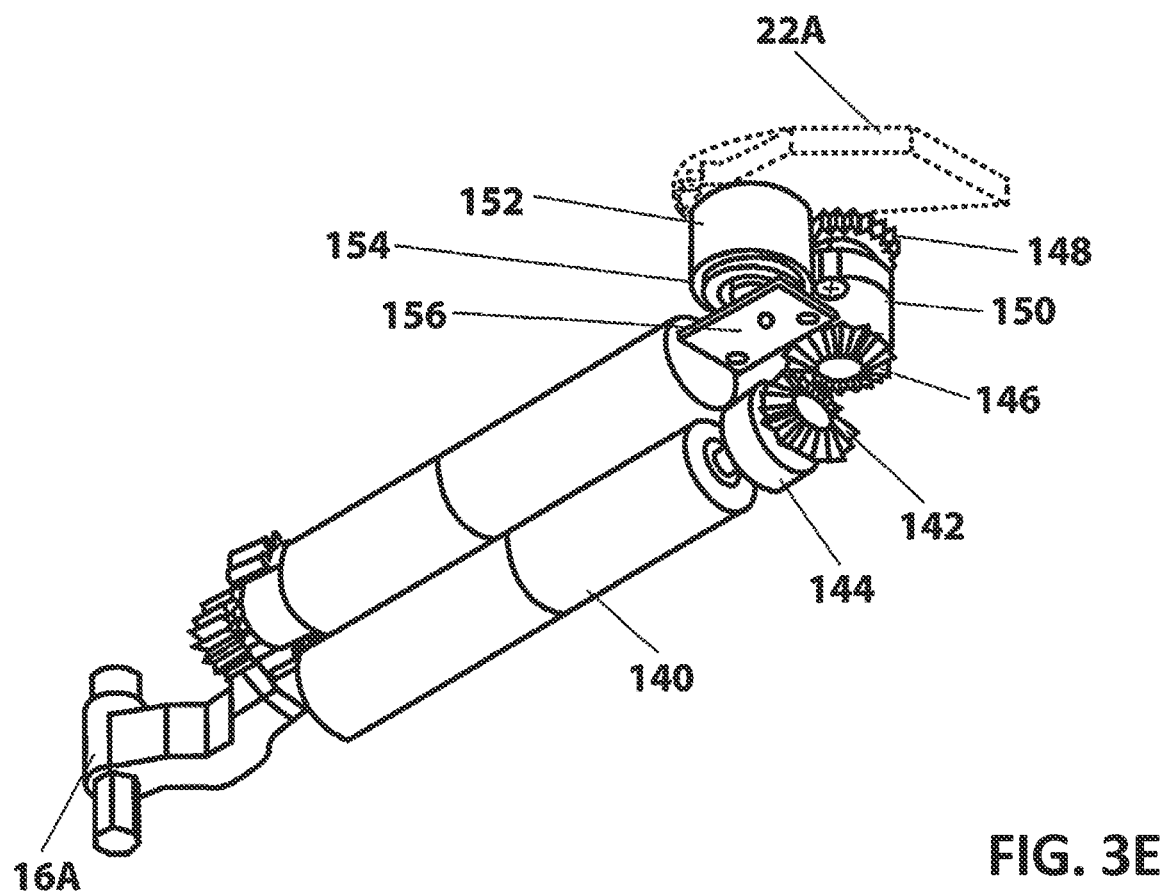
FIG. 3E is an alternate perspective view of medical device as depicted in FIG. 3D.
Figure 4A:
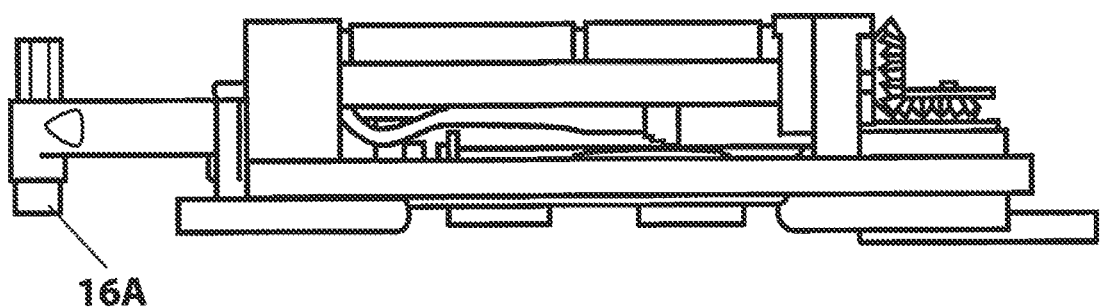
FIG. 4A is a cutaway view of the internal components of the right upper arm of a robotic device, according to one embodiment.

According to one implementation, certain of the internal components depicted in FIGS. 3A-3E are configured to actuate rotation at the elbow link 22A around axis D (as best shown in FIG. 3C), which is perpendicular to the longitudinal axis of the right upper arm 18A. This rotation around axis D is also referred to as "elbow yaw." The rotation, in one aspect, is created as follows. An actuator 140 is provided that is, in this implementation, a motor assembly 140. The motor assembly 140 is operably coupled to the motor gear 142, which is a beveled gear in this embodiment. The motor gear 142 is supported by a bearing 144. The motor gear 142 is coupled to the driven gear 146 such that rotation of the motor gear 142 causes rotation of the driven gear 146. The driven gear 146 is fixedly coupled to a link gear 148, which is coupled to the gear teeth 158 (as best shown in FIG. 3B) of the elbow link 22A such that rotation of the driven gear 146 causes rotation of the elbow link 22A around axis D as shown in FIG. 3C. The driven gear 146 and link gear 148 are supported by a bearing pair 150. Further, the elbow link 22A is supported by a bearing pair 152. A magnet holder 154 containing a magnet is also operably coupled to the elbow link 22A. The holder 154 and magnet are operably coupled to a magnetic encoder 156.

According to one embodiment, the additional coupling of the link gear 148 and the elbow link 22A can provide certain advantages, including an additional external reduction (because the gear 148 has fewer gear teeth than the elbow link 22A) and shortening of the upper arm 18A (thereby improving the joint range of motion).

As shown in FIG. 4B, the upper arm 18A can have a rigid-flex PCB 160 positioned therein. In one embodiment, the PCB 160 is operably coupled to and controls the motors 120, 140 and magnetic encoders 132, 156.

According to another embodiment, at least one connection component is associated with the upper arm 18A. More specifically, in this implementation, the power/communication line 102 and the cautery power line 104 enter through a port (not shown) at the proximal end of the upper arm 18A and exit through a port (not shown) at the distal end.

Figure 5A:
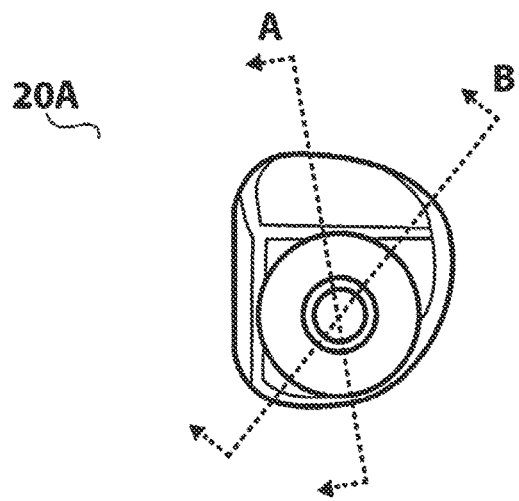
FIG. 5A is a endlong view of the lower arm of a robotic device, according to one embodiment.

FIGS. 5A-9B depict various embodiments of a right forearm 20A. The various implementations disclosed and depicted herein include the actuators, drive components, and electronics that can be used to accomplish both tool roll and tool drive (open/close action), as will be described in further detail below. As set forth below, the forearm 20A also has two electrically isolated cautery circuits, enabling both bipolar and monopolar cautery end effectors. Certain embodiments are configured to allow for easy removal and replacement of an end effector (a "quick change" configuration). Further embodiments contain sealing elements that help to prevent fluid ingress into the mechanism. According to one implementation, certain of the internal components depicted in FIGS. 5A-5C are configured to actuate rotation at the end effector 28A around axis E (as best shown in FIG. 5B), which is parallel to the longitudinal axis of the right forearm 20A. This rotation around axis E is also referred to as "tool roll." The rotation, in one aspect, is created as follows. An actuator 180 is provided that is, in this implementation, a motor assembly 180. The motor assembly 180 is operably coupled to the motor gear 182, which is a spur gear in this embodiment. The motor gear 182 is coupled to the driven gear 184 such that rotation of the motor gear 182 causes rotation of the driven gear 184. The driven gear 184 is fixedly coupled to the roll hub 186, which is supported by a bearing 188. The roll hub 186 is fixedly coupled to the tool base interface 190, which has external threads 190A which are threadably coupled to the end effector 28A. Thus, rotation of the driven gear 184 causes rotation of the roll hub 186, which causes rotation of the tool base interface 190, which causes rotation of the end effector 28A around axis E as shown in FIG. 5B.

Figure 5B:
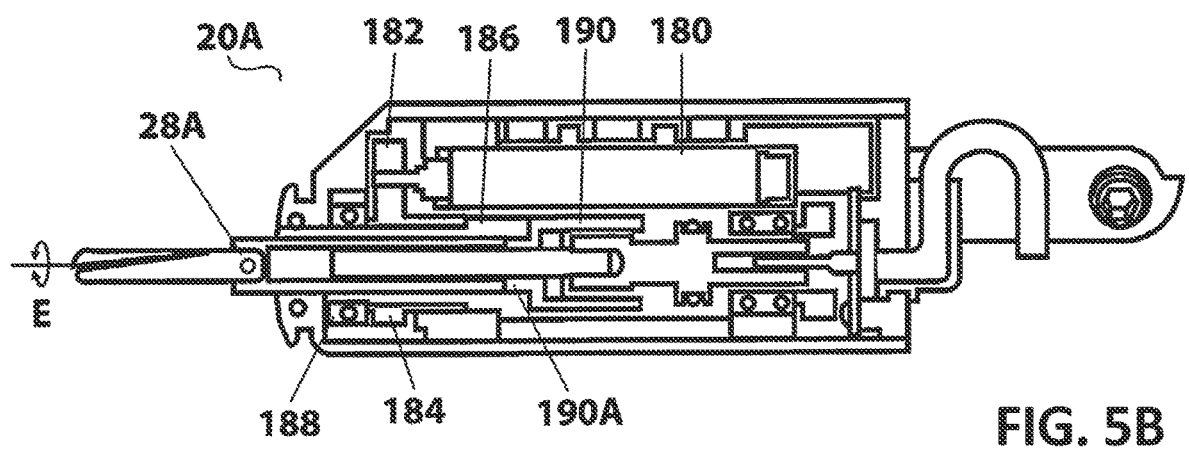
FIG. 5B is cutaway sideview of the internal components of the lower arm of the embodiment of FIG. 5A along line A-A.
Figure 5C:
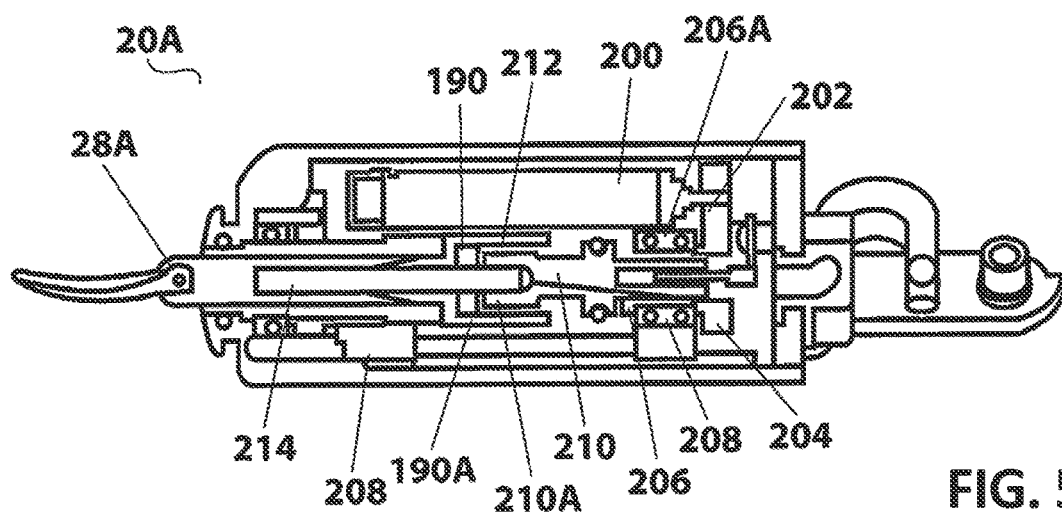
FIG. 5C is cutaway sideview of the internal components of the lower arm of the embodiment of FIG. 5A along line B-B.

In one embodiment, certain of the internal components depicted in FIGS. 5A-5C are configured to actuate the end effector to open and close. This rotation of the end effector arms such that the end effector opens and closes is also called "tool drive." The actuation, in one aspect, is created as follows. An actuator 200 is provided that is, in this implementation, a motor assembly 200. The motor assembly 200 is operably coupled to the motor gear 202, which is a spur gear in this embodiment. The motor gear 202 is coupled to the driven gear 204 such that rotation of the motor gear 202 causes rotation of the driven gear 204. The driven gear 204 is fixedly coupled to a tool drive nut 206, which is supported by bearing pair 208. The tool drive nut 206 has a threaded inner lumen 206A, and this threaded inner lumen 206A is threadably coupled to the lead screw 210. More specifically, the outer threads of the lead screw 210 are threadably coupled to the threads on the inner lumen 206A. The lead screw 210 is rotationally coupled to the tool base interface 190 (discussed above). More specifically, the tool base interface 190 has a square-shaped inner lumen 190A, and the distal end of the lead screw 210 has a square-shaped protrusion that fits within the inner lumen 190A, thereby coupling with the tool base interface 190. The distal end of the lead screw 210 can move translationally within the lumen 190A, but cannot rotate in relation to the tool base interface 190, so the lead screw 210 can move translationally in relation to the tool base interface 190, but cannot rotate in relation thereto. The lead screw 210 also has an insulating sleeve 212 disposed to an external portion of the lead screw 210 and thereby plays a role in maintaining separate electrical cautery channels as will be described below. Further, the lead screw 210 has a threaded inner lumen 210A, which is threadably coupled to the tool pin 214. The tool pin 214 is coupled to a known linkage mechanism within the end effector 28A such that translation of the tool pin 214 causes the grasper arms or blades to open and close. As such, actuation of gear 202 causes rotation of the driven gear 204, which rotates the tool drive nut 206. The rotation of the tool drive nut 206 causes the lead screw 210 to translate as a result of the threadable coupling of the nut 206 and the screw 210. The translation of the screw 210 causes the tool pin 214 to translate, thereby causing the end effector 28A arms or blades to open and close.

In this embodiment, these two axes of rotation are coupled. That is, if pure roll is desired, then the tool drive train must match the speed of the roll train such that there is no relative angular displacement between the tool drive nut 206 and the tool base interface 190.

According to one implementation, the end effector 28A can be quickly and easily coupled to and uncoupled from the forearm 20A in the following fashion. With both the roll and drive axes fixed or held in position, the end effector 28A can be rotated, thereby coupling or uncoupling the threads 190A and 210A. That is, if the end effector 28A is rotated in one direction, the end effector 28A is coupled to the forearm 20A, and if it is rotated in the other direction, the end effector 28A is uncoupled from the forearm 20A.

In accordance with one embodiment, the forearm 20A has two independent cautery channels (referred to herein as "channel A" and "channel B"), which enables the use of either bipolar or monopolar cautery end effectors with this forearm 20A.

Figure 6A:
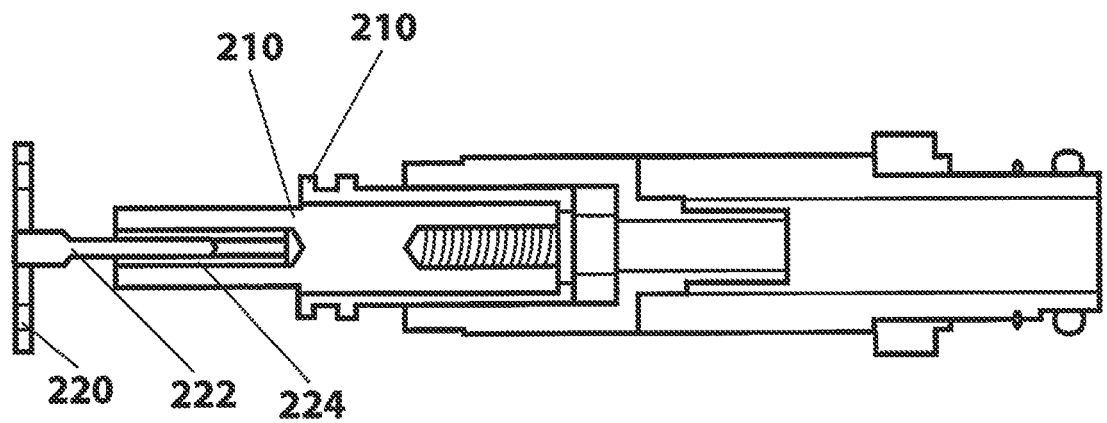
FIG. 6A is a cross-sectional view of the end effector portion of the forearm depicting the electrical portions, according to an exemplary embodiment.

As shown in FIG. 6A, the channel A components are set forth in the forearm 20A as shown. A PCB 220 is electrically coupled to lead A of a cautery power line (such as cautery line 104 discussed above) that is coupled to an external power source. The PCB 220 is further electrically coupled to a pin 222, which is electrically coupled to socket 224 (defined in or coupled—electrically and mechanically—to a proximal end of the lead screw 210 discussed above) and is slidably positioned within the socket 224. The lead screw 210 is coupled electrically and mechanically to the end effector pin 214 as best shown in FIG. 5C. As such, energizing lead A in the cautery line 104 energizes channel A in the bipolar cautery end effector 28A.

Figure 6B:
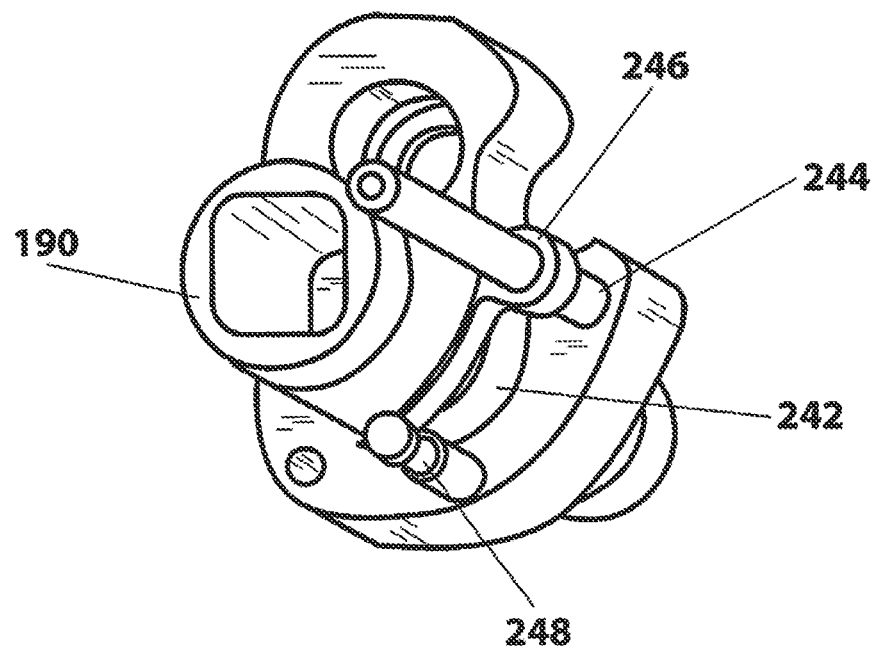
FIG. 6B is a top perspective view of external view of complimentary portion of the forearm to the embodiment of FIG. 6A.
Figure 7:
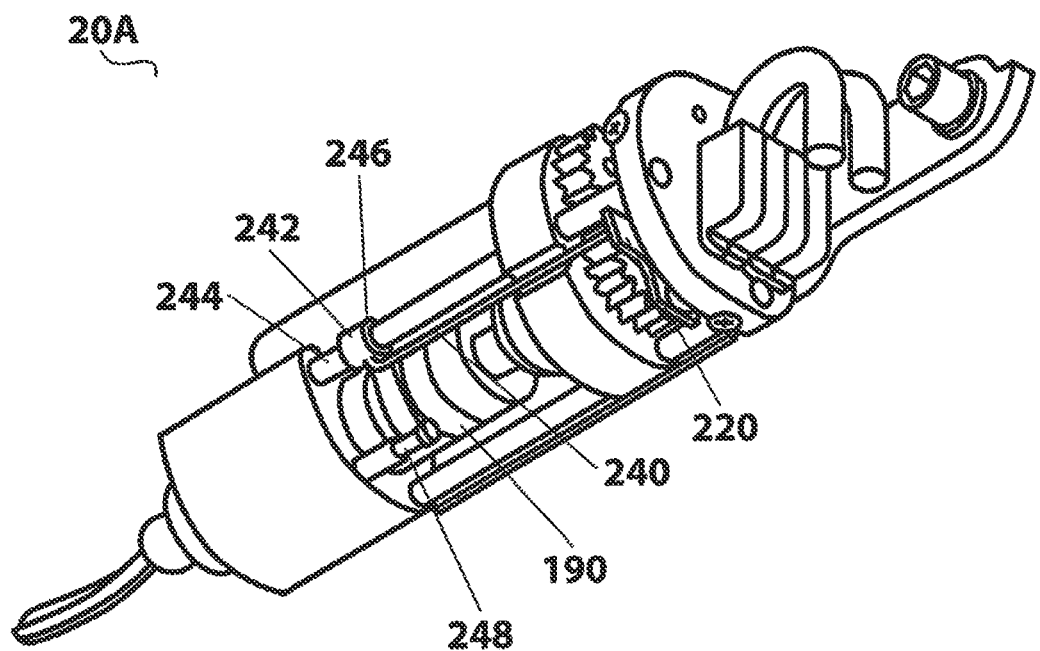
FIG. 7 is a bottom perspective schematic of the internal components of the lower arm of a robotic device, according to one embodiment.

As shown in FIGS. 6B and 7, the channel B components are set forth in the forearm 20A as shown. The PCB 220 discussed above is also electrically coupled to lead B of a cautery power line (such as cautery line 104 discussed above) that is coupled to an external power source. The PCB 220 is further electrically coupled to a conducting rod 240, which is electrically coupled to a wiper 242. The wiper 242 is a tensioned component that supported on one end by a mechanical strut 244. An insulating insert 246 is positioned between the wiper 242 and the mechanical strut 244. At its free end, the wiper 242 is supported by a preloader 248. Based on this configuration, the wiper 242 is loaded or urged (like a leaf spring) against tool base interface 190 (discussed above) and thus is electrically coupled to the tool base interface 190. The tool base interface 190 is mechanically coupled to the end effector 28A and electrically coupled to channel B of that end effector 28A. As such, energizing lead B in the cautery line 104 energizes channel B in the bipolar cautery end effector 28A.

Figure 9A:
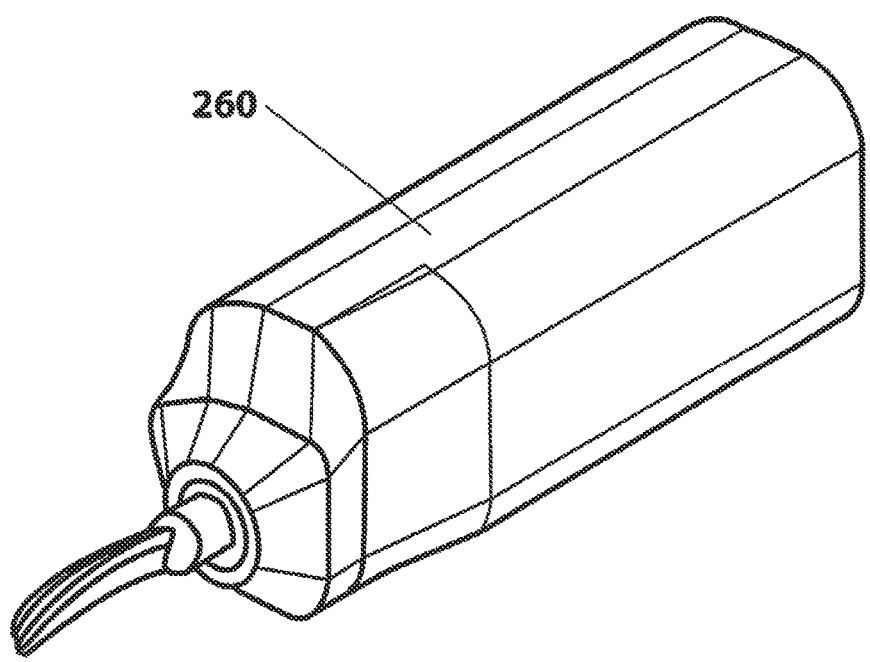
FIG. 9A is a perspective view of the exterior of the forearm according to one embodiment.
Figure 9B:
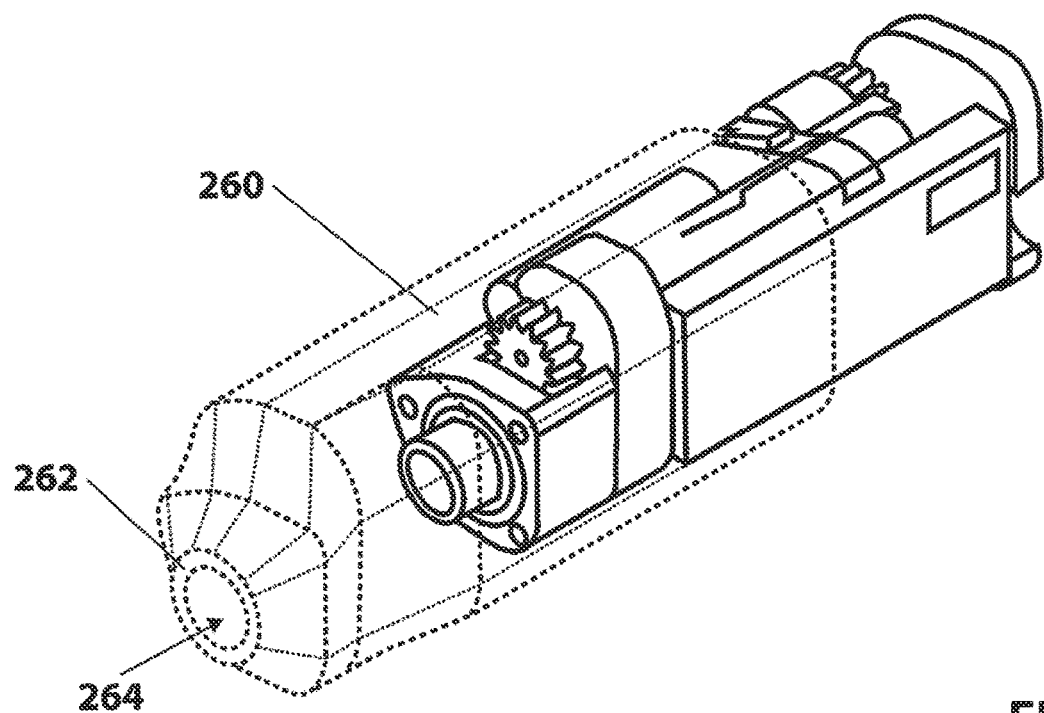
FIG. 9B is an internal view perspective of the embodiment of FIG. 9A

In one implementation, the forearm 20A has at least one fluidic seal interface that helps to prevent fluid ingress into the forearm 20A. One such mechanism is a monolithic single-piece housing 260 as depicted in FIGS. 9A and 9B according to one embodiment. The one-piece nature of the housing 260 greatly reduces the number of interfaces that must be sealed and thus reduces the number of interfaces where fluidic leaks are more likely to occur. The housing 260 is configured to slide over the internal components of the forearm 20A. That is, the proximal end of the housing 260 defines an opening that can be positioned over the forearm 20A (or the forearm 20A is inserted into the lumen) until the housing 260 is correctly positioned over the forearm 20A. As best shown in FIG. 9B, the housing 260 can have an o-ring 262 positioned in a groove defined in the housing 260 around the hole 264 defined in the distal end of the housing 260. The hole 264 is configured to receive the end effector 28A. In one embodiment, the roll hub 186 (discussed above) is positioned through the hole 264 such that the o-ring 262 is configured to be preloaded against that roll hub 186, thereby forming a fluidic seal between the housing 260 and the external surface of the hub 186.

Figure 8A:
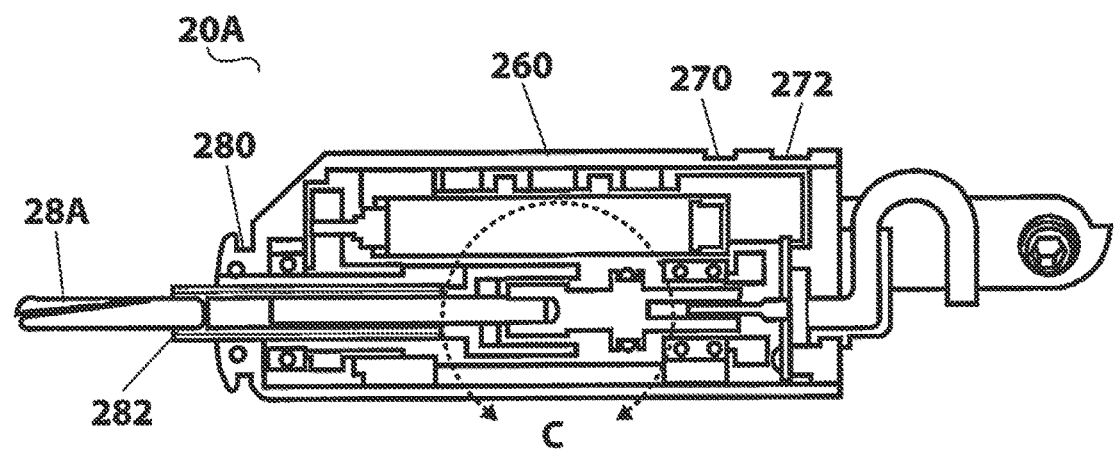
FIG. 8A is cutaway sideview of the internal components of the lower arm of the embodiment of FIG. 5A along line A-A, detailing further electronic components.

In a further embodiment as shown in FIG. 8A, the forearm 20A has two grooves 270, 272 defined in the external portion of the forearm housing 260 (as described above). The grooves 270, 272 can be configured to provide an attachment point for an outer barrier (such as the first barrier 300 described in further detail below) such that an elastic band defined in the opening of the sleeve of the inner barrier 300 can be positioned in the grooves 270, 272, thereby enhancing the coupling of the barrier 300 to the housing 260 and thus enhancing the fluidic seal. In one embodiment, the grooves 270, 272 encircle the entire forearm housing 260. Alternatively, the first barrier 300 can be bonded to the housing 260 via an adhesive or welding. In a further alternative, the housing 260 and the first barrier 300 can be fabricated as a single piece.

According to another implementation as shown in FIG. 8A, the forearm 20A housing 260 can have a groove 280 defined in the housing 260 around the hole 282 in the housing 260 through which the end effector 28A is positioned. The groove 280 can be configured to provide an attachment point for an outer barrier (such as the outer barrier 310 described in further detail below) such that an elastic band defined in the opening of the sleeve of the second barrier 310 can be positioned in the grooves 270, 272, thereby enhancing the coupling of the second barrier 310 to the housing 260 and thus enhancing the fluidic seal.

Figure 8B:
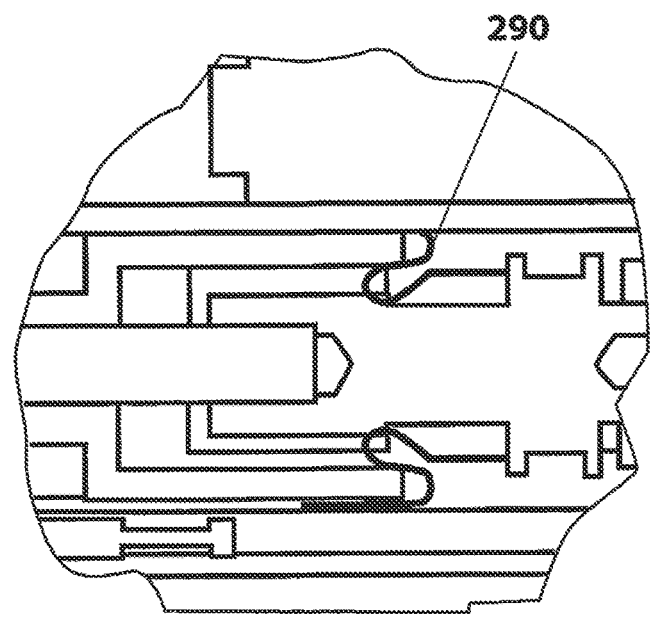
FIG. 8B is a close view of the section C-C of the embodiment of FIG. 8A.

As shown in FIG. 8B, another fluidic seal can be provided according to another embodiment in the form of a flexible membrane 290 that is attached at one end to the lead screw 210 (discussed above) and at the other end to the tool base interface 190 (discussed above). More specifically, the membrane 290 is coupled to the lead screw 210 at the o-ring 292 and is coupled to the tool base interface 190 at the groove 292. In one embodiment, the membrane 290 is retained at the groove 292 with an attachment mechanism such as a cinch (not shown). This membrane 290 serves to provide a fluidic seal for the internal components of the forearm 20A against any external fluids. In one implementation, the seal is maintained whether the end effector 28A is coupled to the forearm 20A or not. Alternatively, the membrane 290 can be replaced with a metallic bellows.

Figure 10A:
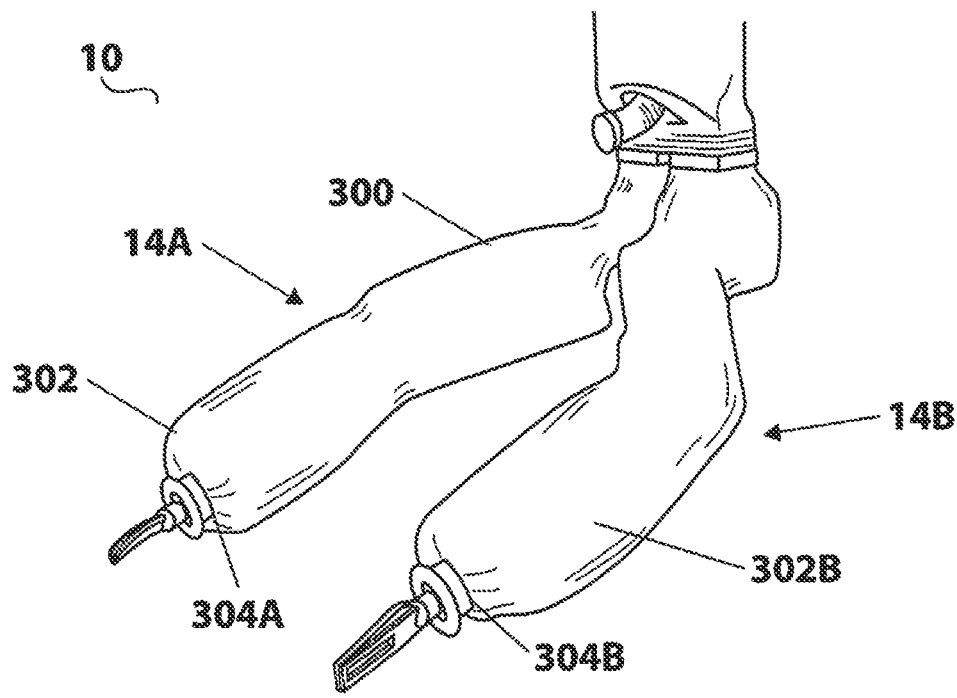
FIG. 10A is a perspective view of one embodiment of the robotic device comprising an inner fluidic seal.
Figure 10B:
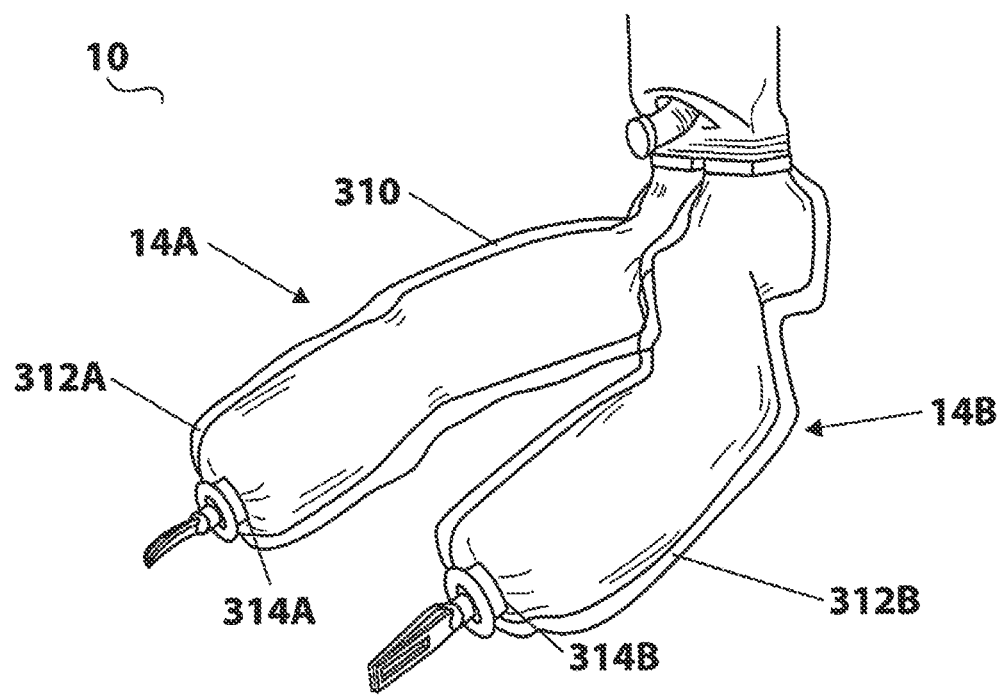
FIG. 10B is a perspective view of the embodiment of FIG. 10A further comprising further outer fluidic seal.

Additional fluidic seals can be provided according to certain embodiments as depicted in FIGS. 10A and 10B. As shown in FIGS. 10A and 10B, the device 10 can have two fluidically sealed barriers protecting each of the device arms 14A, 14B. The first barrier (also referred to herein as an "inner barrier") 300 is shown in FIG. 10A, in which it is positioned around each arm and coupled at the sleeve ends 302A, 302B to the device body 12 via elastic components 304A, 304B that urge the openings in the sleeve ends 302A, 302B, thereby enhancing the fluidic seal. In the embodiment as shown, the elastic components 304A, 304B are positioned around the forearms of the arms 14A at the distal ends of the forearms. Alternatively as described in detail above with respect to FIG. 8A, the elastic components 304A, 304B can be positioned in grooves defined in the forearms (such as grooves 270, 272 described above).

In one embodiment, the inner barrier 300 is a membrane that is permanently bonded to the device 10 and is not removed for the entire operational life of the device 10. The barrier 300 is sterilized with the device 10.

The second barrier (also referred to herein as an "outer barrier") 310 is shown in FIG. 10B, in which is positioned around each arm 14A, 14B, over the inner barrier 300 discussed above, and coupled at the sleeve ends 312A, 312B to the device body 12 via elastic components 314A, 314B that urge the openings at the sleeve ends 312A, 312B against the arms 14A, 14B, thereby enhancing the fluid seal.

Figure 11A:
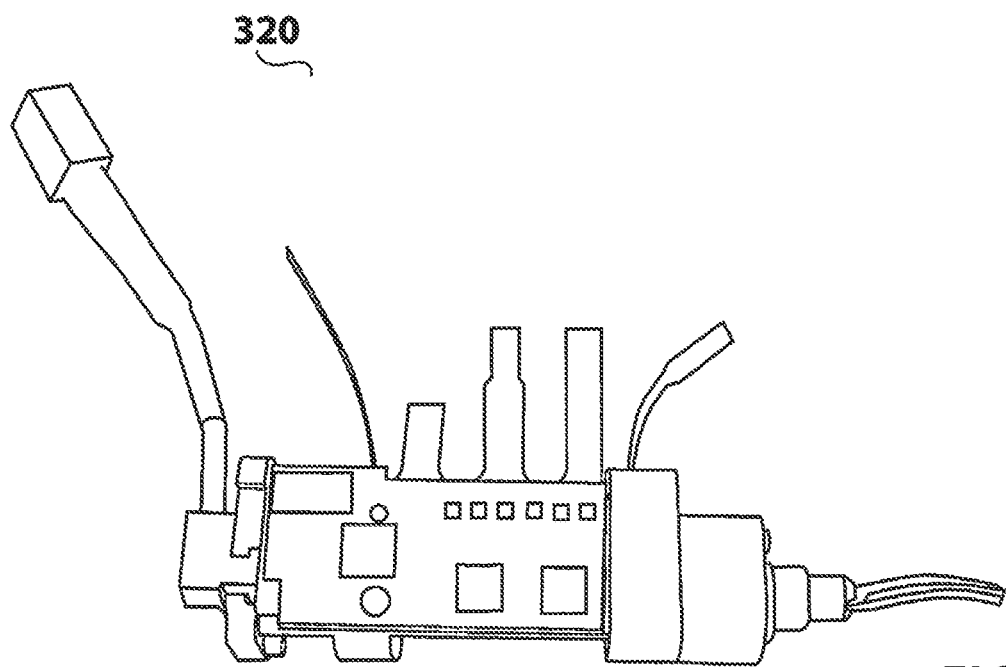
FIG. 11A is a side cutaway view of one embodiment of a rigid-flex PCB component within the forearm of the device.
Figure 11B:
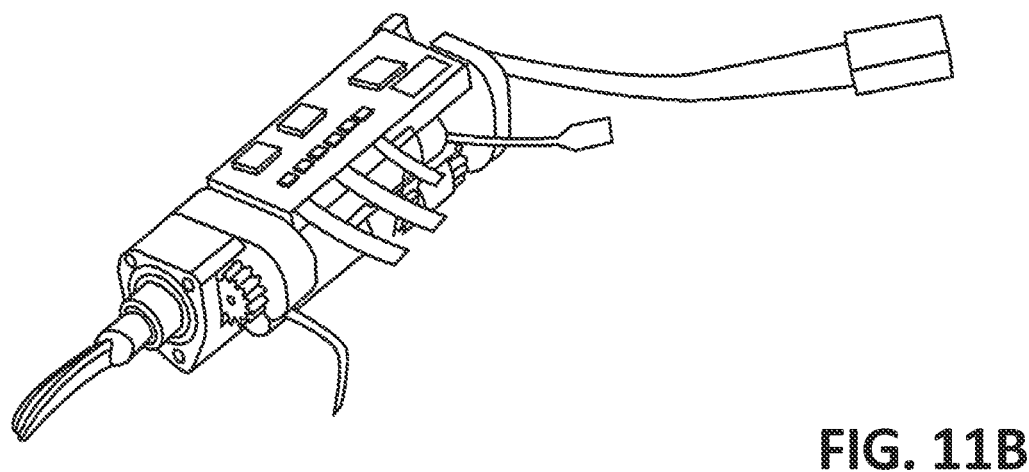
FIG. 11B is a further perspective view of the embodiment of FIG. 11A.
Figure 12A:
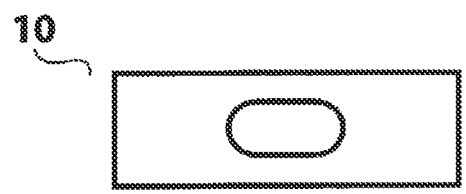
FIG. 12A depicts a top view of a robotic device during insertion, according to one embodiment.
Figure 12B:
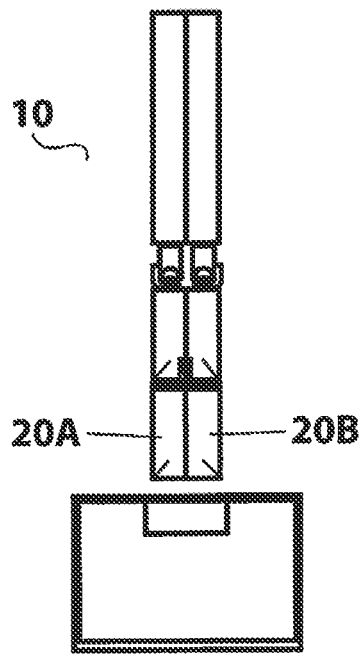
FIG. 12B is a front view of the device of FIG. 12A.
Figure 12C:
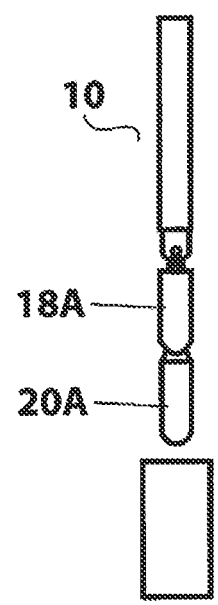
FIG. 12C is a side view of the device of FIG. 12A.
Figure 12D:
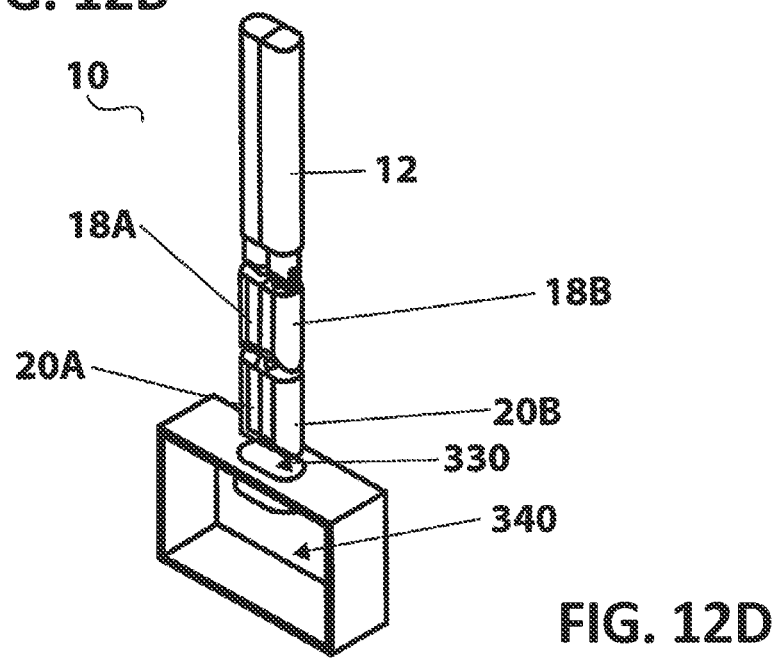
FIG. 12D is a perspective view of the device of FIG. 12A.
Figure 13A:
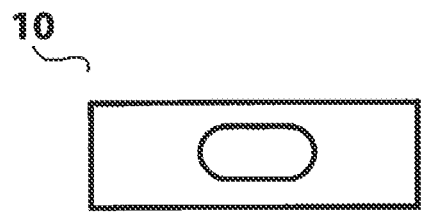
FIG. 13A depicts a top view of a robotic device during insertion, according to one embodiment.
Figure 13B:
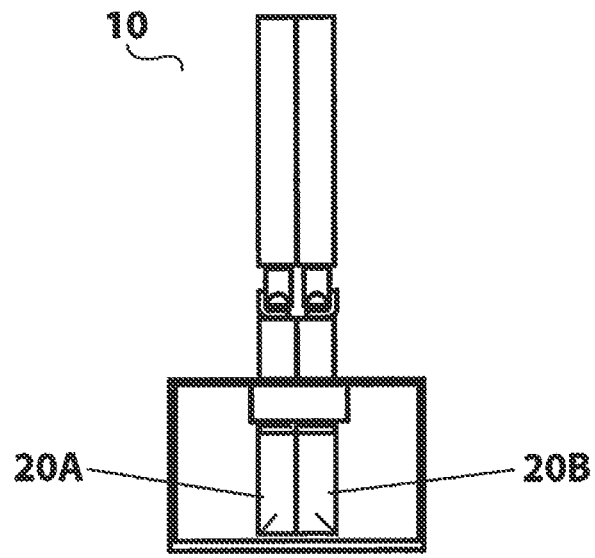
FIG. 13B is a front view of the device of FIG. 13A.
Figure 13C:
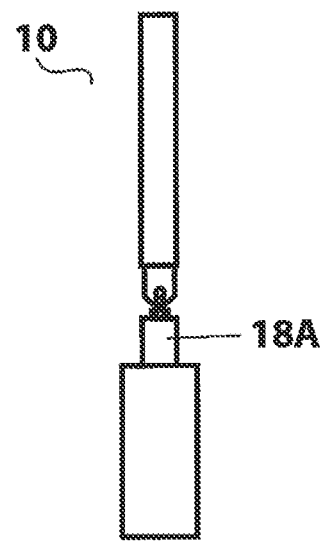
FIG. 13C is a side view of the device of FIG. 13A.
Figure 13D:
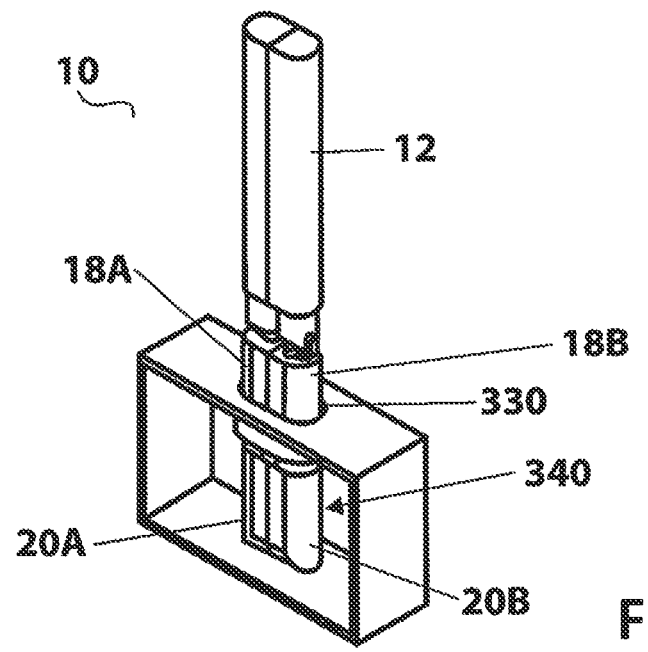
FIG. 13D is a perspective view of the device of FIG. 13A.
Figure 14A:
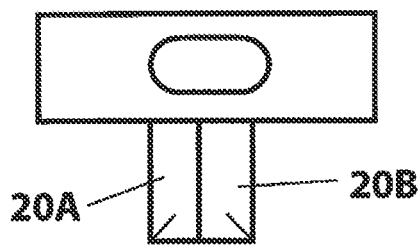
FIG. 14A depicts a top view of a robotic device during insertion, according to one embodiment.
Figure 14B:
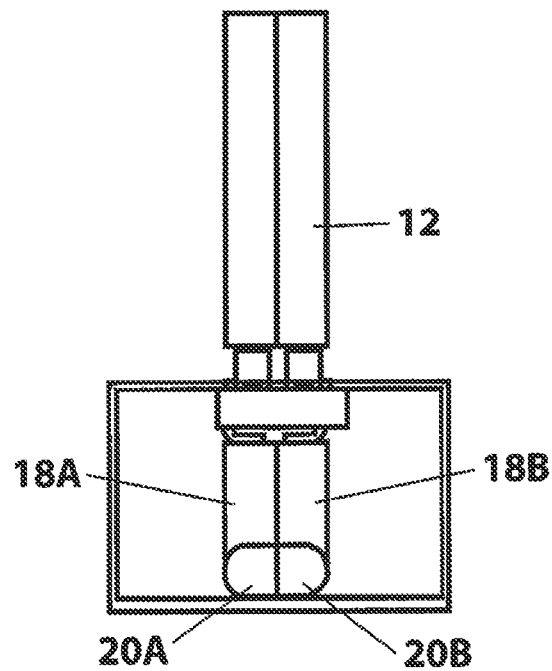
FIG. 14B is a front view of the device of FIG. 14A.
Figure 14C:
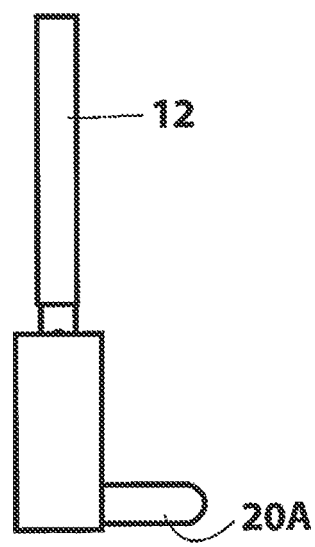
FIG. 14C is a side view of the device of FIG. 14A.
Figure 14D:
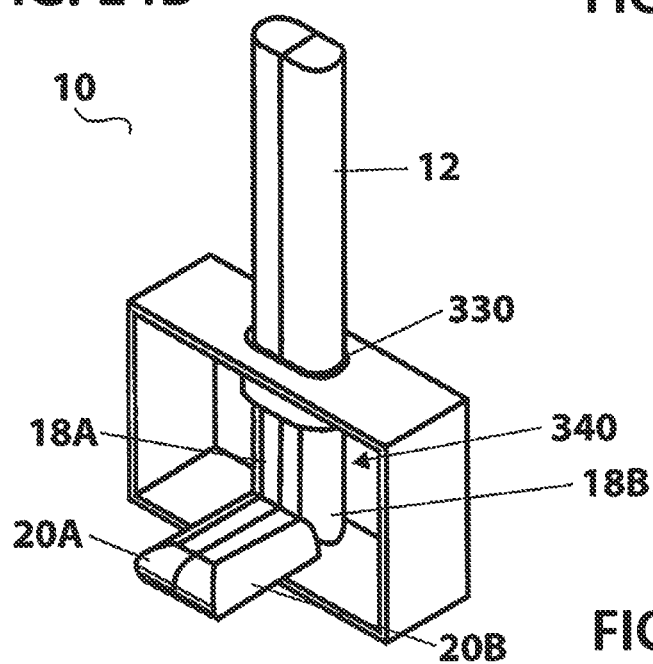
FIG. 14D is a perspective view of the device of FIG. 14A.
Figure 15A:
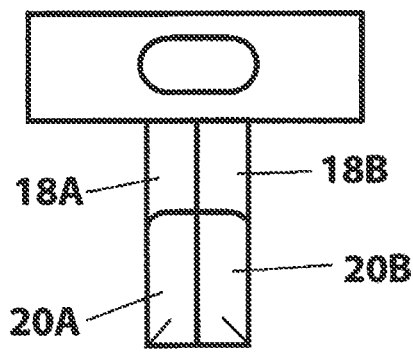
FIG. 15A depicts a top view of a robotic device during insertion, according to one embodiment.
Figure 15B:
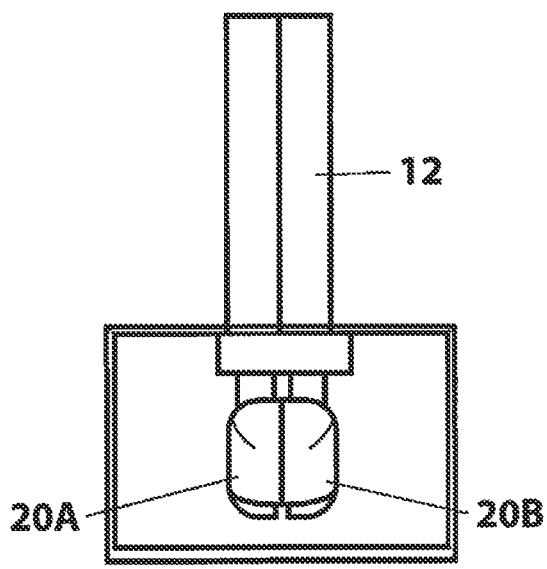
FIG. 15B is a front view of the device of FIG. 15A.
Figure 15C:
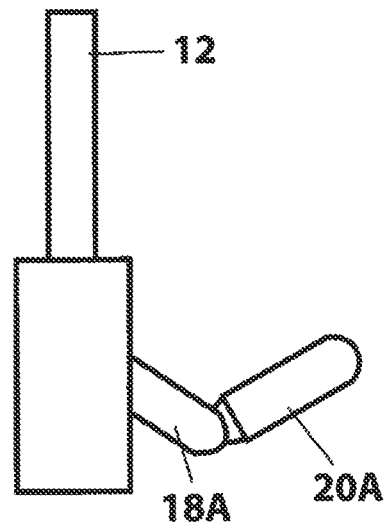
FIG. 15C is a side view of the device of FIG. 15A.
Figure 15D:
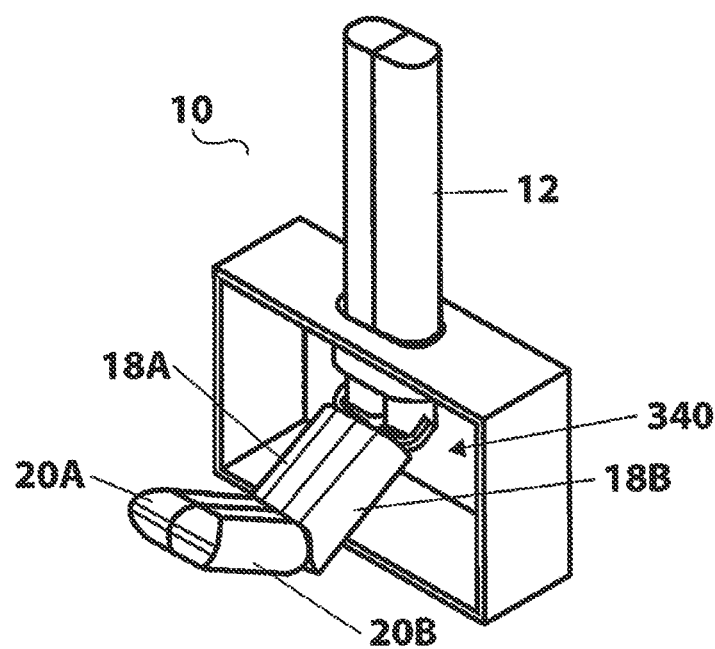
FIG. 15D is a perspective view of the device of FIG. 15A.
Figure 16A:
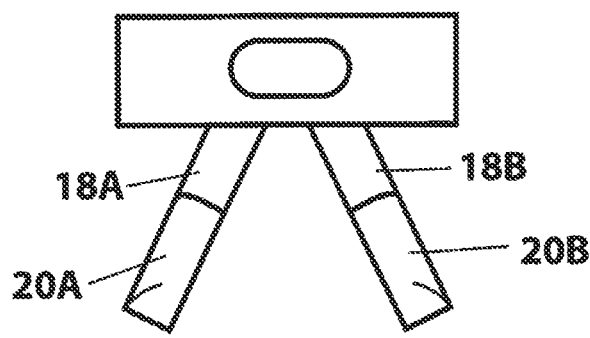
FIG. 16A depicts a top view of a robotic device during insertion, according to one embodiment.
Figure 16B:
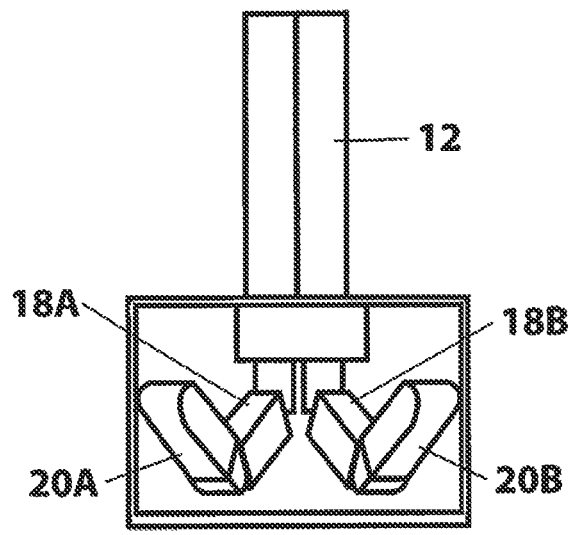
FIG. 16B is a front view of the device of FIG. 16A.
Figure 16C:
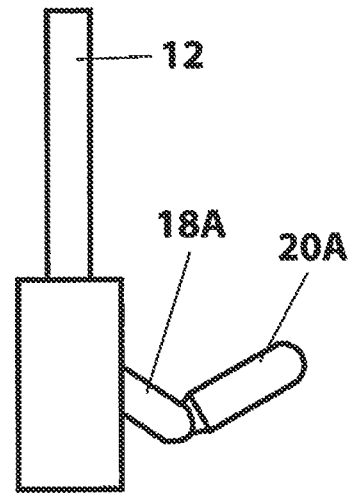
FIG. 16C is a side view of the device of FIG. 16A.
Figure 16D:
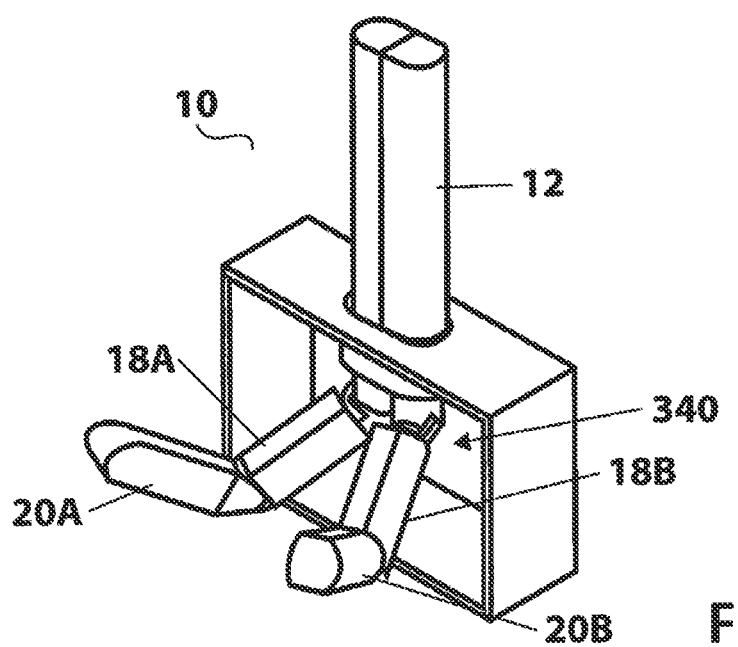
FIG. 16D is a perspective view of the device of FIG. 16A.
Figure 17A:
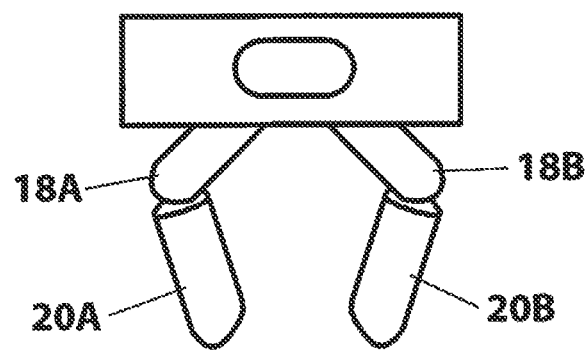
FIG. 17A depicts a top view of a robotic device during insertion, according to one embodiment.
Figure 17B:
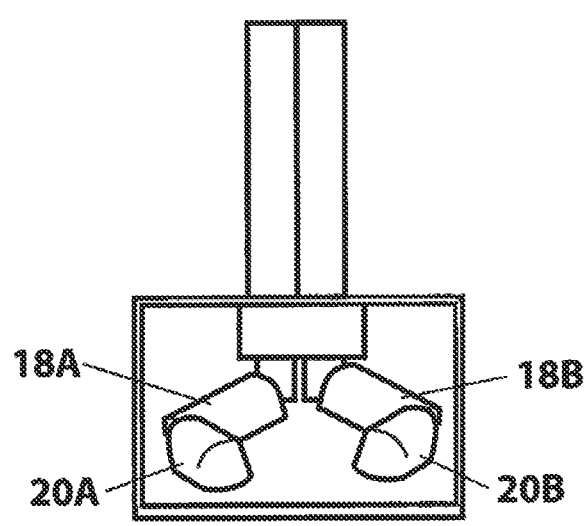
FIG. 17B is a front view of the device of FIG. 17A.
Figure 17C:
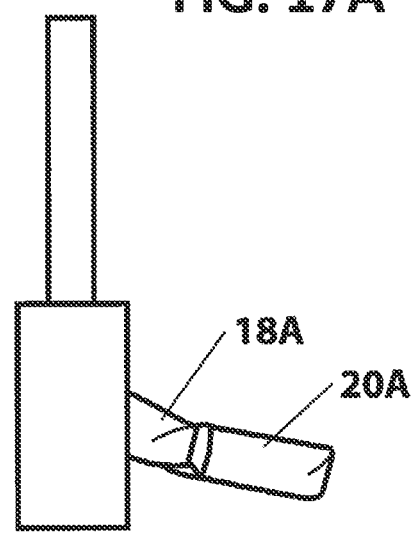
FIG. 17C is a side view of the device of FIG. 17A.
Figure 17D:
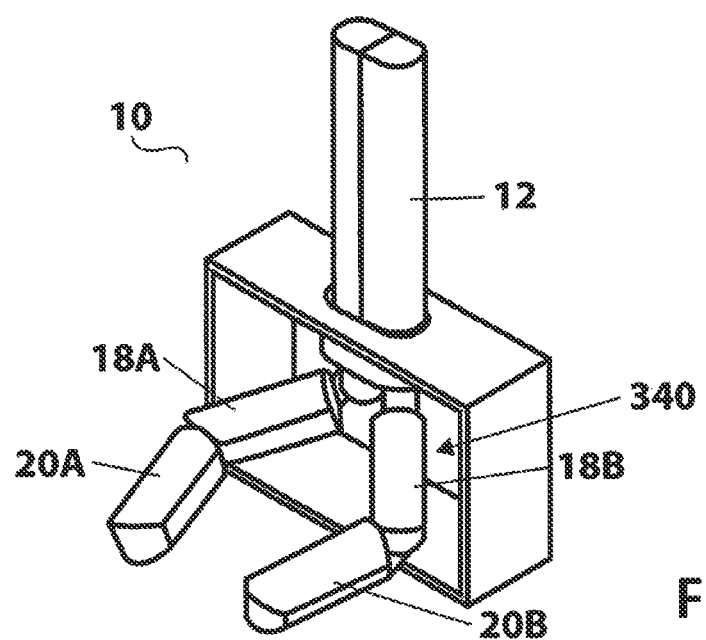
FIG. 17D is a perspective view of the device of FIG. 17A.

FIGS. 11A and 11B depict one embodiment of a rigid-flex PCB component 320 that can be used as the PCB component within the device embodiments as described above. It is understood that the rigid-flex assembly is a known fabrication method. In one embodiment, the PCB component 320 that has been assembled using a known fabrication method, but is custom designed and fabricated.

In use as shown in FIGS. 12-17, the device embodiments disclosed and contemplated herein are configured to have a consistent cross-section and minimal profile, thereby enhancing the ease of inserting the device through an incision and into a patient's cavity. Further, in one embodiment, the device 10 can be inserted via a specific set of steps that maintain the minimal profile and consistent cross-section in an optimal fashion. As shown in FIG. 12, the device 10 is being prepared to be inserted through the incision 330 and into the cavity 340. Note that the arms 14A, 14B of the device 10 are straight. In FIG. 13, the device 10 is inserted such that the forearms 20A, 20B are positioned in the cavity 340. As shown in FIG. 14, the forearms 20A, 20B can then be rotated as shown to maximize the amount of the device 10 that can be inserted. As the insertion continues as shown in FIG. 15, the upper arms 18A, 18B are also rotated to optimize the surgical space. At this point, the arms 14A, 14B can be moved into their operational position, first by urging them to move in opposite directions as shown in FIG. 16. Finally, the arms 14A, 14B are rotated so that the elbows are projecting outward in FIG. 17, thereby moving the arms 14A, 14B into their preferred operational position.

In one implementation, the device 10 has at least one camera that is used in conjunction with the device 10. For example, a camera (not shown) such as a camera having two degrees of freedom (a pan-and-tilt camera) having digital zoom could be used. In one embodiment, it is inserted through the camera lumen 32 defined in the proximal end of the device body 12 as best shown in FIG. 1C. According to one implementation, the camera can be controlled by the user or surgeon using a foot controller and would be easy to remove, clean, and re-insert during a procedure. In another embodiment, the camera can be a standard laparoscope inserted through the same incision, through the lumen 32, or through a different incision.

Figure 18G:
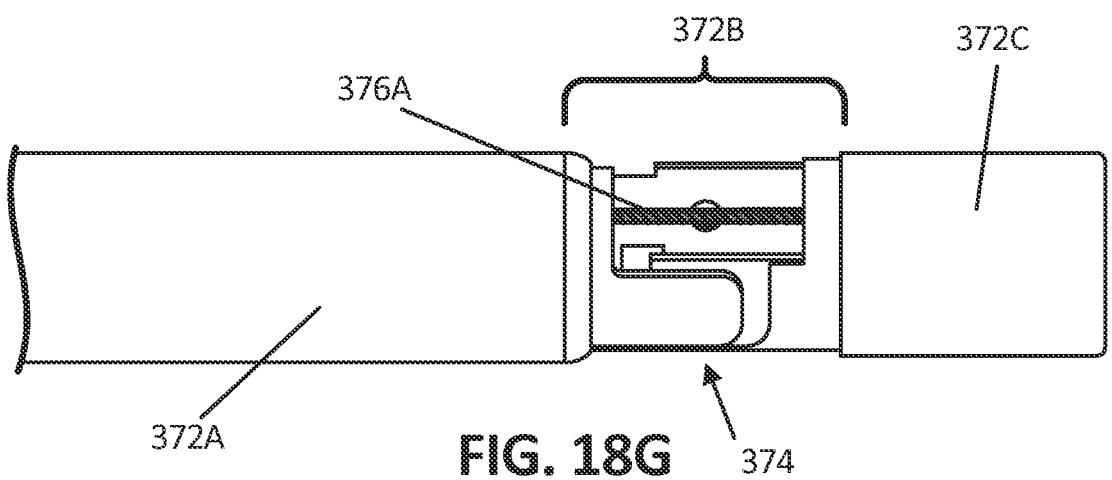
FIG. 18G is a close-up view of the distal end of a camera system, according to one embodiment.

Another embodiment relates to a robotic surgical system 350 having a camera system 352 as shown in FIGS. 18A-H. As best shown in FIGS. 18A and 18B, the camera system 352 in this specific implementation is configured to be removably incorporated into a robotic device 254. More specifically, the camera system 352 is configured to be removably positioned through a lumen 358 defined in the device body 356 such that the system 352 is inserted through the proximal opening 360 in the lumen 358 and into the lumen 358 such that a distal portion of the system 352 protrudes from the distal opening 362 (as best shown in FIG. 18A).

As shown in FIGS. 18C-18F, this camera system 352 embodiment has a controller (also referred to as a "handle" or a "body") 370 and an elongate component (also referred to herein as a "tube") 372 operably coupled at its proximal end to the handle 370. As best shown in FIG. 18D, the tube 372 has a rigid section 372A, a flexible section 372B, and an optical section 372C.

In one embodiment, the handle 370 is configured to contain local electronics (not shown) for video transmission, along with actuators and associated mechanisms (not shown) for actuating pan and tilt functionality of the tube 273. It is understood that the local electronics, actuators, and associated mechanisms can be known, standard components. In a further implementation, the handle 370 can also contain a light engine. Alternatively, the light engine can be a separate component, and a light cable can operably couple the light engine to the handle.

According to one implementation, the rigid section 372A of the tube 372 is substantially rigid and contains appropriate wires and optical fibers as necessary to operably couple to the optical component in the optical section 372C to the handle 370. The substantial rigidity of the rigid section 372A allows for easy manipulation of the tube 372, including easy insertion into the lumen 358.

The flexible section 372B, in accordance with one embodiment, is configured to allow for movement of the optical section 372C between a tilted configuration as shown in FIG. 18D and a straight configuration in FIG. 18F, or any position in between. The optical section 372C is substantially rigid, much like the rigid section 372A, and contains the optical element, along with appropriate local electronics, and a ring light (not shown).

In use, the camera system 352 has pan and tilt functionality that is powered and controlled by the actuators and electronics (not shown) in the handle 370. The tilt functionality relates to tilting the optical section 372C as described above. This tilting can be accomplished via a cable that is operably coupled to the flexible section 372B or the optical section 372C such that actuation of the cable causes the optical section 372C to tilt by bending the flexible section 372B as shown in FIG. 18D or 18E. Alternatively this tilt function can be achieved by any other known mechanism or method for bending the tube 372 at the flexible section 372B.

In one specific exemplary embodiment as shown in FIG. 18G, the tilt functionality can be accomplished via the following configuration. In this embodiment, the flexible section 372B includes an elbow joint 374 and a pair of tilt cables 376A, 376B, wherein each of the tilt cables 376A, 376B is operably coupled at its distal end to the optical section 372C. The first tilt cable 376A is depicted in FIG. 18G is an active tilt cable 376A that is coupled on one side of the optical section 372C in relation to the joint 374 as shown such that urging the cable 376A proximally causes the optical section 372C to tilt upward on that side. The second tilt cable 376B is not visible in FIG. 18G, but it is a passive tilt cable 376B that is coupled on the other side of the optical section 372C in relation to the joint 374 and the first title cable 376A. The second tilt cable 376B is not actuated by a user. Instead, the second tilt cable 376B is maintained at a predetermined level of tension such that the cable 376B is continuously urged in the proximal direction, thereby urging the optical section 372C into a straight configuration such as that shown in FIG. 18F.

As such, in this implementation of FIG. 18G, the default position of the optical section 372C will be the straight configuration of FIG. 18F. That is, the tensioned passive tilt cable 376B causes the optical section 372C to be in the straight configuration when no forces are being applied to the active tilt cable 376A, and a user can pull the active title cable 376A proximally to tilt the optical section 372C (and release the cable 376A to allow the section 372C to return to the straight configuration). The straight configuration of FIG. 18F makes it easy to position the camera system 352 into the lumen 358 as shown in FIG. 18B and further to remove the system 352 from the lumen 358 as well. In use, a user can urge the active cable 376A proximally to tilt the optical section 372C as desired/needed. In alternative embodiments, the system 352 can have an actuation button (or other type of user interface) (not shown) that can be configured to actuate the system 352 to move to the straight configuration of FIG. 18F, thereby facilitating easy insertion and/or removal.

Figure 18H:
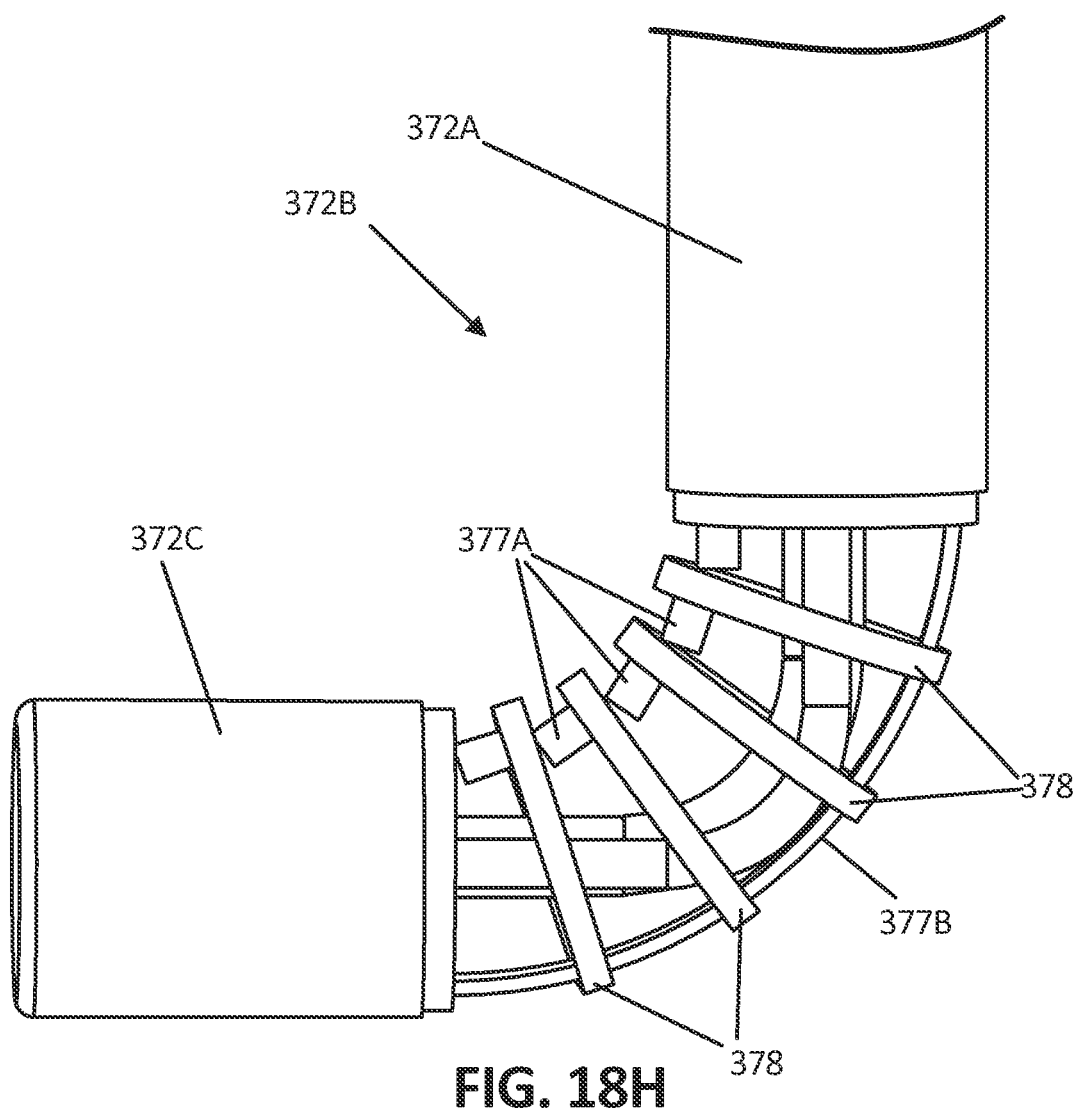
FIG. 18H is a close-up view of the distal end of another camera system, according to a further embodiment.

Another exemplary embodiment as shown in FIG. 18H depicts another tube 372 with tilt functionality. In this implementation, the flexible section 372B includes a pair of flexible spines 377A, 377B that are operably coupled at their proximal ends to the rigid section 372A and at their distal ends to the optical section 372C and supported by a set of discs 378. The first flexible spine 377A is an articulated spine 377A that is made up of two or more cylinders 377A that are operably coupled to the discs 378. An active cable (not visible) is disposed within the cylinders 377A and is operably coupled at its distal end to the optical section 372C such that urging the cable 377A proximally causes the optical section 372C to tilt upward on that side. The second flexible spine 377B is a spring element 377B that is not actuated by a user, but instead is configured to be in an untensioned state when the spring element 377B is straight (when the optical section 372C is in a straight configuration such as that shown in FIG. 18F) and is in a tensioned state whenever the spring element 377B is bent such that the spring element 377B is urging the optical section 372C back toward the straight configuration. Thus, like the previous embodiment depicted in FIG. 18G, in this implementation of FIG. 18H, the default position of the optical section 372C will be the straight configuration of FIG. 18F. That is, the second flexible spine 377B causes the optical section 372C to be in the straight configuration when no forces are being applied to the active cable (not visible) in the articulated spine 377A, and a user can pull the active cable proximally to tilt the optical section 372C (and release the cable to allow the section 372C to return to the straight configuration).

The pan functionality is accomplished via rotation of the tube 372 around the longitudinal axis of the tube 372 as shown by arrow A in FIG. 18C. The rigid section 372A, the flexible section 372B, and the optical section 372C of the tube 372 are coupled together such that the sections 372A, 372B, 372C cannot rotate in relation to each other. In other words, the sections 372A, 372B, 372C rotate together as a single unit. The tube 372, however, is rotatably coupled to the handle 370 such that the tube 372 can rotate as shown by arrow A in relation to the handle 370. As a result, the panning functionality is provided by positioning the optical section 372C in a tilted configuration (such as the configurations of FIG. 18D or 18E) and rotating the tube 372 in relation to the handle 370. This results in the optical component in the optical section 372C being rotated around the tube 372 axis such that it can potentially capture images up to and including 360° around the camera system 352.

It is understood that the camera system 352 can also provide for zoom and focus functionalities for the optical section 372C as well. These functionalities can be accomplished by any known mechanisms or methods. It is also understand all of the functionalities provided for the camera system 352 can be controlled from any user interface or console provided for use by the user or surgeon. Alternatively, some or all of these functions may be controlled manually via buttons or other interface mechanisms provided on the handle, such as the buttons associated with the handle shown in FIG. 19B, which are discussed in detail below.

In use, according to certain implementations, the camera system 352 is configured to be positioned into and removed from the lumen 358 (as best shown in FIGS. 18A and 18B) quickly and easily. Further, the lumen 358 is configured to have an internal fluidic seal (not shown) that provides a fluidic seal between the internal body cavity and the external air during surgery, thereby allowing for maintenance of the insufflation pressure in the cavity both when the camera system 352 is positioned in the lumen 358 and when it is not.

In accordance with one embodiment, the camera system 352 can be removed during a procedure so that it can be cleaned and/or defogged. Further, the system 352 can also be removed and used as a standard laparoscope (providing auxiliary views by being positioned through one or more auxiliary laparoscopic ports that are separate from the device port.

FIGS. 19A-19E depict another implementation of a robotic surgical system 380 having a removable camera system 382. In this embodiment, the system 380 has a device body 384 that is operably coupled at its proximal end with a receptacle 388 configured to receive the camera system 382. Further, the system 382 also has a positioning rod 386 (also referred to as a "control rod") that is removably coupled to the proximal end of the body 384 and/or to the receptacle 388.

Figure 19A:
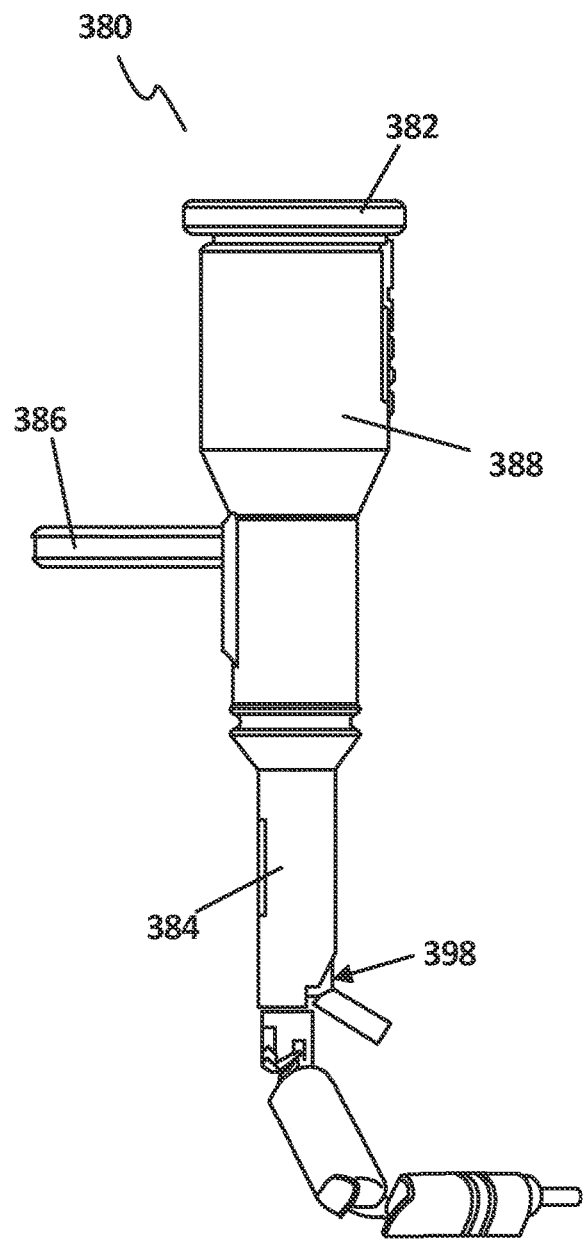
FIG. 19A is a side view of a surgical device with a removable camera system, according to a further embodiment.
Figure 19B:
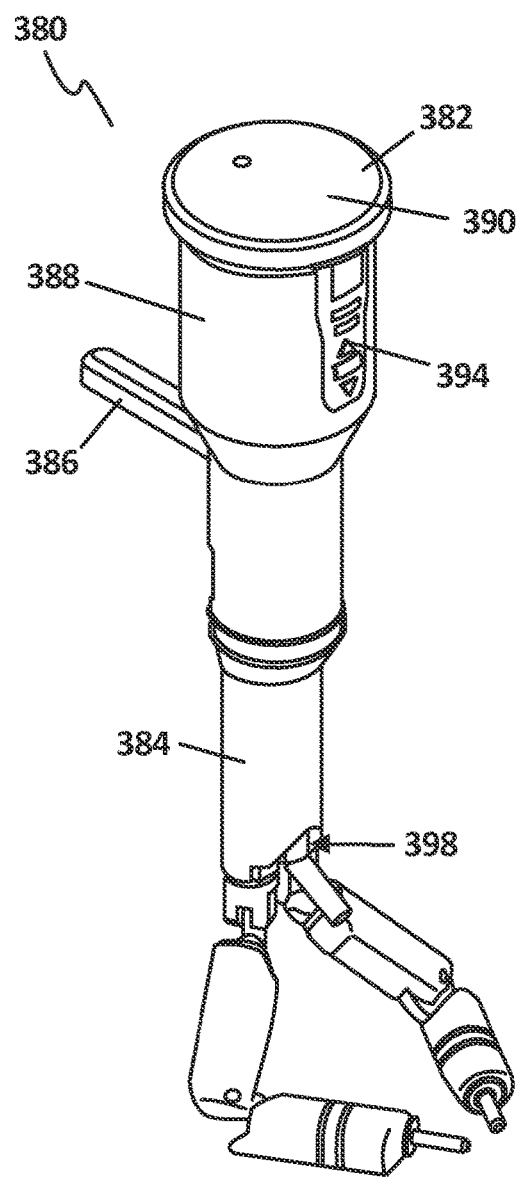
FIG. 19B is a perspective view of the device of FIG. 19A.
Figure 19C:
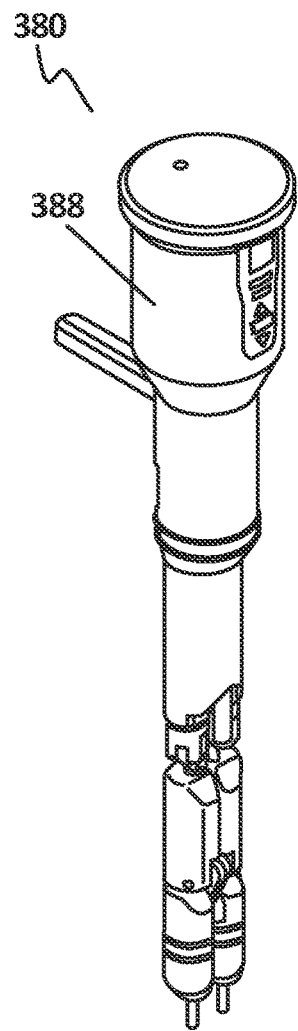
FIG. 19C is another perspective view of the device of FIG. 19A.
Figure 19D:
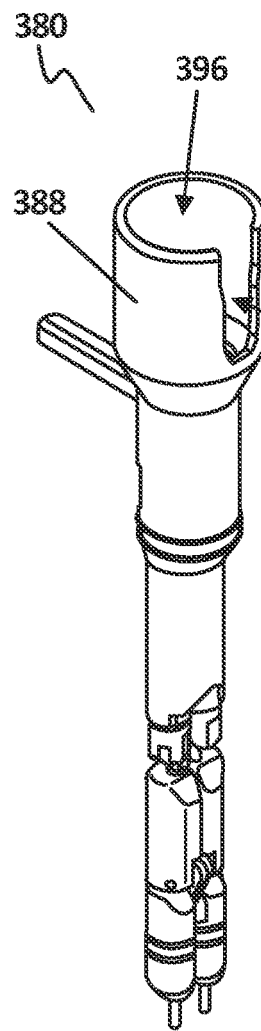
FIG. 19D is a further perspective view of certain components of the device of FIG. 19A.
Figure 19E:
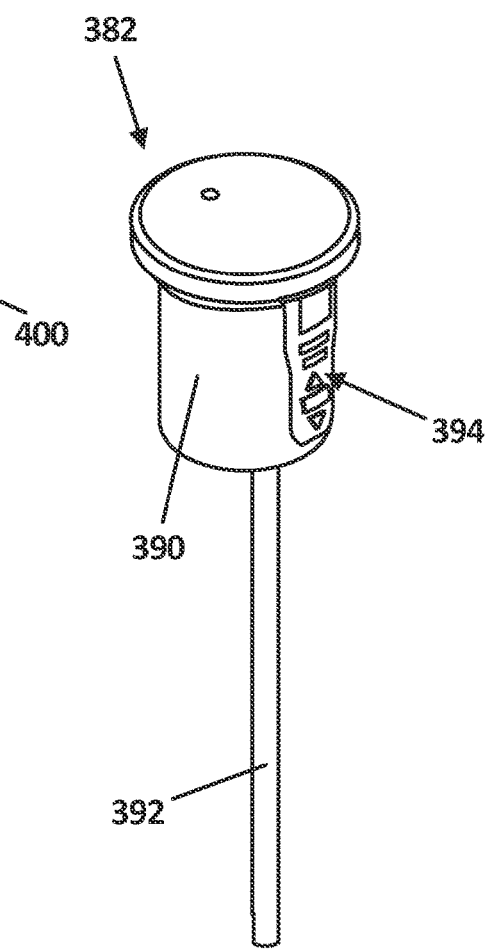
FIG. 19E is a perspective view of the camera system of FIG. 19A.

As best shown in FIG. 19E, like the system described above, the camera system 382 in this embodiment has a body 390 and an elongate component 392 operably coupled at its proximal end to the body 390. In this embodiment, the body 390 has an interface 394 (which is made up of a variety of buttons 394 in this embodiment) that allows a surgeon to control the system 382 via the interface 394.

According to one implementation best shown in FIG. 19D, the receptacle 388 defines an opening 396 into which the camera system 382 can be positioned. In addition, in this embodiment, a notch 400 is defined in the side of the receptacle that allows for user access to the interface 394 when the system 382 is positioned in the receptacle. Further, the opening 396 is in fluid communication with a lumen (not shown) defined in the device body 384, through which the camera system 382 can further be positioned. More specifically, the elongate component 392 of the camera 382 can be inserted through the opening 396 in the receptacle 388 and into the lumen (not shown) in the device body 384 until the distal end of the elongate component 392 is protruding out of the orifice 398 defined at the distal end of the lumen in the body 384, as best shown in FIGS. 19A and 19B.

The receptacle 388, in one implementation, can help to stabilize or strengthen the coupling of the camera system 382 with the device body 384, thereby reducing the changes that the camera system 382 will be disconnected from the rest of the system 380 during use.

Another embodiment of a robotic surgical system 420 with a removable camera system 422 is shown in FIGS. 20A-20C. As with the above embodiment, this system 420 has a receptacle 424 configured to receive the camera system 422. Further, the system 420 also has a positioning rod 426. The camera system 422 has a body 428 and an elongate component 430 operably coupled at its proximal end to the body 428. In addition, the body 428 has an interface 432.

Figure 21A:
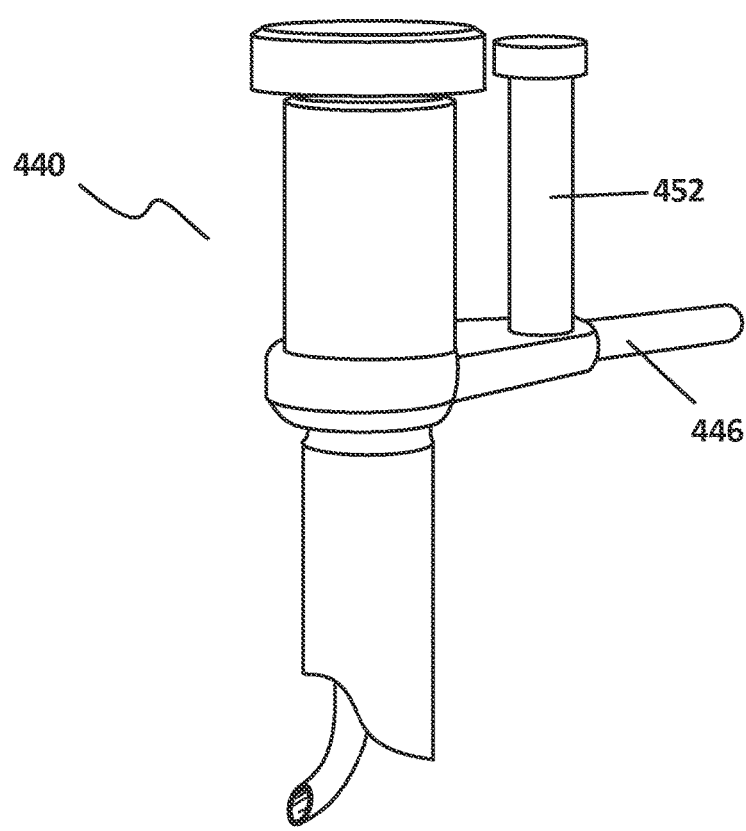
FIG. 21A is a perspective view of a surgical device with a removable camera system, according to another embodiment.
Figure 21B:
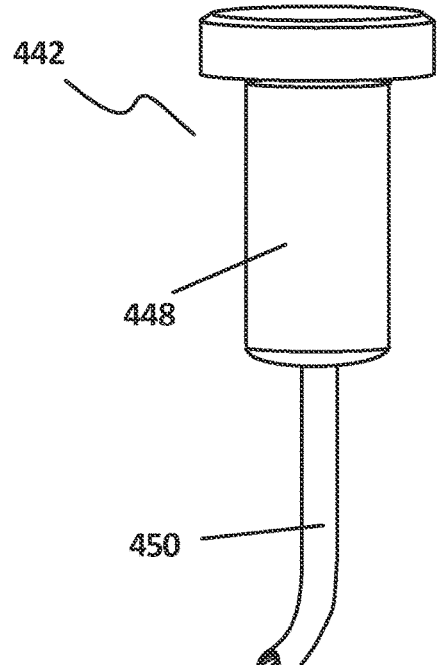
FIG. 21B is a perspective view of the camera system of the device of FIG. 21A.
Figure 21C:
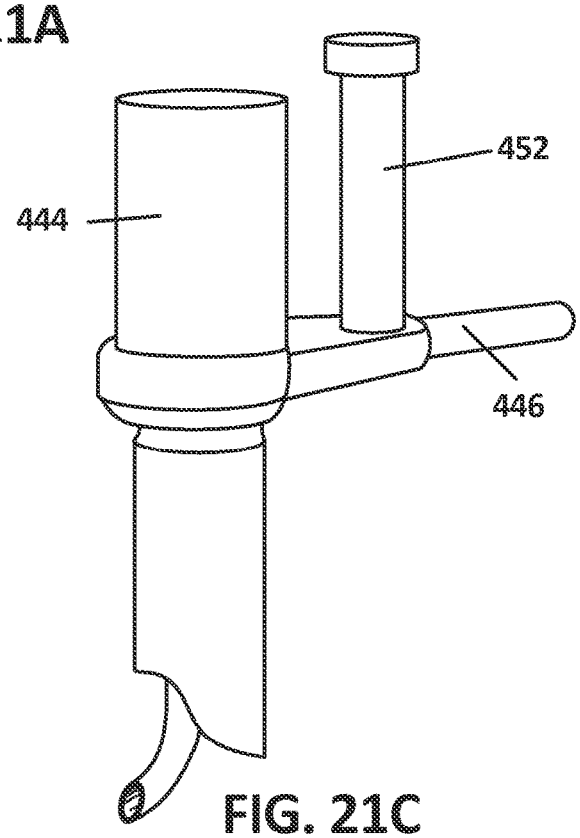
FIG. 21C is a perspective view of certain components of the device of FIG. 21A.

Another embodiment of a robotic surgical system 440 with a removable camera system 442 is shown in FIGS. 21A-21C. As with the above embodiment, this system 440 has a receptacle 444 configured to receive the camera system 442. Further, the system 440 also has a positioning rod 446. In this embodiment, the positioning rod 446 also has a surgeon handle 452 operably coupled thereto. The camera system 442 has a body 448 and an elongate component 450 operably coupled at its proximal end to the body 448.

Figure 22A:
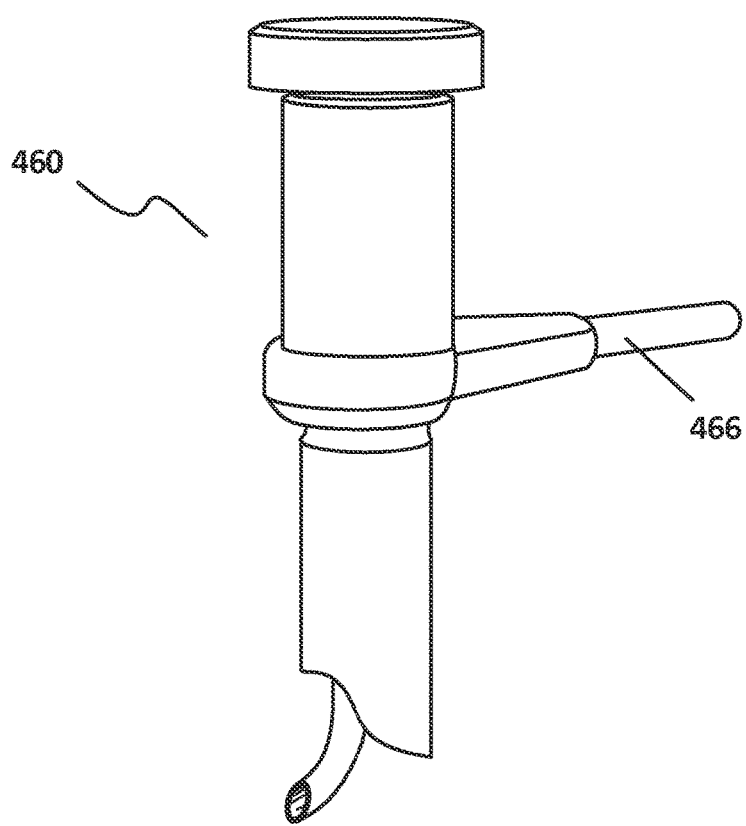
FIG. 22A is a perspective view of a surgical device with a removable camera system, according to yet another embodiment.
Figure 22B:
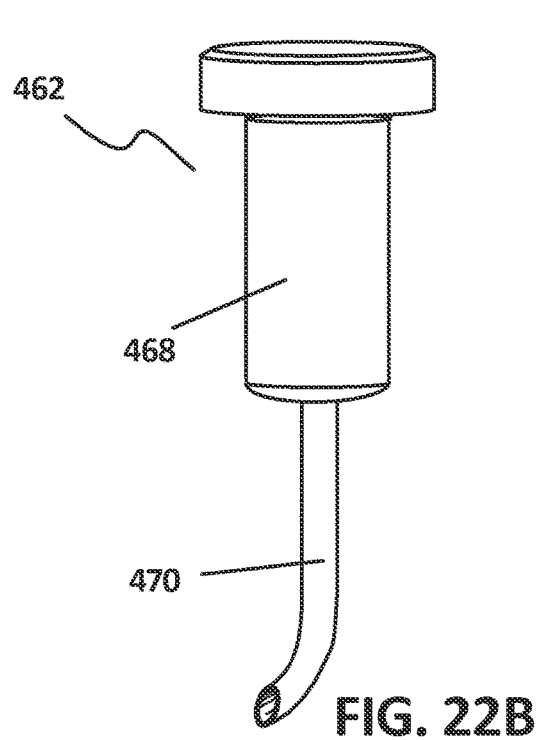
FIG. 22B is a perspective view of the camera system of the device of FIG. 22A.
Figure 22C:
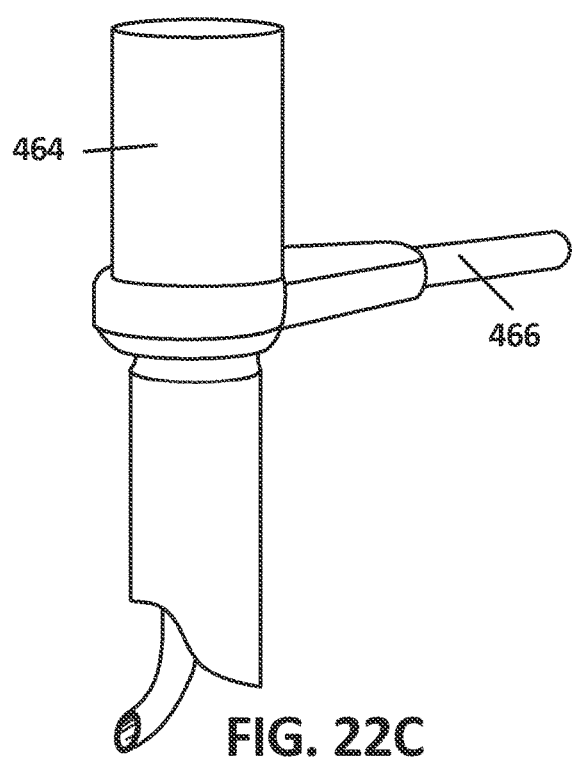
FIG. 22C is a perspective view of certain components of the device of FIG. 22A.

FIGS. 22A-22C depict yet another embodiment of a robotic surgical system 460 with a removable camera system 462. This embodiment is a variation of the embodiment shown in FIGS. 21A-22C, but this version does not have a surgeon handle. As such, this system 460 has a receptacle 464 configured to receive the camera system 462. Further, the system 460 also has a positioning rod 466. The camera system 462 has a body 468 and an elongate component 470 operably coupled at its proximal end to the body 468.

Figure 23A:
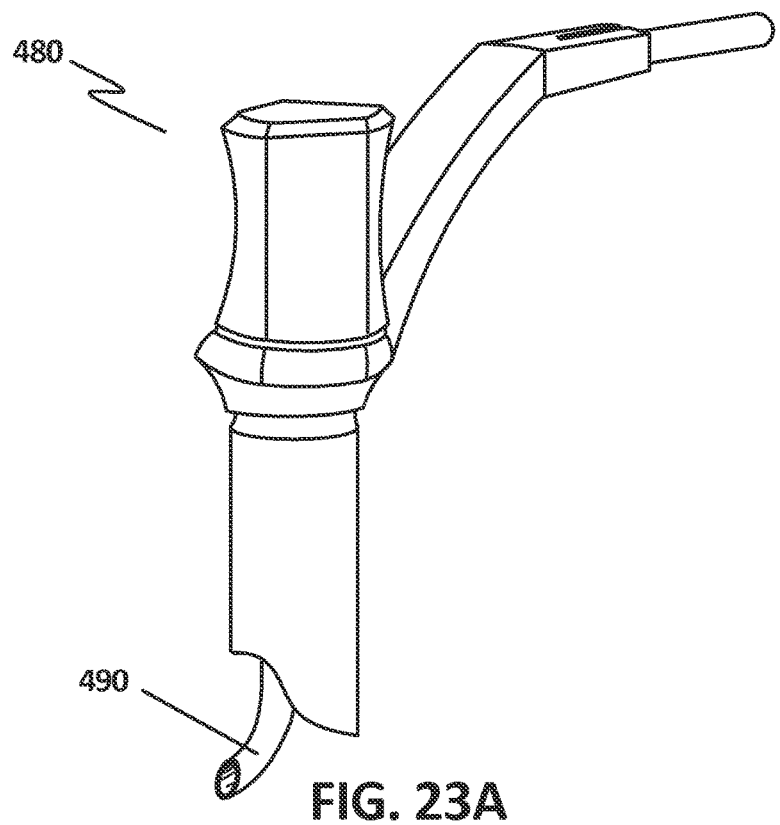
FIG. 23A is a perspective view of a surgical device with a removable camera system, according to yet another embodiment.
Figure 23B:
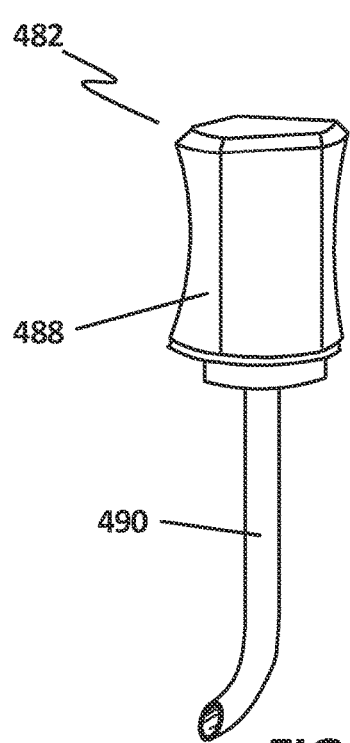
FIG. 23B is a perspective view of the camera system of the device of FIG. 23A.
Figure 23C:
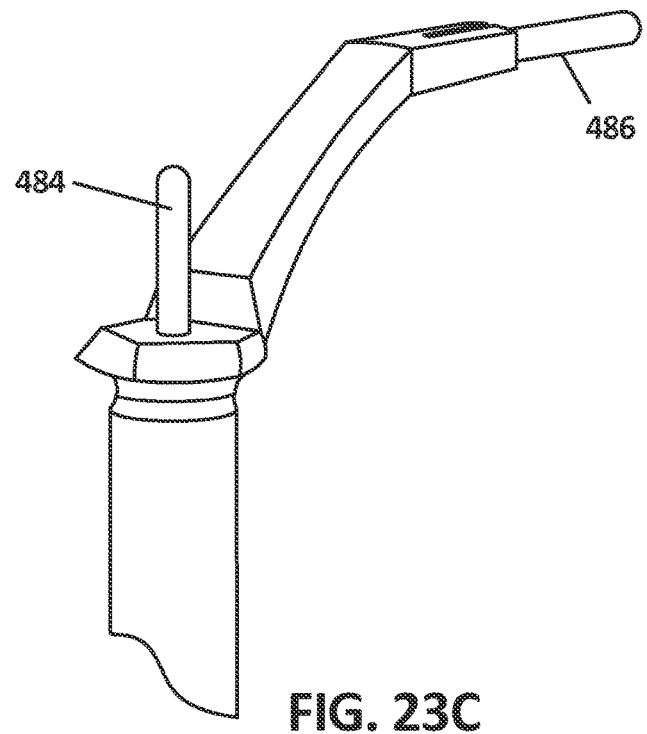
FIG. 23C is a perspective view of certain components of the device of FIG. 23A.

Another embodiment of a robotic surgical system 480 with a removable camera system 482 is shown in FIGS. 23A-23C. In this implementation, the system 480 has a male pin 484 (instead of a receptacle) that is configured to be inserted into a matching lumen (not shown) defined in the camera system 482. Further, the system 480 also has a positioning rod 486. The camera system 482 has a body 488 and an elongate component 490 operably coupled at its proximal end to the body 488. The lumen (not shown) is defined in the body 488 such that it has an opening on the underside of the body 488. As such, in use, the camera system 482 can be positioned such that the elongate component 490 is positioned through a lumen (not shown) such that the distal end protrudes as best shown in FIG. 23A. At the same time, the body 488 is positioned such that the male pin 484 is disposed into the lumen (not shown) in the body 488, thereby helping to retain the camera system 482 in position, coupled with the system 480.

In some embodiments, the various coupling embodiments described above that couple the camera system to the robotic system are sufficiently stable and/or strong that a surgeon can grasp the camera body and use it to position and otherwise manipulate the surgical device. In further alternatives, any known mechanism or component for firmly coupling a camera system to robotic surgical device can be used.

The various camera handles (or bodies) described herein, in certain implementations, are designed to have ergonomic shapes that provide comfort to the surgeon while holding onto those handles and positioning and/or manipulating the devices.

Figure 24A:
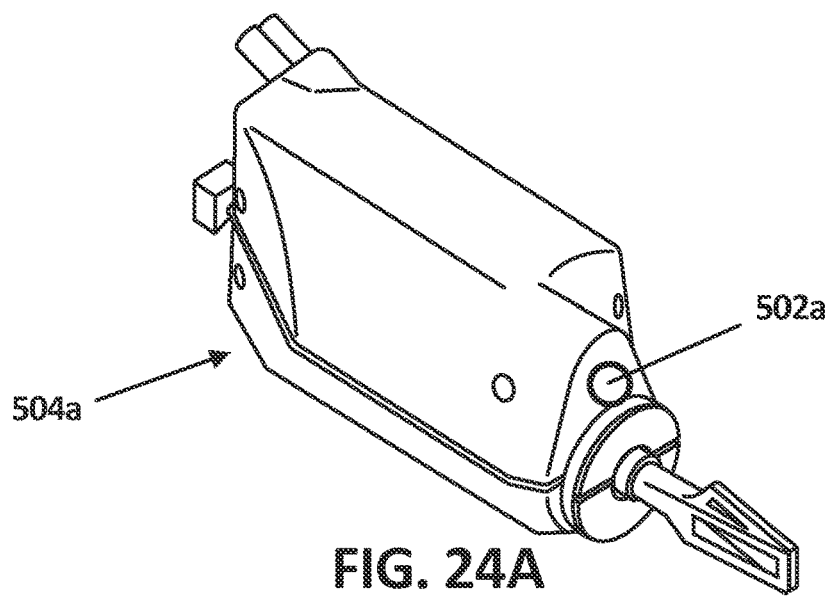
FIG. 24A is a perspective view of an arm of a surgical device, according to one embodiment.
Figure 24B:
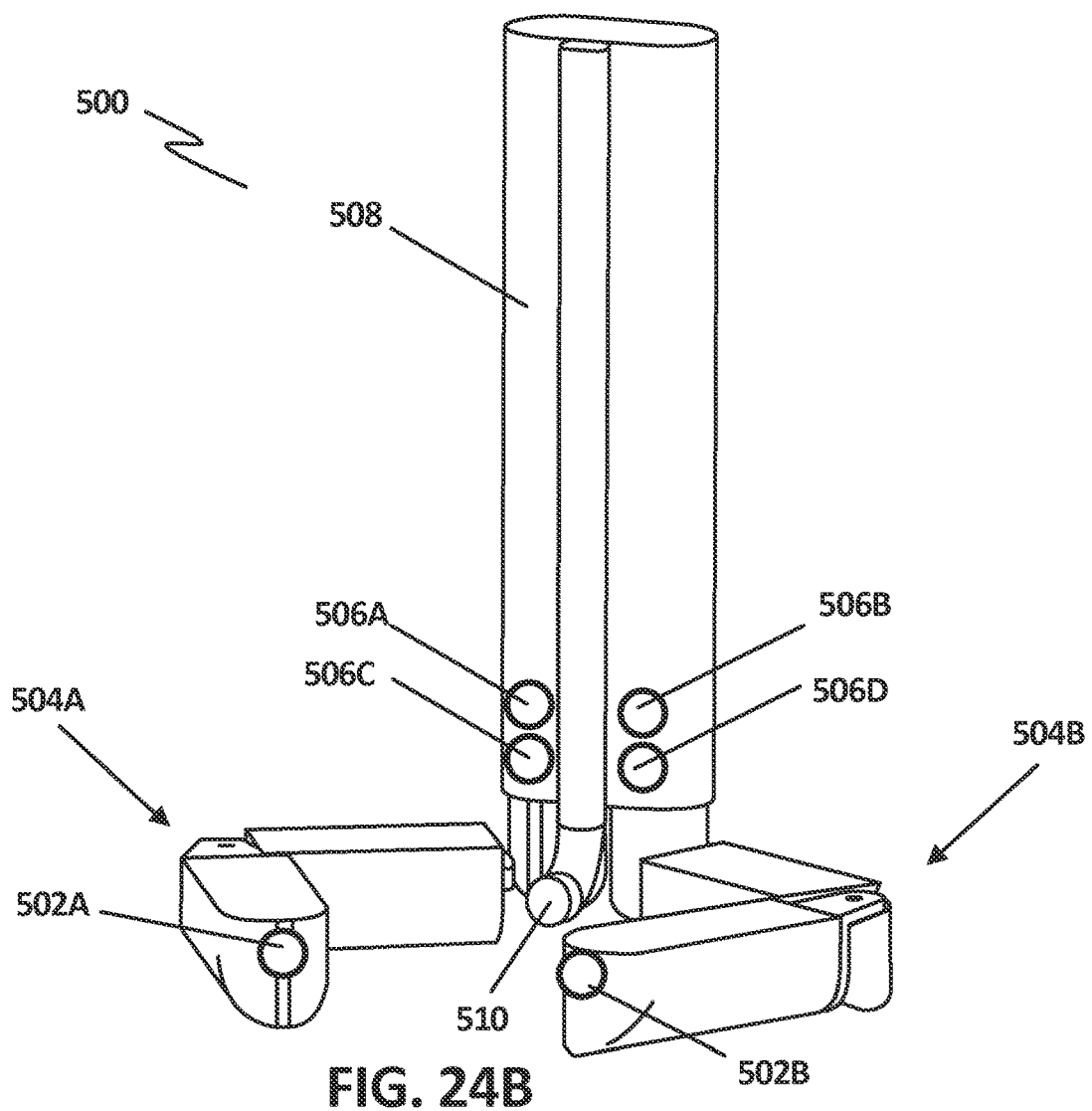
FIG. 24B is a perspective view of a surgical device, according to one embodiment.

FIGS. 24A and 24B depict one embodiment of a robotic surgical system 500 with various lighting components in a unique configuration. Standard lighting configurations typically involve single-point lighting, usually from a light ring positioned around the camera or laparoscope. The deficiencies of single-point lighting include poor illumination, loss of depth perception, shadows, etc. In contrast, this system 500 has multiple lighting components in multiple locations, thereby providing better lighting that is multi-point in nature and thus eliminating the deficiencies described above, making it easier for the surgeon to see the target area within the cavity during surgery.

As shown in FIGS. 24A and 24B, the system 500 has six different lighting components, including a lighting component 502A, 502B in each robotic arm 504A, 504B and four lighting components 506A, 506B, 506C, 506D associated with the device body 508. In addition, in certain embodiments, the camera tip 510 can also have a standard light ring as well. Alternatively, the camera tip 510 has no lighting component. In a further embodiment, the system 500 has at least two lighting components. In yet another embodiment, the system 500 has at least three lighting components, with at least one on each robotic arm 504A, 504B and at least one on the device body 508. In a further alternative, any number of lighting components can be used that provide quality lighting for a surgeon during a surgical procedure.

The lighting components, in one implementation, are LED lights. Alternatively, any known lights of any form can be used.

In certain implementations, the light source is positioned or otherwise located in the handle of the camera system (such as a system described above), elsewhere in the device body 508, or in an external component positioned outside of the patient's body (such as in a controller or a separate light source, for example). In these embodiments, fiber wires are operably coupled to both the light source and to the lighting components (such that the wires run between the light source and the components), thereby allowing for transmission of light from the source to the components.

Figure 25A:
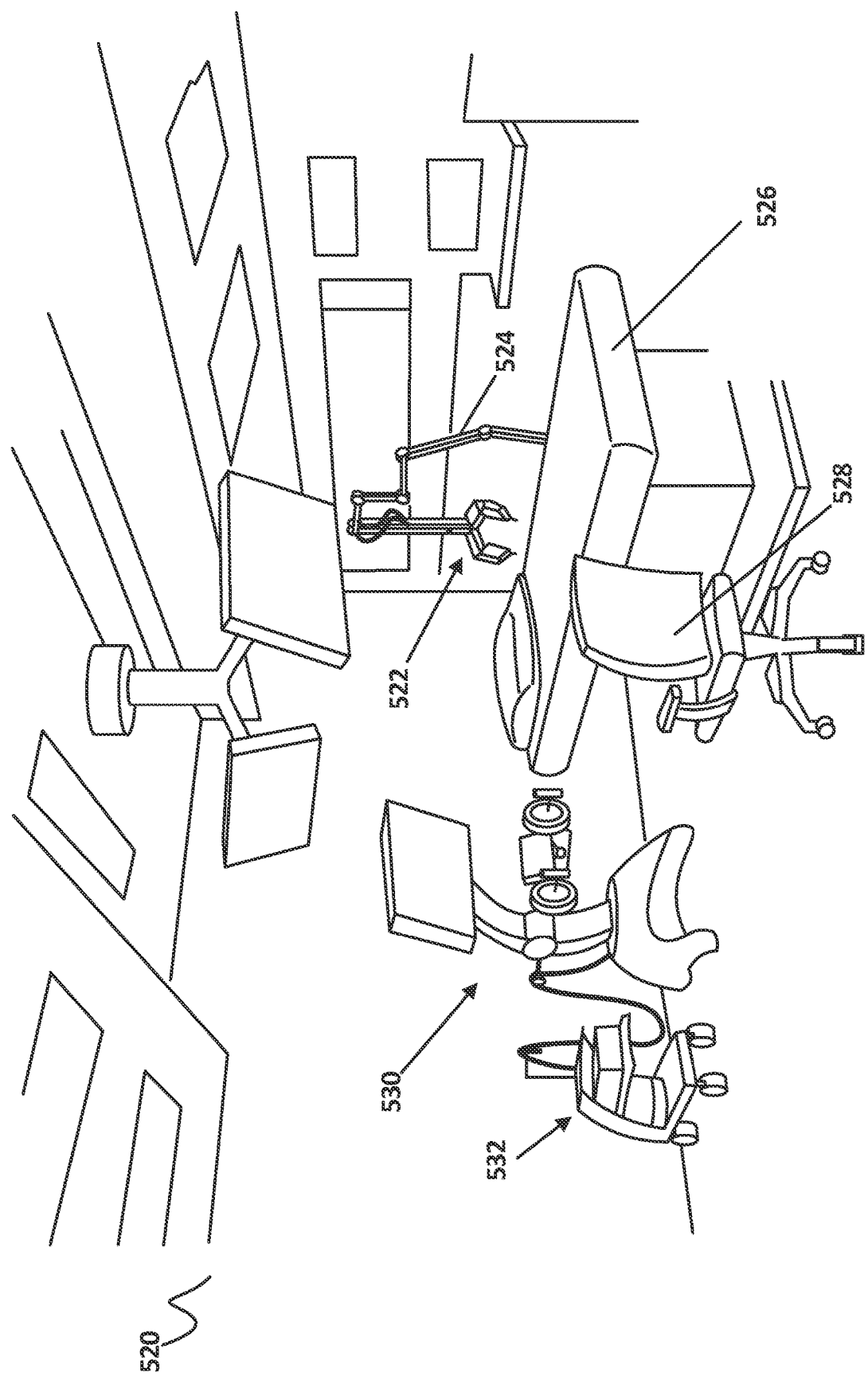
FIG. 25A depicts an operating theater in which any surgical device embodiment contemplated herein can be used, according to one embodiment.
Figure 25B:
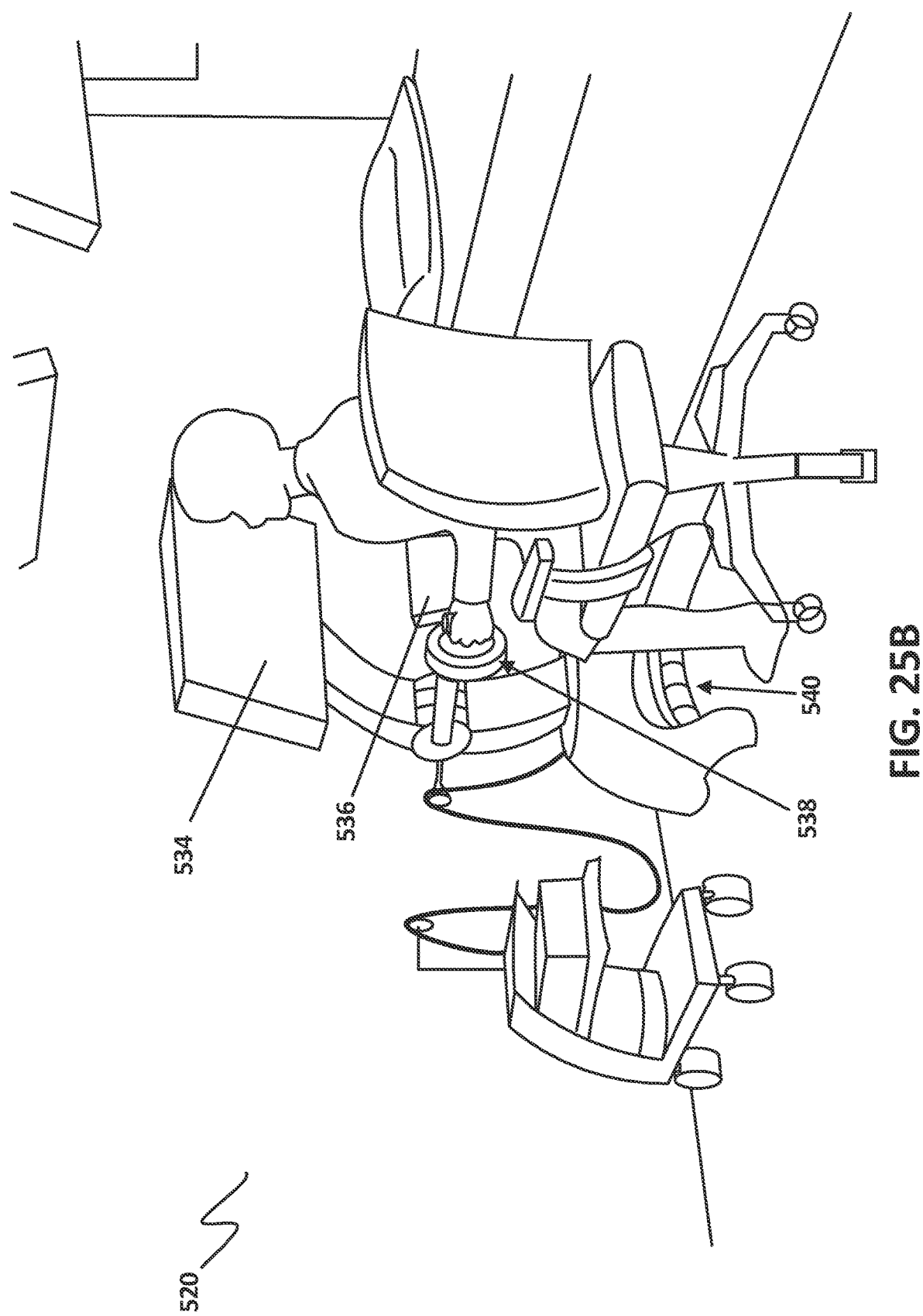
FIG. 25B is a close-up view of a portion of the operating theater of FIG. 25A in use.

FIGS. 25A and 25B depict an operating theater 520 according to one embodiment in which any of the robotic surgical systems described above can be used. As best shown in FIG. 25A, the theater 520 has a robotic surgical system 522, a positioning rod (also referred to herein as a "robot support arm") 524, an operating table 526, a surgical chair (also referred to herein as a "surgeon's chair" or "surgeon chair") 528, a controller (also referred to herein as a "console" or "surgeon console") 530, and a cautery generator 532.

The robotic system 522 is clamped to (or otherwise coupled to) the distal end of the robot support arm 524. The proximal end of the support arm 524 is clamped or otherwise coupled to a standard support strut on the operating table 526. In this embodiment, the support arm 524 has 6 degrees of freedom, which are manually released by a single knob. In use, the user can release the support arm 524 by loosening the knob, move the robotic system 522 to a suitable position, then tighten the knob, thereby rigidizing the arm 524 and fixing the robotic system 522 in place. One example of a commercially-available support arm 524 is the Iron Intern™, made by Automated Medical Products Corp.

The operating table 526 is a standard operating table found in standard operating rooms. In this embodiment, it has a support strut (not shown) on both sides of the table 526 for clamping or attaching accessories.

The chair 528 is designed or selected with surgeon comfort and safety in mind. The chair has adjustable arm supports such that the surgeon's arms will be comfortably supported throughout the entire procedure and thus will not tire.

As best shown with reference to both FIGS. 25A and 25B, the controller 530 in this embodiment has a surgical monitor (such as a high definition monitor) 534 that displays the output of the camera associated with the surgical system 522, as well as critical system information and robotic system status. The controller 530 also has an auxiliary monitor and control pad 536. This component 536 can display non-critical system information while also provide a user interface. In one embodiment, this auxiliary monitor and pad 536 can be a touch screen interface 536. Alternatively, it can be a traditional button/switch control panel. In a further alternative, the auxiliary monitor and pad 536 can be a combination of the two. Auxiliary controls provided by the auxiliary monitor and pad 536 can include, but are not limited to, camera controls (pan, tilt, zoom, focus, lighting, etc.), controller input scaling, and a step through insertion and extraction procedure.

The console 530 also has two hand controllers (also referred to as manipulators) 538 that are used to control the robotic system 522. In this embodiment, the left controller 538 can be operated by the surgeon's left hand and controls the left arm of the robotic system 522, while the right controller 538 can be operated by the surgeon's right hand and controls the right arm of the robotic system 522. In certain implementations, the controllers 538 provide haptic feedback to inform the surgeon of the state of the robot. As used herein, haptic feedback will include, but is not limited to, information about the workspace limits of the robotic system 522 and the load placed on the system 522. The controllers 538 can also have "dead man" switches which require the surgeon to grip both controllers properly in order to operate the system 522. According to one embodiment, the controllers 538 can have 7 degrees of freedom ("DOF") each: three DOF for Cartesian coordinates X, Y, and Z, three angles for orientation, and one for controlling the opening and closing of an end effector on the robotic system 522.

According to one implementation, the console 530 can also have foot pedals 540. The foot pedals 540 can provide several functions, including, for example, control of a monopolar cautery, control of a bipolar cautery, and/or clutching.

The console 530 in certain embodiments can also be coupled to a cautery generator 532. The generator 532 can supply power for both monopolar and bipolar tools. It is electrically routed through the console 530 in this embodiment for activation and safety monitoring.

Additional console 530 components include a computer (not shown) and a power supply (not shown). The computer, in one embodiment, can run user interface software and control all high level functions of the robotic system 522. The power supply can be, for example, a known medicallycertified power supply unit that distributes power to the entire system, including the robotic system 522 (and associated camera system), the computer, and any other components that require power.

Figure 26:
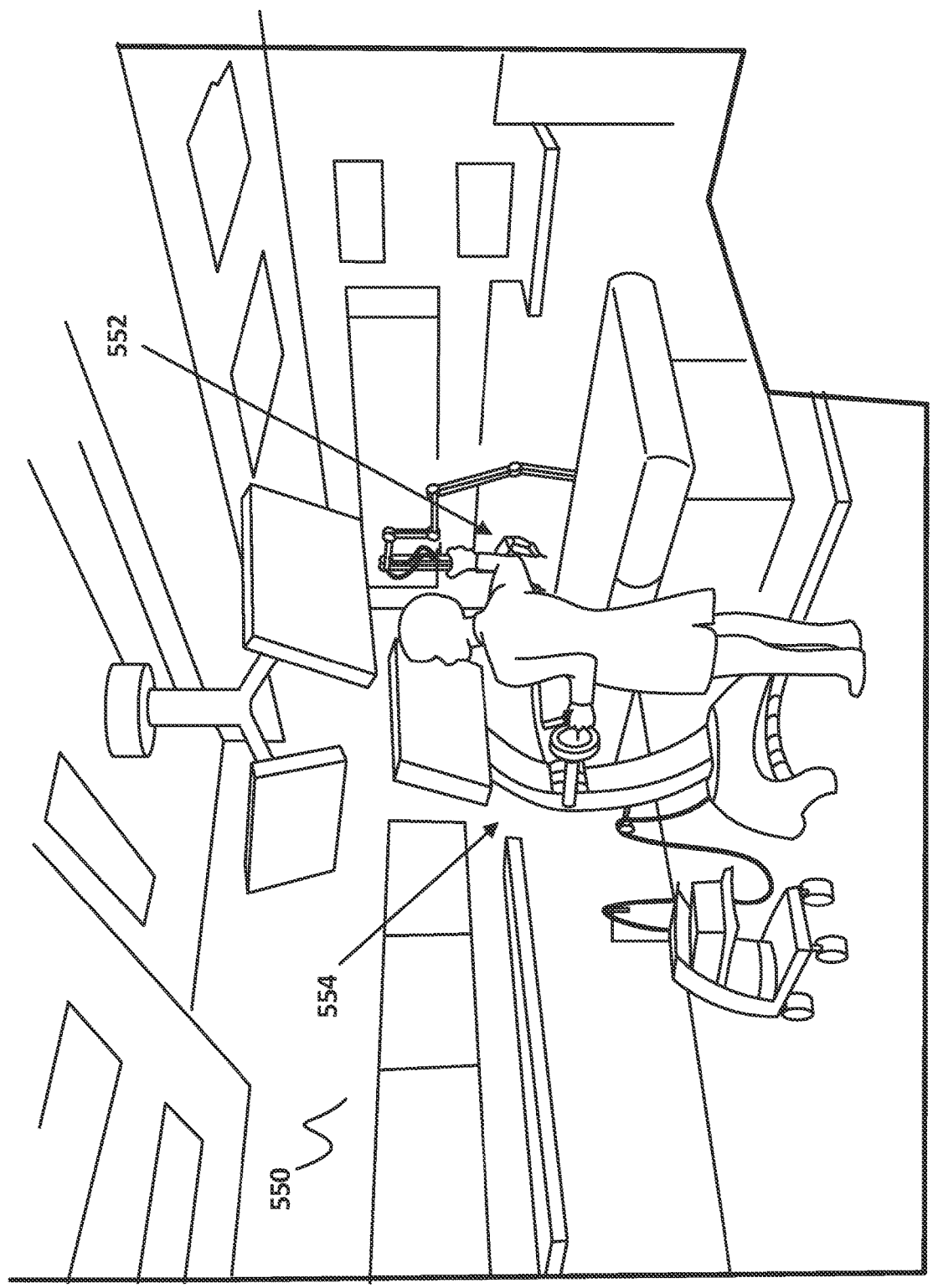
FIG. 26 depicts another operating theater in which any surgical device embodiment contemplated herein can be used, according to a further embodiment.

FIG. 26 depicts another implementation of an operating theater 550 in which the robotic system 552 is operated in a different fashion. In this embodiment, the surgeon stands (instead of sitting as shown in the previous embodiment) at the console 554. Further, the surgeon (or another person present in the theater 550) using this configuration can manually manipulate the positioning of the robotic system 552 by hand by simply grasping the system 552.

In use, any of the robotic system embodiments discussed in detail above can be inserted into the target cavity of the patient in the following manner. As depicted in FIGS. 27A-27D, in one implementation, an insertion system 560 can be used for accessing an insufflated cavity of a patient and/or positioning surgical systems or devices into the cavity. The various insertion system embodiments disclosed and contemplated herein provide for insertion of the surgical systems/devices into the cavity while maintaining sufficient insufflation of the cavity. That is, these insertion systems form a pressure lock with the patient's internal cavity, thereby allowing insertion, operation, extraction, and repositioning of a surgical device without loss of insufflations. Further embodiments minimize the physical contact of the surgeon or surgical users with the surgical devices/systems during the insertion process. Other implementations enhance the safety of the insertion process for the patient and the systems/devices. For example, some embodiments provide visualization of the system/device as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

The system 560 is an external pressurized system 560 that has a flexible and/or collapsible insertion bag or canister 562 with a compliant volume. The system 560 can enclose a robotic system during an insertion procedure while allowing for the insufflation of the patient's cavity. The insertion bag 562 is configured to be coupled at its proximal end with the proximal insertion cap (also referred to as a "top cap") 564 and at its distal end with the distal insertion cap (also referred to as a "bottom cap" or "base portion")) 566 and port 568 such that a seal is established that can withstand any known insufflation pressure. The port 568 is positioned in an incision in the skin (not shown) of the patient, thereby providing access to a cavity (not shown) of the patient.

In embodiment, the canister 562 is made of a flexible material such as, for example, polyethylene plastic, latex, nylon, or silicone rubber. Alternatively, the canister 562 can be made of any known flexible or collapsible material that can be used in medical devices. It is understood that certain embodiments of the canister 562 are transparent. The transparent canister 562 allows for the user to see the surgical device (not shown) during insertion. Alternatively, the canister 562 is not transparent and the device can be inserted without being able to view the device in the canister 562.

According to one embodiment, the proximal insertion cap 564 couples to the proximal end of the canister 562 and provides the interface between the robotic system and the bag 562. In one exemplary embodiment, the robotic device can have a groove (not shown) defined around a portion of the device body (or elsewhere on the device) around which the cap 564 can be positioned to establish a seal. The cap 564 can also contain a pressure release valve (not shown) that can reduce or prevent harmful buildup of pressure during the insertion procedure and throughout the operation.

The distal insertion cap 566 is configured to be coupled to the distal end of the insertion bag 562 and to the port 568 such that a seal is established that can withstand any known insufflation pressure. The coupling of the distal insertion cap 566 to the port 568 can be accomplished through a standard, preexisting interface. In one implementation, the distal insertion cap 566 can have a rigid insertion shaper such that when it is pressed into the retractor port 568 and abdomen, it shapes the port 568 in a form that allows for easy insertion of the robot. In one implementation, the port 568 is a retractor port 568 that is commercially available from Johnson & Johnson. In use, the port 568 is positioned in an abdominal incision created for the insertion procedure.

Figure 27A:
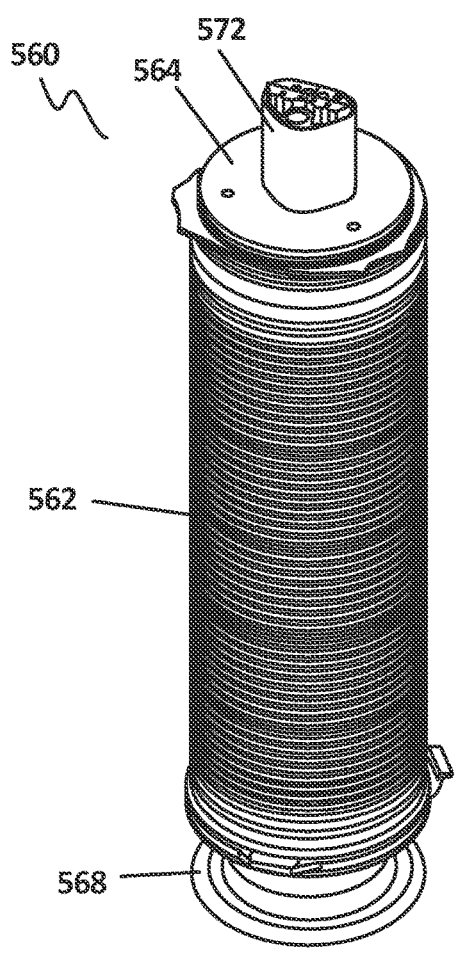
FIG. 27A is a perspective view of an insertion system, according to one embodiment.
Figure 27B:
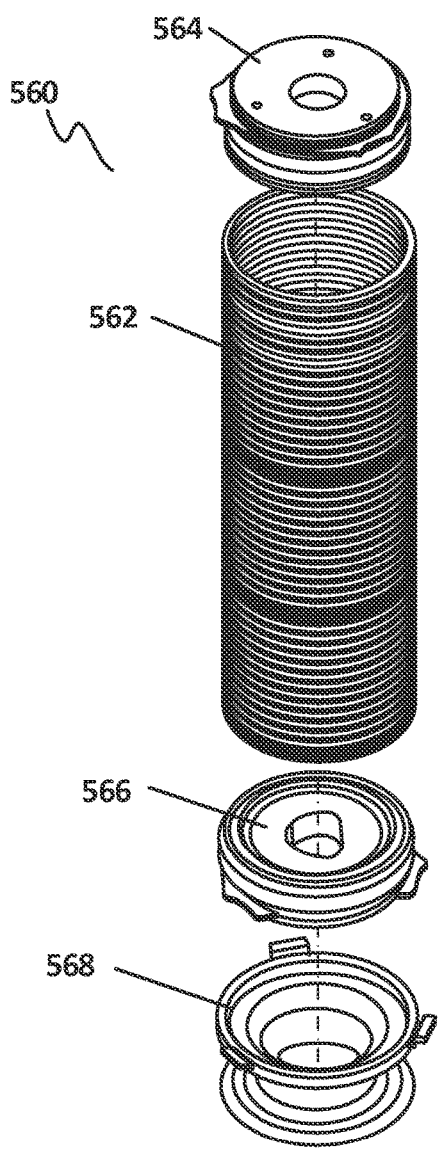
FIG. 27B is an exploded view of the insertion system of FIG. 27A.
Figure 27C:
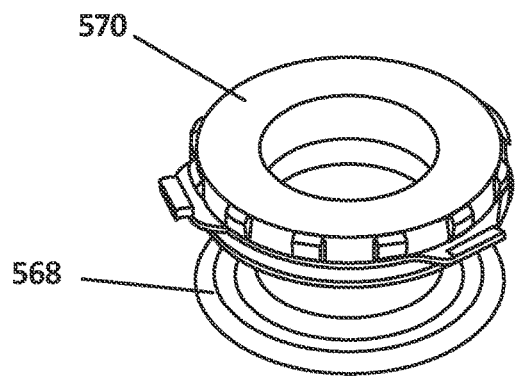
FIG. 27C is a perspective view of a port coupled to a surgical port in the insertion system of FIG. 27A.
Figure 27D:
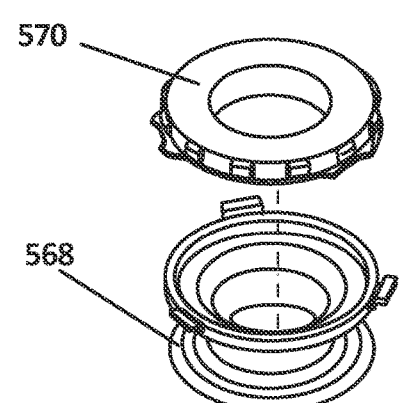
FIG. 27D is an exploded view of the port and surgical port of FIG. 27C.

According to one embodiment as best shown in FIG. 27D, the port 568 can be coupled to a surgical port 570 that has a sphincter-style seal that is configured to form a fluidic seal around a human wrist of a surgeon when the surgeon is performing a hand-assisted laparoscopic surgical procedure. In one implementation, the surgical port 570 is a hand assist laparoscopic surgery (HALS) port that is commercially available from Johnson & Johnson.

In use, according to one implementation, the insertion process can be performed in the following manner. First, the robotic system 572 is placed in its insertion configuration (either automatically or manually). The robotic system 572 is then coupled with the proximal insertion cap 564 as best shown in FIG. 27A such that the cap 564 establishes a seal around a portion of the system 572, and the cap 564 is coupled to the insertion bag 562. Alternatively, the cap 564 can be couple to the bag 562 before the robotic system 572 is coupled to the cap 564. The bag 562 is also coupled to the distal insertion cap 566.

Once an incision is made in the patient that provides access to the target cavity, the bottom ring of the port 568 is inserted into the incision such that the port 568 is positioned in the incision. At this point, the distal insertion cap 566 is coupled to the port 568 such that the bag 562 and the rest of the insertion assembly is coupled to the port 568. The robotic system 572 can then be stabilized as needed prior to a surgical procedure, such as by coupling the system 572 to a positioning rod or a support arm such as described above. Once the cavity is insufflated, the robotic system 572 can be inserted into the cavity by urging the system 572 downward while the system 572 is stepped through its insertion configurations as described in further detail above. Once the system 572 is in the operating configuration, the support arm can be made rigid and the operation can begin.

In one embodiment, the insertion procedure as described herein is substantially manual in nature, with the surgeon performing the procedure by grasping the robotic system with one hand as shown in FIG. 26 while controlling the console with the other. Alternatively, one person can grasp the robotic system while another controls the console. In a further embodiment, a user could command the robotic system using an interface (such as buttons) on the robot itself while it is inserted. These commands would inform the robotic system to step through its predetermined insertion procedure.

Figure 28A:
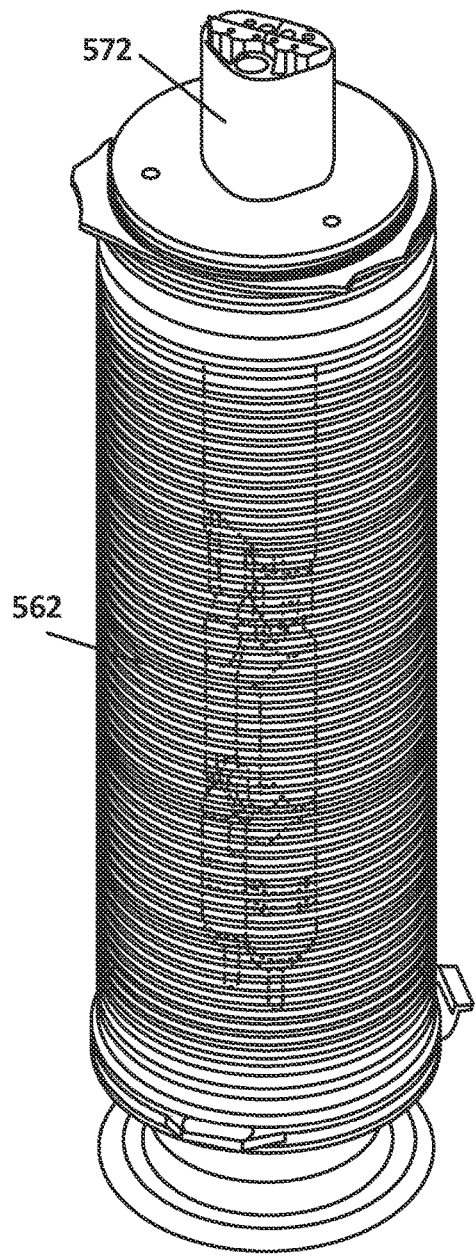
FIG. 28A is a perspective view of the insertion system of FIG. 27A before insertion.
Figure 28B:
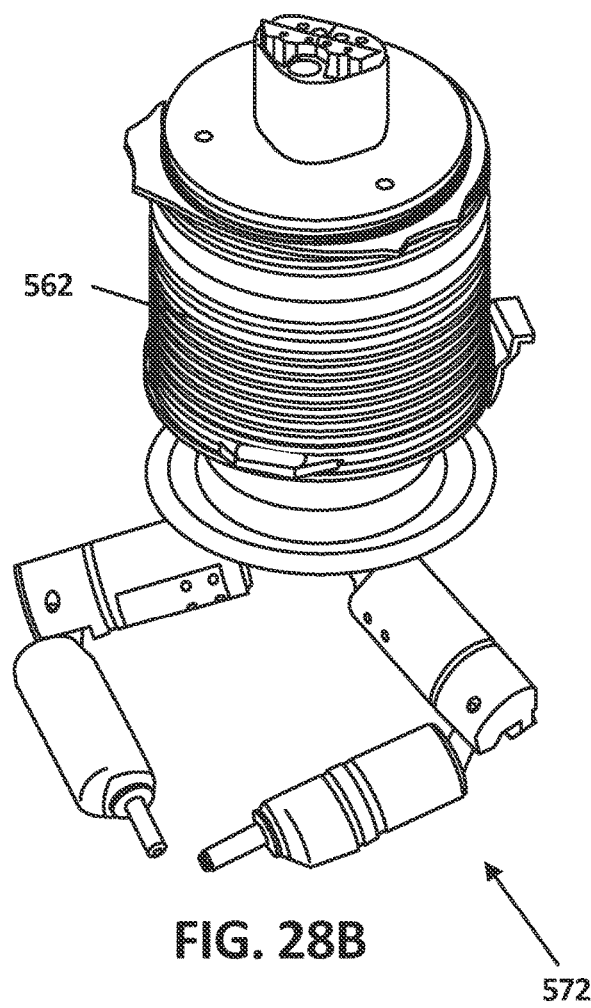
FIG. 28B is a perspective view of the insertion system of FIG. 27A after insertion.

FIGS. 28A and 28B depict the insertion components, including the insertion bag 562, and the robotic system 572 before (FIG. 28A) and after (FIG. 28B) insertion. In this implementation, the insertion bag 562 has accordion-like ribs 574. The ribs 574 help the bag 562 to maintain its circular cross section and not buckle, blow out, or otherwise deform during insertion or at any other time during the procedure. In one embodiment, the insertion components can also include a locking mechanism (not shown) configured to retain the bag 562 in the configuration shown in FIG. 28B, thereby preventing the bag 562 from re-expanding due to internal pressure. In addition, height sensors can also be provided in certain implementations to provide information to the software and/or the surgeon regarding the status of the insertion procedure. This information can be used during the insertion procedure to inform and/or control the insertion configurations of the robot.

Figure 29:
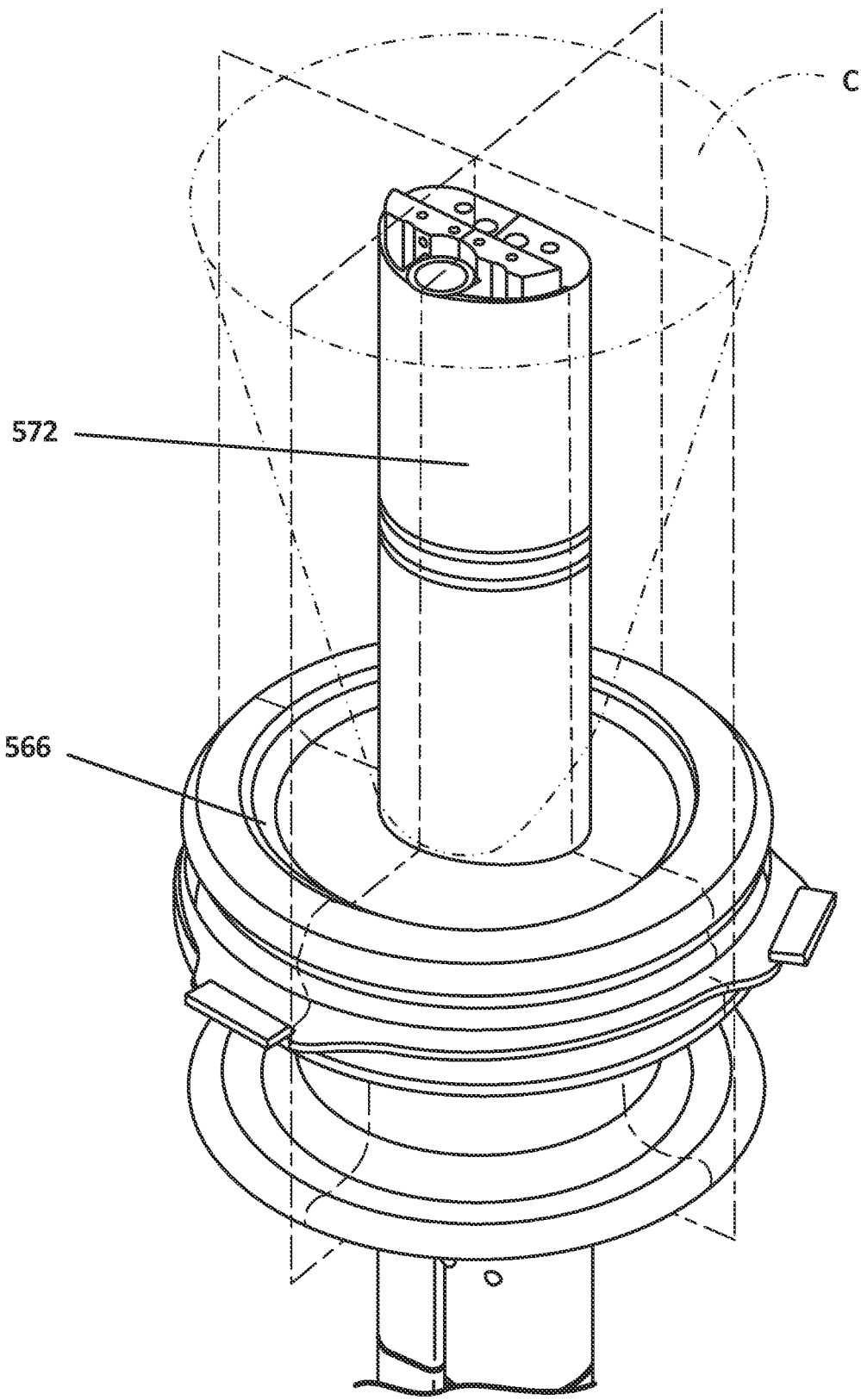
FIG. 29 is a schematic view of a robotic device positioned in the insertion system of FIG. 27A.

In the embodiment depicted in FIG. 29, the distal insertion cap 566 is configured to allow the robotic system 572 to rotate about 180 degrees about its longitudinal axis while also allowing the system 572 to tilt about 15 degrees in both pitch and yaw, as depicted schematically with the representative cone of movement C. Alternatively, any other rotation and/or tilt limits can be implemented.

Alternatively, the robotic system embodiments discussed above can be inserted into the target cavity via any known methods and devices. In one implementation, the extraction procedure can follow the same set of steps as the insertion procedure, but in reverse order. Alternatively, any known extraction method can be used.

Figure 30A:
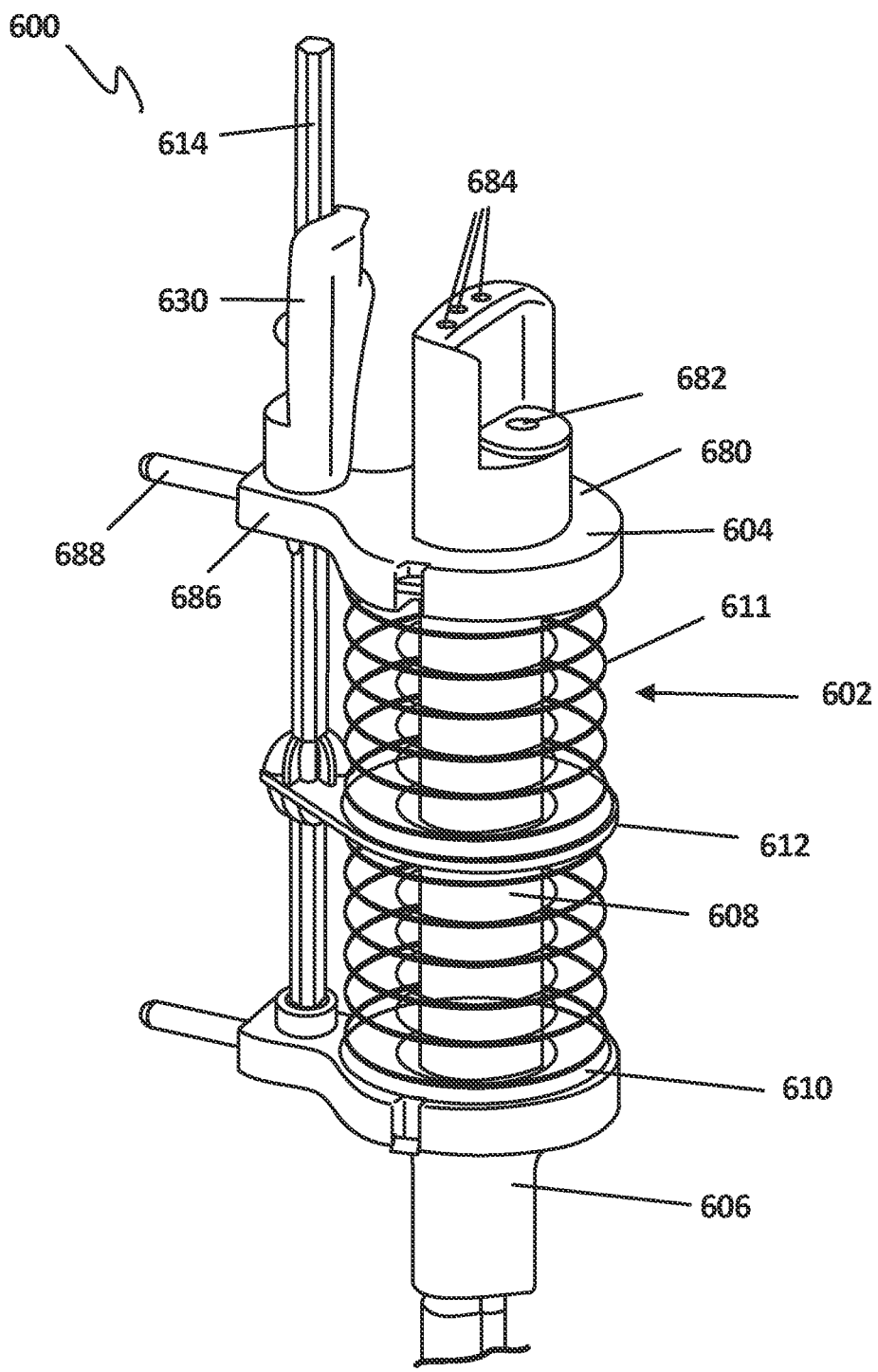
FIG. 30A is a perspective view of an external pressurized insertion system, according to one embodiment.

An alternative implementation of an external pressurized system or apparatus 600 is shown in FIGS. 30A-36B. The apparatus 600 has a flexible container, canister, or bag 602 with a top cap 604 coupled to a top portion of the flexible canister 602. In this embodiment, the container 602 has a port 606 that is coupled to the container 602 at a base portion of the container 602. In this particular implementation, the port 606 is a dilator port 606. Alternatively, any known port can be used. The dilator port 606 is configured to be positionable in an incision in the skin of the patient, thereby providing access to a cavity of the patient. As best shown in FIGS. 30A and 31A, the apparatus 600 is configured to receive a surgical device 608 such that the device 608 can be inserted into the patient cavity through the port 606 of the apparatus 600.

As best shown in FIG. 30A, in addition to the top cap 604 coupled to the top or proximal portion of the canister 602, the system 600 in this embodiment also has a base coupling component (also referred to as a "base coupler" or "bottom cap") 610 coupled to a bottom portion of the canister 602 (which couples to the dilator port 606) and a support frame 612 coupled along the body of the canister 602. Each of the top cap 604, base coupling component 610, and support frame 612 are also coupleable to a support rod (also referred to as a "alignment rod") 614, as best shown in FIGS. 30A and 30D. The support frame 612 is configured to provide support to the canister 602 during compression of the canister 602, thereby preventing the buckling or deformation of the canister 602. The top cap 604 and support frame 612 are slidably coupled to the support rod 614 such that the top cap 604 and the support frame 612 can be slid in relation to the rod 614 to move the system 600 between a retracted position and a deployed position as discussed in further detail below.

As best shown in FIGS. 30A and 30C, the dilator port 606 has a distal lip 650 that defines a bottom cap coupling portion 652, a body 654, a port lumen 656, a projection 658, and a rod lumen 660 configured to receive the support rod 614. The distal lip 650 and bottom cap coupling portion 652 are configured to couple to the bottom cap 610 such that a fluidic seal is established between the bottom cap 610 and the port 606, thereby allowing for the system 600 to be used to maintain the insufflations of the patient's cavity during insertion, operation, retraction, and repositioning of any surgical device using the system 600. In addition, according to one embodiment, the projection 658 also has a connection rod 662 extending from the projection 658. The connection rod 662 can be used to couple the system 600 to a surgical table, an iron intern, or any other stable item that can be used to stabilize the system 600 and/or maintain the positioning thereof.

In accordance with one implementation, the body 654 of the port 606 is shaped to define the lumen 656 to have a cross-section that is substantially similar to the external cross-section of the surgical device 608 that is positionable through the port 606. This specific shape of the body 654 allows for using the smallest possible body 654 diameter and thus using the smallest possible incision in the patient. In addition, this specific embodiment has two recessed portions or notches 616A, 616B on the lip 650 that are configured to receive the bottom cap 610 projections 618A, 618B (as best shown in FIG. 30B). As such, the port 606 and bottom cap 610 can be removably coupled together by coupling the projections 618A, 618B with the notches 616A, 616B of the port 606.

The support frame 612, as best shown in FIG. 30B, is operably coupled to the canister 602. The frame 612 has a projection 622 with a support body 624. The support body 624 defines a lumen 626 configured to receive the support rod 614. In one embodiment, the support body 624 is configured to maintain space between the top cap 604, the support frame 612, and the port 606 when the system 600 is in its fully deployed configuration, as best shown in FIG. 31B.

Returning to FIGS. 30A and 30D, the support rod 614, according to one embodiment, has a hexagonal cross-section. Alternatively, the support rod 614 can have a square-shaped cross-section, triangular-shaped cross-section, or any other cross-section configuration that allow for coupling the support rod 614 to the other components (such as the dilator port 606, the support frame 612, and the top cap 604) such that the other components can be slidably coupled to the support rod 614 but cannot rotate in relation to the rod 614.

As best shown in FIGS. 30A, 30E, 30F, and 30G, certain embodiments of the system 600 include a handle 630. The handle 630 has a body 632, a base portion 634 in the body 632 that is larger than the rest of the body 632, a lumen (not shown) defined through the base portion 634 that is configured to receive the support rod 614, and an actuation lever (also referred to herein as a "trigger") 636 pivotally coupled at a pivot 638 to the body 632 and operably coupled to a coupling component 640 such that actuation of the trigger 636 causes the coupling component 640 to move. More specifically, in one implementation, the coupling component 640 has a lumen (not shown) that is configured to receive the support rod 614 and be coupleable with the rod 614. In addition, the handle 630 also has three distal projections 642A, 642B, 642C configured to be positionable through and coupleable with the lumen (not shown) defined in the projection 686 on the top cap 604.

When the trigger 636 is in the unactuated configuration as shown in FIGS. 30E, 30F, and 30G, the coupling component 640 is positioned in relation to the handle 630 such that the coupling component 640 is in contact with the rod 614, causing a friction coupling between the coupling component 640 and the rod 614. Thus, in the unactuated configuration, the handle 630 is frictionally fixed to the rod 614 such that the handle 630 will not slide along the rod 614, thereby retaining the handle 630 on the support rod 614 at that location. When the trigger 636 is actuated (or otherwise moved) to the actuated configuration in which the trigger 636 is positioned closer to the body 632 (not shown), the movement of the trigger 636 causes the coupling component 640 to move such that it is released from the frictional coupling to the support rod 614, thereby freeing the handle 630 to slide up or down in relation to the support rod 614, as will be described in further detail below.

According to one embodiment, the container 602 in this device 600 is made of a flexible material such as, for example, polyethylene plastic, latex, nylon, or silicone rubber. Alternatively, any known flexible material for use with a medical device can be used. Further, the specific embodiment depicted in FIGS. 30A-36B has ribs 611 (or has an "accordion-like" configuration), which facilitate compression of the container 602 without deformation thereof. Alternatively, certain embodiments do not have ribs. As such, the container 602 can be manipulated and configurable with respect to the shape of the container 602, and more specifically can be compressed longitudinally such that the height of the container 602 can be reduced during insertion of a robotic device into a patient's cavity. This will be described in further detail herein.

As best shown in FIG. 30A, the top cap 604 has a cap body 680, an access lumen 682, smaller lumens 684 and a projection 686 that has a support rod lumen (not shown) through which the support rod 614 can be positioned. In addition, according to one embodiment, the projection 618 also has a connection rod 688 extending from the projection 618. The connection rod 688 can be used to couple the system 600 to a surgical table, an iron intern, or any other stable item that can be used to stabilize the system 600 and/or maintain the positioning thereof.

In use, as one specific step of a larger surgical procedure (described generally below), the system 600 can be used to deploy the surgical device 608 into a body cavity of a patient in the following manner, according to one implementation as best shown in FIGS. 31A and 31B. The system 600 is positioned such that the port 606 is positioned through the incision formed in the patient's cavity wall with the surgical device 608 positioned in the retracted configuration as shown in FIG. 31A. The surgeon can then actuate the trigger 636, thereby releasing the handle 630 such that it can be moved distally along the support rod 614. In one embodiment, the top cap 604 can be advanced distally to a substantially midpoint, such as at the location along the support rod 614 where the support frame 612 is positioned. In another implementation, the top cap 604 can be advanced distally such that the system 600 is in the fully deployed configuration, as best shown in FIG. 31B.

Figure 32A:
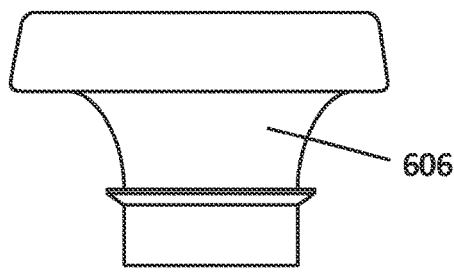
FIG. 32A is a side view of the port of the system of FIG. 30A.
Figure 32B:
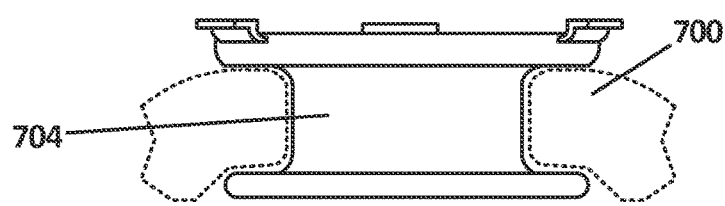
FIG. 32B is a side view of a dilator for use with the system of FIG. 30A.
Figure 33A:
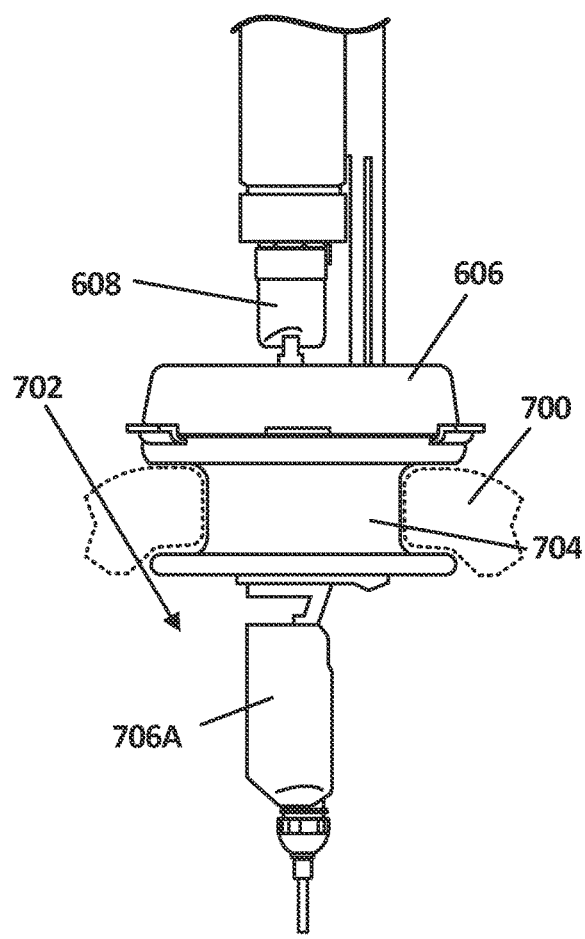
FIG. 33A is a side view of the system of FIG. 30A in which the surgical device is being inserted into the cavity of the patient.
Figure 33B:
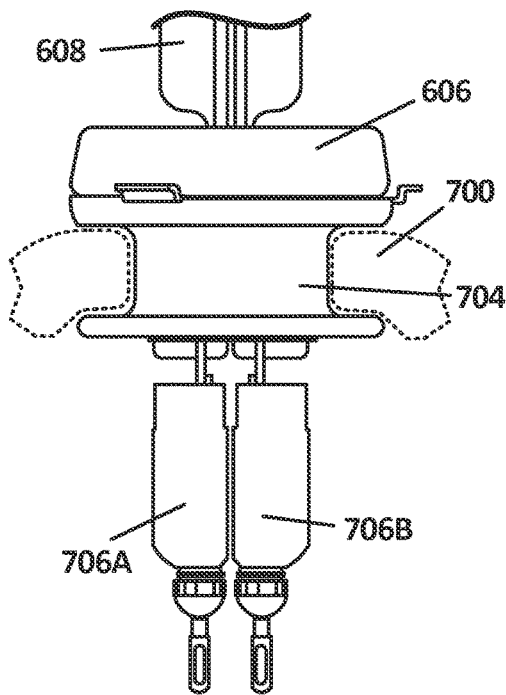
FIG. 33B is a front view of the system as shown in FIG. 33A.

FIGS. 32A-36B depict one set of steps for using the system 600 to perform a procedure. More specifically, these steps relates to the use of the system 600 to perform the steps described above with respect to FIGS. 12A-17D. Thus, in use, according to one embodiment, first an incision is formed in the wall 700 of the patient's cavity 702, and a dilator 704 is positioned in the incision as shown in FIG. 32B. The port 606 as shown in FIG. 32A is then coupled to the dilator 704. Then, as shown in FIGS. 33A and 33B, the surgical device 608 is positioned through the port 606 and dilator 704. Once the device 608 is positioned through the port 606, the canister 602 is coupled to the port 606 as shown in FIGS. 34A and 34B. More specifically, the bottom cap 610 of the canister 602 is coupled to the port 606 as shown.

Figure 36A:
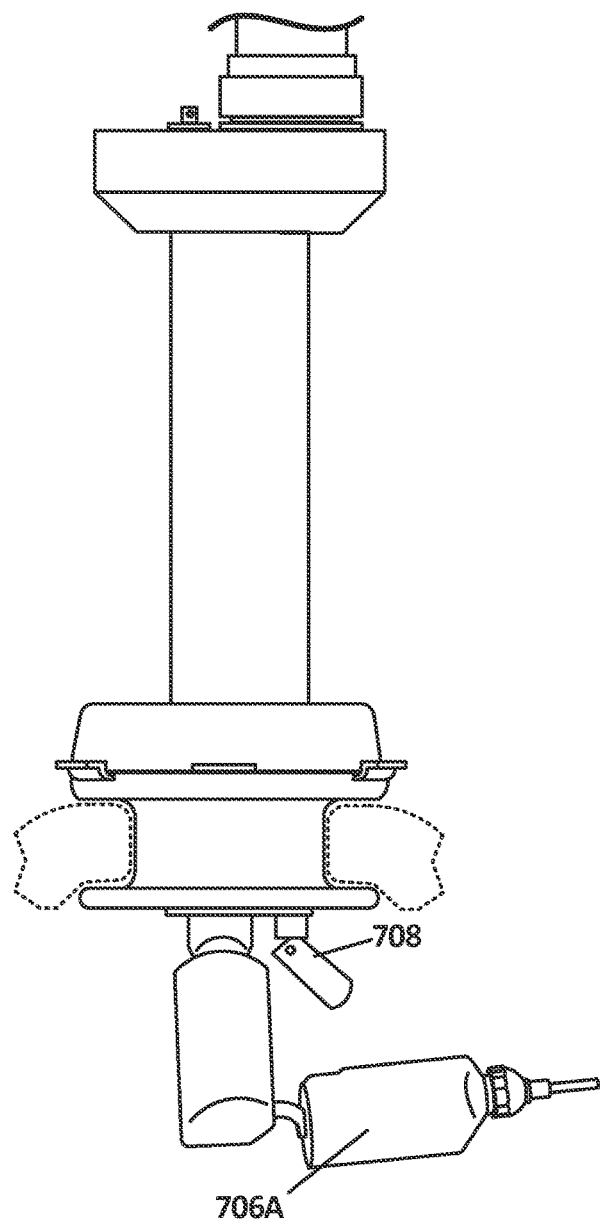
FIG. 36A is a side view of the system of FIG. 30A in which the arms of the surgical device have been angled to optimize the positioning of the end effectors.
Figure 36B:
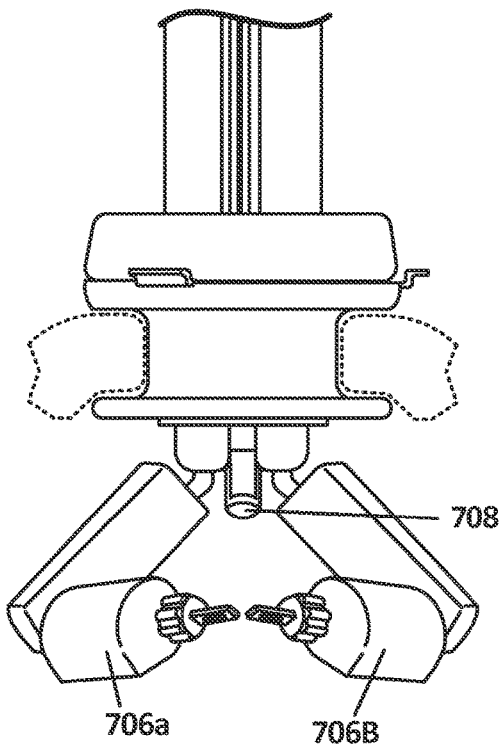
FIG. 36B is a front view of the system as shown in FIG. 36A.

Further, in certain implementations, as described in further detail above with respect to FIGS. 12A-17D, the arms 706A, 706B of the device 608 are actuated to bend at the elbows, and a camera 708 is extended distally from the device 608 as shown in FIGS. 34A and 34B. Further, in some embodiments, the arms of the device 608 can be further actuated to move away from each other and the camera 708 can be further actuated to bend as shown in FIGS. 35A and 35B. In addition, the forearms of the arms 706A, 706B can be actuated to move toward each other as depicted in FIGS. 36A and 36B, thereby resulting in a configuration that optimizes positioning of the end effectors on the arms 706A, 706B in a way that is not attainable using standard laparoscopic surgical tools, which are constrained by restrictions such as port placement, etc.

FIGS. 37A-37C depict one embodiment of a console 800 that can be used with any of the robotic systems and/or surgical theater configurations described above. The console 800 can be used to control a robotic system and other devices as well as interact with information and possibly other surgeons or personnel. The console 800 has a monitor 802, a secondary monitor 804, and joysticks 806A, 806B. The surgeon can view a variety of visual information including feedback from the surgical camera on the monitor 802. The monitor 802 can also display information about the state of the robotic system, the patient, etc. The secondary monitor 804 can display further information, including, for example, several robot functions and controls. In one implementation, both monitors 802, 804 can be touch screens to allow the surgeon to select and input information. Alternatively, the console 800 can have only one monitor or three or more monitors.

The joysticks 806A, 806B allow the surgeon to control the robot. In one embodiment, the joysticks 806A, 806B provide haptic feedback and sensations based on various states of the robotic system. Alternatively, the joysticks 806A, 806B do not provide haptic feedback. According to one embodiment, the monitors 802, 804 and the joysticks 806A, 806B can be adjusted in position and angle for the comfort of the surgeon.

The console 800 has a console support structure 808 as best shown in FIG. 30C. The joysticks 806A, 806B are supported by a horizontal beam 810 that is supported by a central spine 812. The central spine 812 can also be configured to elongate or shorten (either manually or by electronic or other actuation) to raise or lower the upper portion of the console 800, thereby allowing the surgeon to interact with the console 800 either while in a sitting or standing position. In one embodiment, the spine 812 is configured to elongate and shorten such that the monitors 802, 804 and the joysticks 806A, 806B move together. Alternatively, the spine 812 can be configured to elongate and shorten such that the monitors 802, 804 move separately in relation to the joysticks 806A, 806B.

In one implementation, the console 800 has lockable wheels (not shown). The console can also have a central tray 814 at the base of the console 800 to house foot pedal(s). The console 800 also has a box or other structure 816 to house computer(s), power supply(s), and other electronics. Various computers and other electronics may also exist throughout the console (e.g. in the displays).

Figure 38A:
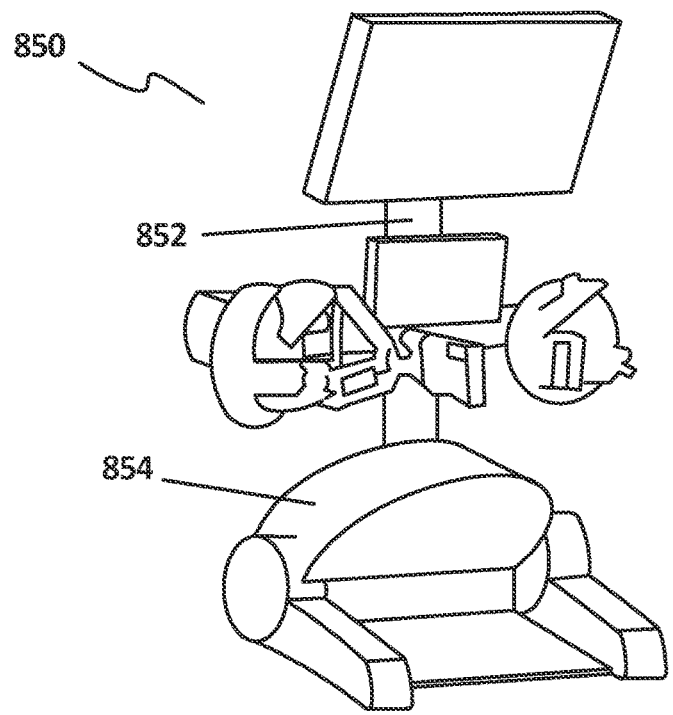
FIG. 38A is a perspective view of another console that can be used with any of the surgical device embodiments disclosed herein, according to another embodiment.
Figure 38B:
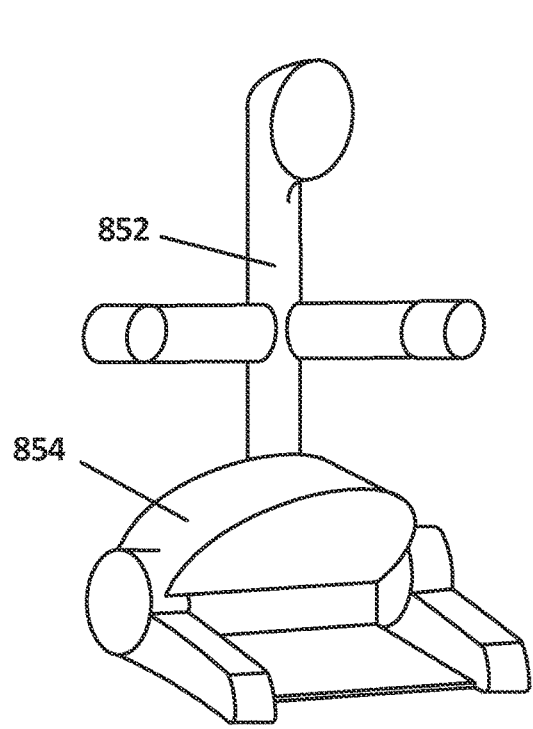
FIG. 38B is a perspective view of the frame of the console of FIG. 38A.
Figure 38C:
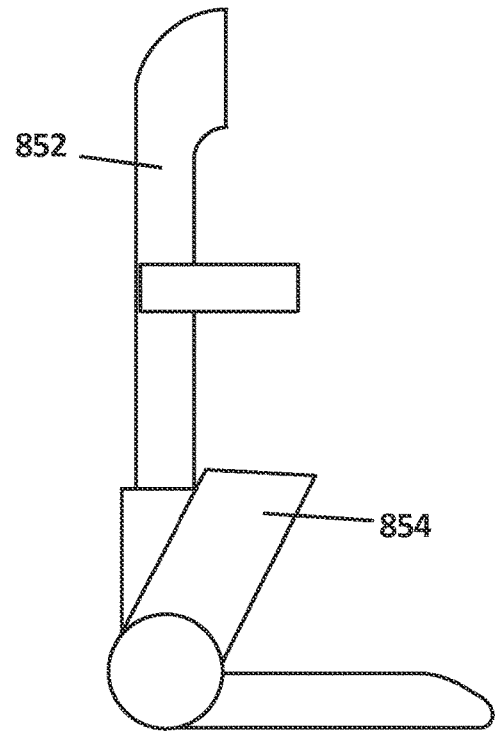
FIG. 38C is a side view of the frame of the console of FIG. 38A.

Another embodiment of a console 850 is shown in FIGS. 38A-38C. While many of the components are substantially similar to those of the console 800 above, this console 850 has a spine 852 that is cylindrical, which can simply extension and retraction of the spine 852. The console 850 also has an electronics box 854 with a different configuration.

Figure 39A:
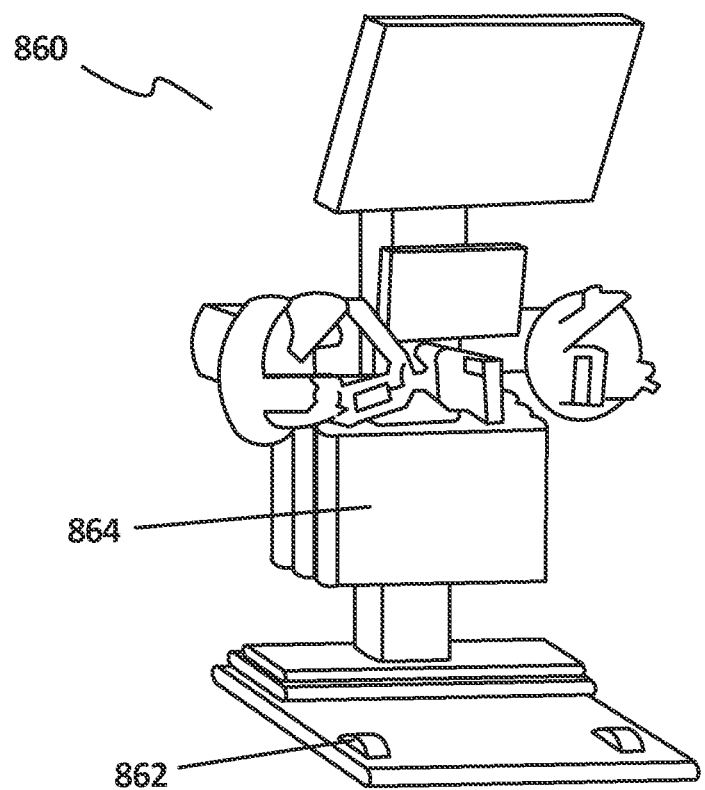
FIG. 39A is a perspective view of another console that can be used with any of the surgical device embodiments disclosed herein, according to a further embodiment.
Figure 39B:
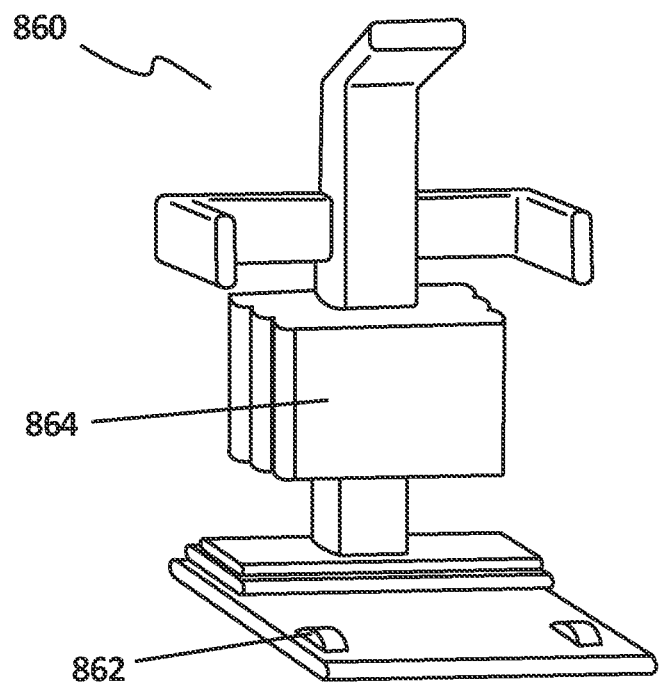
FIG. 39B is a perspective view of the frame of the console of FIG. 39A.

A further implementation of a console 860 is shown in FIGS. 39A and 39B. Most components are substantially similar to those of the consoles 800, 850 above, but this console 860 has open wheels 862 and an elevated electronics box 864.

Figure 40A:
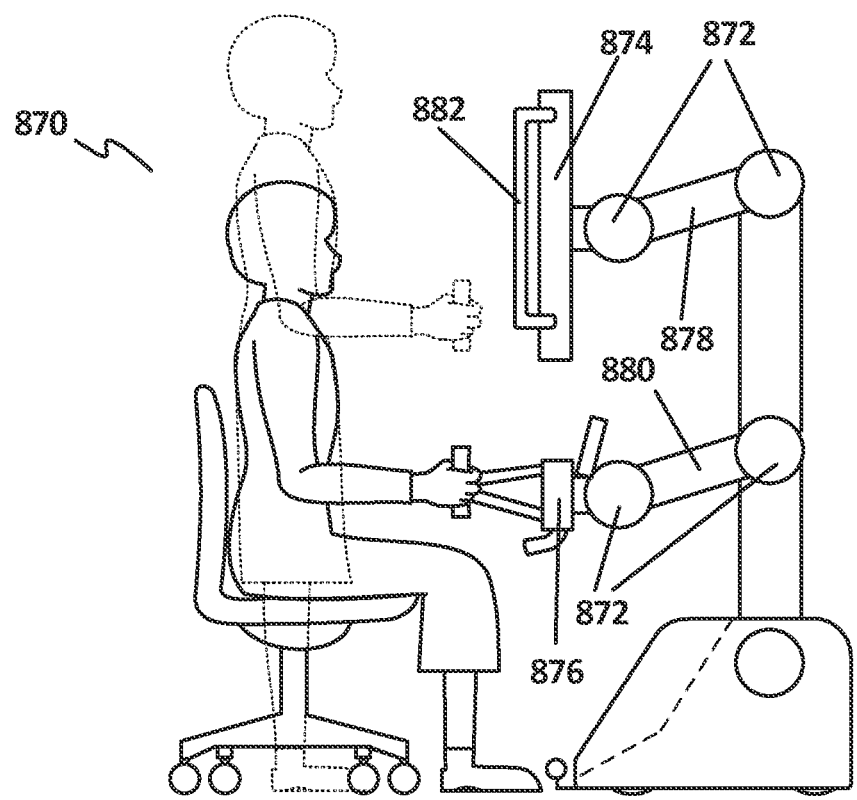
FIG. 40A is a side view of yet another console that can be used with any of the surgical device embodiments disclosed herein, according to yet another embodiment.
Figure 40B:
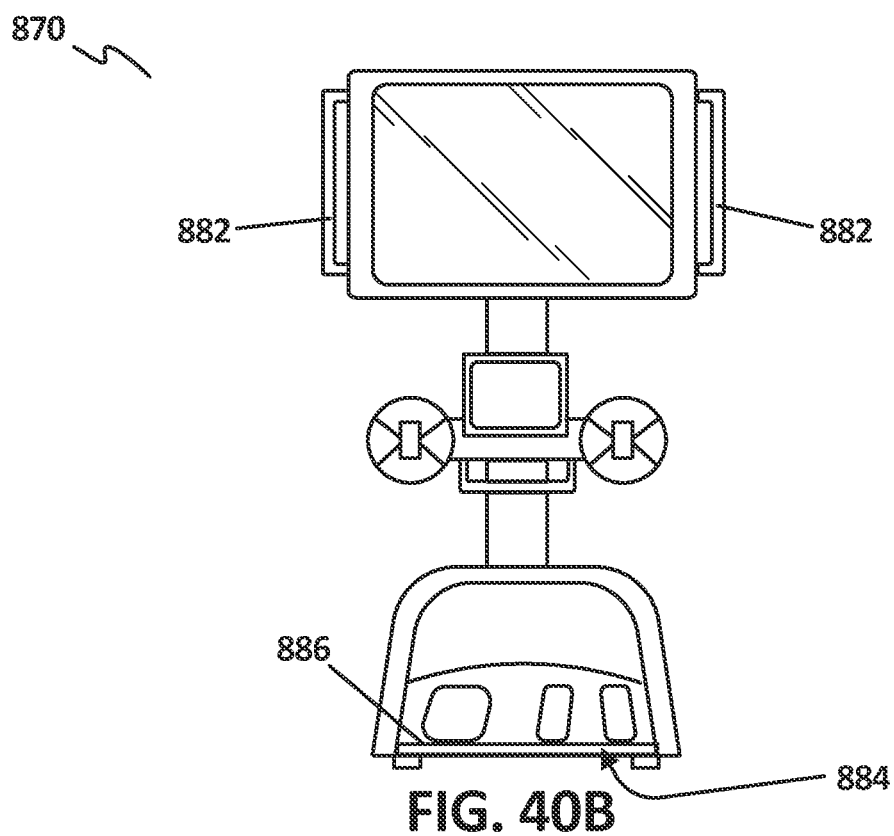
FIG. 40B is a front view of the console of FIG. 40A.
Figure 41A:
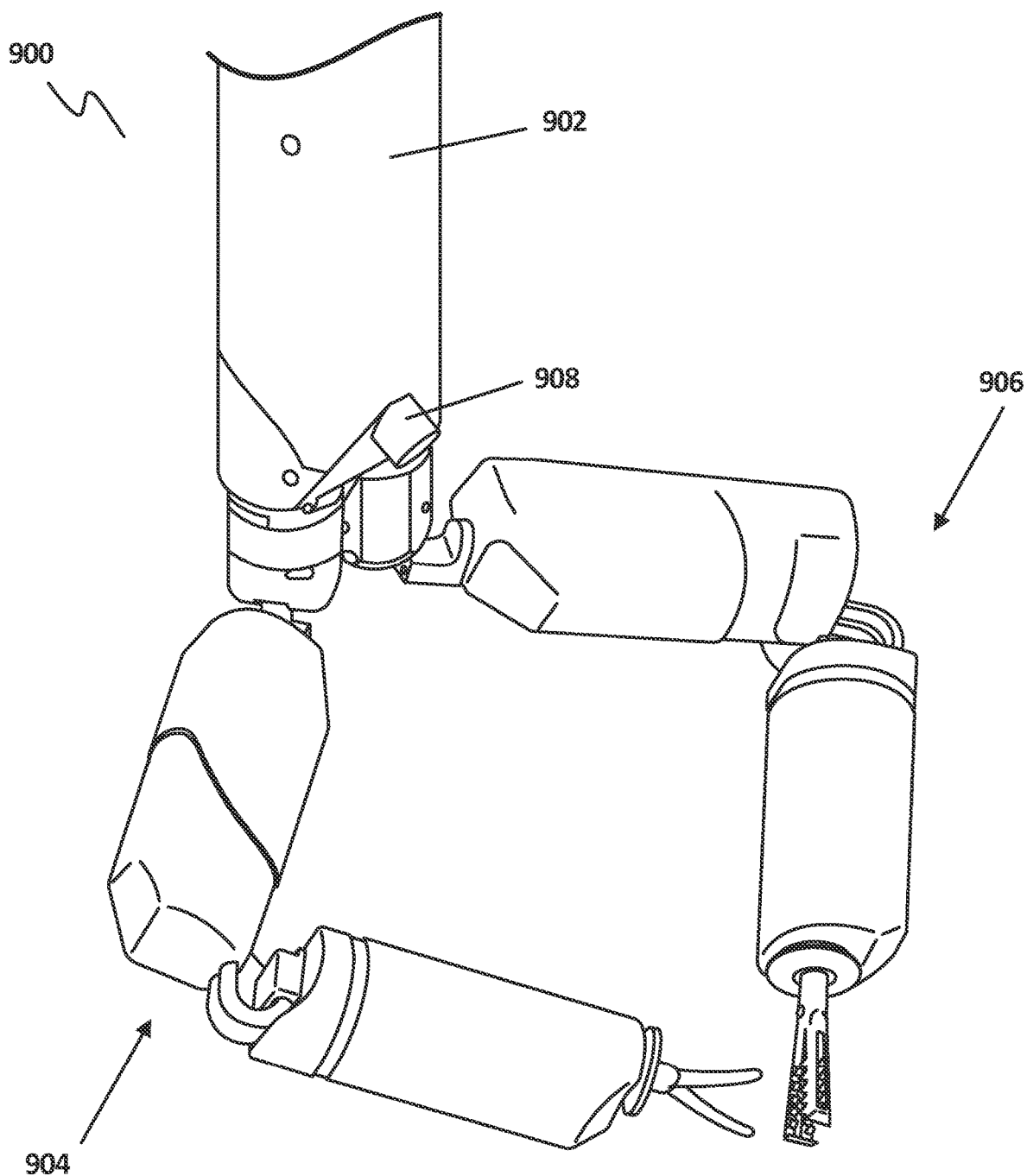
FIG. 41A is a perspective view of a robotic device, according to one embodiment.
Figure 41B:
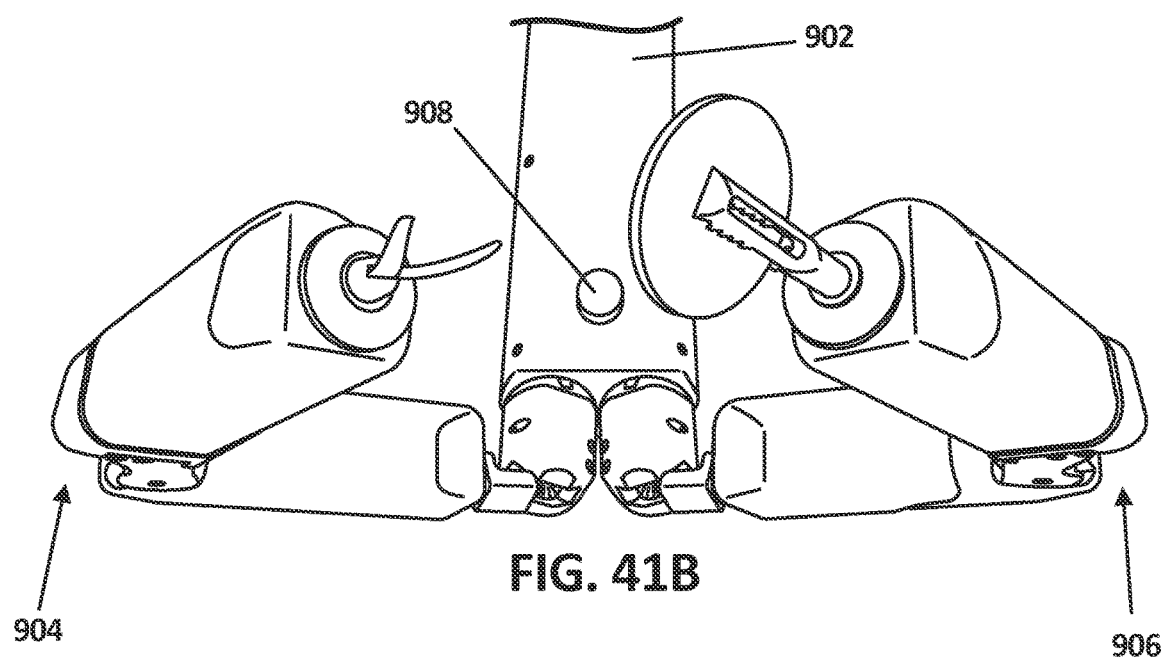
FIG. 41B is another perspective view of the robotic device of FIG. 41A.
Figure 41C:
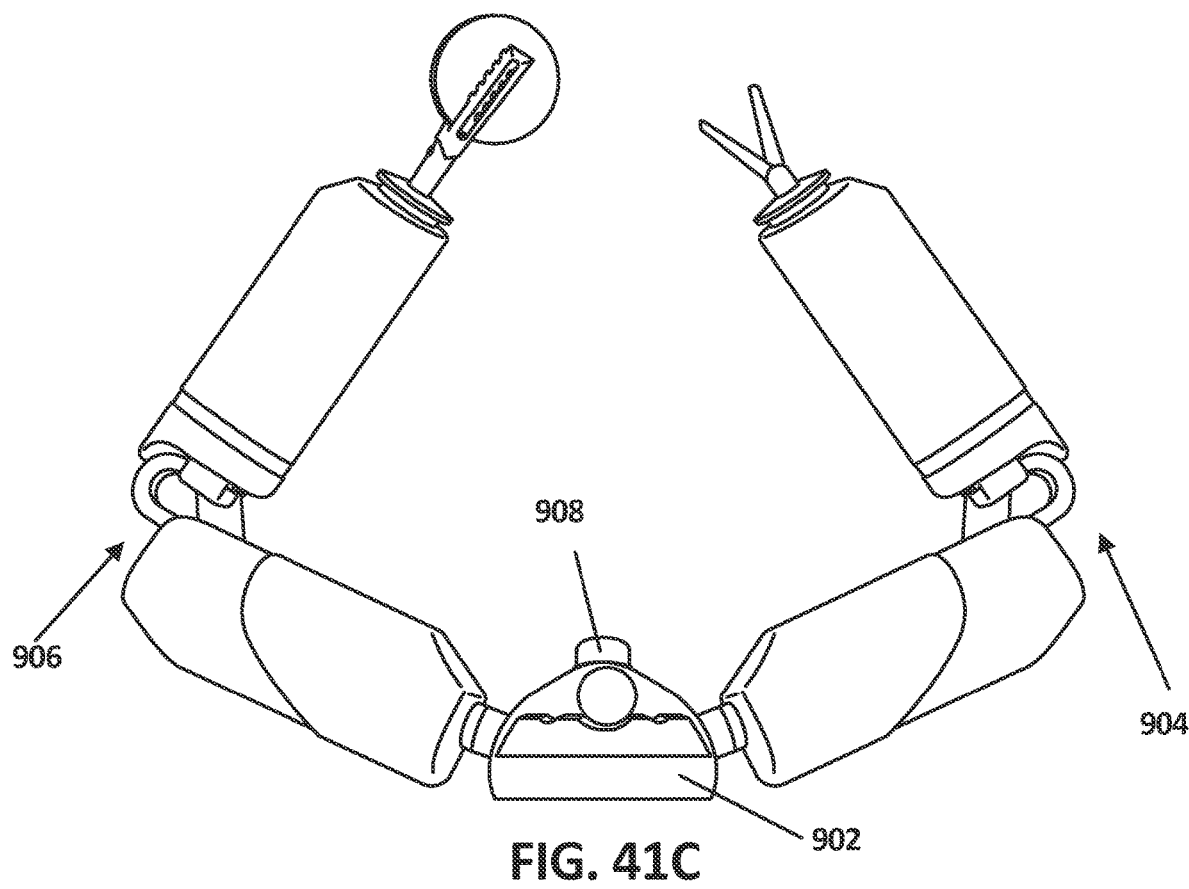
FIG. 41C is a top view of the robotic device of FIG. 41A.
Figure 41D:
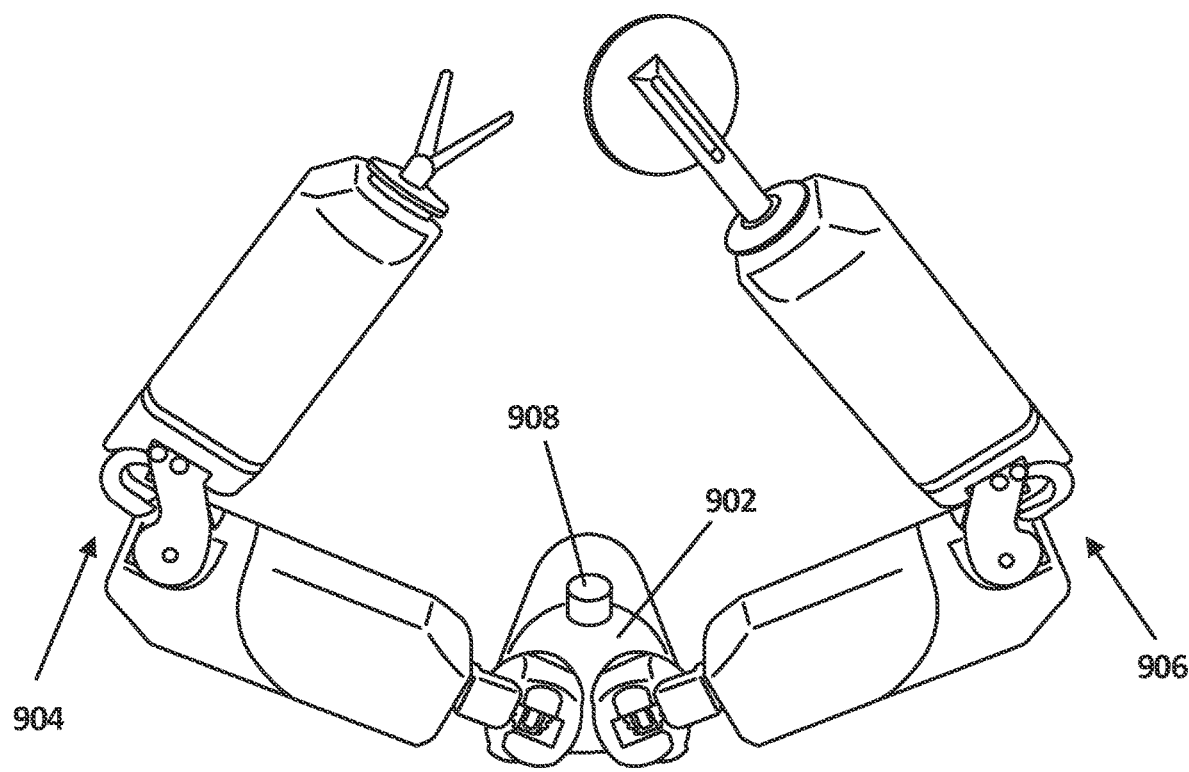
FIG. 41D is a bottom view of the robotic device of FIG. 41D.

FIGS. 40A and 40B depict another embodiment of a console 870 with components similar to those described above. In this embodiment, the console 870 has revolute joints 872 that allow the display 874 and joystick 876 support structures 878, 880 to both move up and down (sitting or standing) and to tilt. These motions can be independent or coupled. The sit/stand motion can also be coupled (between the upper display and lower joystick) or independent. The monitor 874 has handles 882 to allow for movement of the monitor 874. Foot pedals 884 are shown at the center of the base that also serves as the electronics box. A foot rail 886 is also shown to support the surgeon's feet as he/she uses the pedals.

FIGS. 41A-41D depict one embodiment of a robotic system 900. The system 900 has a device body 902, a right arm 904, and a left arm 906. The device body 902 has a camera 908 protruding from a lumen (not shown) in the body 902.

Although the present invention has been described with reference to preferred embodiments, persons skilled in the art will recognize that changes may be made in form and detail without departing from the spirit and scope of the invention.

What is claimed is:

1. A robotic surgical system, comprising:
   (a) a device body comprising a housing, comprising:
      (i) a distal end;
      (ii) a proximal end,
      (iii) a camera lumen defined within the device body such that the camera lumen comprises a proximal lumen opening in the proximal end of the device body and a distal lumen opening in the distal end of the device body; and
      (iv) at least two motorized body actuators fixedly disposed within the device body;
   (b) first and second shoulder joints operably attached to the distal end of the device body and operably coupled with the at least two motorized body actuators;
   (c) a first robotic arm pivotally attached to the first shoulder joint, the first robotic arm comprising:
      (i) an upper arm comprising a housing enclosing at least one first arm motorized actuator;
      (ii) a forearm comprising a housing enclosing at least one first arm motorized actuator; and
      (iii) a plurality of first arm actuator gears and first arm driven gears constructed and arranged to translate movement of the first arm motorized actuators to movement of the first robotic arm;
   (d) a second robotic arm pivotally attached to the second shoulder joint, the second robotic arm comprising:
      (i) an upper arm comprising a housing enclosing at least one second arm motorized actuator;
      (ii) a forearm comprising a housing enclosing at least one second arm motorized actuator; and
      (iii) a plurality of second arm actuator gears and second arm driven gears constructed and arranged to translate movement of the second arm motorized actuators to movement of the second robotic arm; and
   (e) a camera component, comprising:
      (i) a controller body;
      (ii) an elongate tube operably coupled to the controller body, wherein the elongate tube is configured and sized to be positionable through the camera lumen defined in the device body, the elongate tube comprising:
         (A) a rigid section;
         (B) an optical section; and
         (C) a flexible section operably coupling the optical section to the rigid section,
      wherein:
         (i) the camera lumen is disposed between the at least two motorized body actuators; and
         (ii) the elongate tube has a length such that the optical section is configured to extend distally from the distal lumen opening when the camera component is positioned through the camera lumen.

2. The robotic surgical system of claim 1, wherein the controller body comprises a controller configured to operate the camera component.

3. The robotic surgical system of claim 1, wherein the distal lumen opening is positioned between the first and second shoulder joints.

4. The robotic surgical system of claim 1, wherein the optical section is configured to be tiltable at the flexible section in relation to the rigid section, wherein the optical section has a straight configuration and a tilted configuration.

5. The robotic surgical system of claim 1, wherein the elongate tube is configured to be rotatable in relation to the controller body.

6. The robotic surgical system of claim 1, wherein the flexible section comprises a tension component operably coupled to the optical section.

7. The robotic surgical system of claim 6, wherein the tension component comprises a decreased tensioned state in which the optical section is in a straight configuration and an increased tensioned state in which the optical section is in a tilted configuration.

8. The robotic surgical system of claim 7, wherein the flexible section further comprises an elongate actuation component configured to apply force to the optical section, wherein the force opposes a tension of the tension component.

9. The robotic surgical system of claim 8, further comprising:
   (a) an articulated flexible spine, wherein the elongate actuation component is disposed through the articulated flexible spine; and
   (b) a plurality of disks operably coupled to the articulated flexible spine and the tension component,
   wherein the tension component comprises a spring element, wherein the spring element is operably coupled at a first end to the optical section and at a second end to the rigid section.

10. The robotic surgical system of claim 8, wherein the flexible section comprises an elbow joint, wherein the elongate actuation component comprises a first cable disposed on a first side of the elbow joint, and wherein the tension component comprises a second cable disposed on a second, opposing side of the elbow joint.

11. A robotic surgical system, comprising:
    (a) a device body comprising a housing, comprising:
       (i) at least two motorized body actuators disposed within the device body;
       (ii) a receptacle disposed at a proximal portion of the device body; and
       (iii) a camera lumen defined within the device body such that the camera lumen comprises a proximal lumen opening in the receptacle and a distal lumen opening defined in a distal portion of the device body;
(b) first and second shoulder joints operably attached to the distal portion of the device body and operably coupled with the at least two motorized body actuators;
(c) a first robotic arm pivotally attached to the first shoulder joint, the first robotic arm comprising:
(i) an upper arm comprising a housing enclosing at least one first arm motorized actuator;
(ii) a forearm comprising a housing enclosing at least one first arm motorized actuator; and
(iii) a plurality of first arm actuator gears and first arm driven gears constructed and arranged to translate movement of the first arm motorized actuators to movement of the first robotic arm;
(d) a second robotic arm pivotally attached to the second shoulder joint, the second robotic arm comprising:
(i) an upper arm comprising a housing enclosing at least one second arm motorized actuator;
(ii) a forearm comprising a housing enclosing at least one second arm motorized actuator; and
(iii) a plurality of second arm actuator gears and second arm driven gears constructed and arranged to translate movement of the second arm motorized actuators to movement of the second robotic arm; and
(e) a removable camera system, comprising:
(i) a controller body configured to be mateably positionable within the receptacle; and
(ii) an elongate tube operably coupled to the controller body, wherein the elongate tube is configured and sized to be positionable through the camera lumen defined in the device body,
wherein the elongate tube has a length such that a portion of the elongate tube is configured to extend distally from the distal lumen opening when the controller body is positioned within the receptacle.

12. The robotic surgical system of claim 11, wherein the elongate tube further comprises:
(a) a substantially rigid section;
(b) an optical section; and
(c) a flexible section operably coupling the optical section to the rigid section,
wherein the optical section is configured to be tiltable at the flexible section in relation to the rigid section, wherein the optical section has a straight configuration and a tilted configuration.

13. The robotic surgical system of claim 12, wherein the flexible section comprises a tension component operably coupled to the optical section.

14. The robotic surgical system of claim 13, wherein the tension component comprises a decreased tensioned state in which the optical section is in the straight configuration and an increased tensioned state in which the optical section is in the tilted configuration.

15. The robotic surgical system of claim 14, wherein the flexible section further comprises an elongate actuation component configured to apply force to the optical section, wherein the force opposes a tension of the tension component.

16. The robotic surgical system of claim 15, further comprising:
(a) an articulated flexible spine, wherein the elongate actuation component is disposed through the articulated flexible spine; and
(b) a plurality of disks operably coupled to the articulated flexible spine and the tension component,
wherein the tension component comprises a spring element, wherein the spring element is operably coupled at a first end to the optical section and at a second end to the rigid section.

17. The robotic surgical system of claim 15, wherein the flexible section comprises an elbow joint, wherein the elongate actuation component comprises a first cable disposed on a first side of the elbow joint, and wherein the tension component comprises a second cable disposed on a second, opposing side of the elbow joint.

18. The robotic surgical system of claim 11, wherein the distal lumen opening is positioned between the first and second shoulder joints.

19. The robotic surgical system of claim 11, wherein the elongate tube is configured to be rotatable in relation to the system body.

20. The robotic surgical system of claim 11, further comprising a positioning rod operably coupled to the device body.

21. The robotic surgical system of claim 20, wherein the positioning rod further comprises a handle operably coupled to the positioning rod.

22. A robotic surgical system, comprising:
(a) a device body comprising a housing, comprising:
(i) a distal end;
(ii) a proximal end,
(iii) first and second motorized body actuators fixedly disposed within the device body;
(iv) a receptacle disposed at the proximal end of the device body; and
(iv) a camera lumen defined within the device body such that the camera lumen comprises a proximal lumen opening in the receptacle and a distal lumen opening in the distal end of the device body;
(b) first and second shoulder joints operably attached to the distal end of the device body and operably coupled with the first and second motorized body actuators, respectively;
(c) a first robotic arm pivotally attached to the first shoulder joint, the first robotic arm comprising:
(i) an upper arm comprising a housing enclosing at least one first arm motorized actuator;
(ii) a forearm comprising a housing enclosing at least one first arm motorized actuator; and
(iii) a plurality of first arm actuator gears and first arm driven gears constructed and arranged to translate movement of the first arm motorized actuators to movement of the first robotic arm;
(d) a second robotic arm pivotally attached to the second shoulder joint, the second robotic arm comprising:
(i) an upper arm comprising a housing enclosing at least one second arm motorized actuator;
(ii) a forearm comprising a housing enclosing at least one second arm motorized actuator; and
(iii) a plurality of second arm actuator gears and second arm driven gears constructed and arranged to translate movement of the second arm motorized actuators to movement of the second robotic arm; and
(e) a removable camera component, comprising:
(i) a controller body configured to be removably received within the receptacle;
(ii) an elongate tube operably coupled to the controller body, wherein the elongate tube is configured and sized to be positionable through the camera lumen defined in the device body, the elongate tube comprising:
(A) a rigid section;

(B) an optical section; and
(C) a flexible section operably coupling the optical section to the rigid section, the flexible section comprising:
  (a) a tension component operably coupled to the optical section, wherein the tension component comprises a decreased tensioned state in which the optical section is in a straight configuration and an increased tensioned state in which the optical section is in a tilted configuration; and
  (b) an elongate actuation component operably coupled to the optical section, wherein the elongate actuation component is configured to apply force to the optical section, wherein the force opposes a tension of the tension component.

* * * * *